US009150638B2

(12) United States Patent
Jablonska et al.

(10) Patent No.: US 9,150,638 B2
(45) Date of Patent: Oct. 6, 2015

(54) FACTOR XII INHIBITORS FOR TREATING INTERSTITIAL LUNG DISEASE

(75) Inventors: Ewa Jablonska, Chynów (PL); Klaus Preissner, Giessen (DE); Malgorzata Wygrecka, Giessen (DE)

(73) Assignee: Justus-Liebig-Universität Giessen, Giessen (DE)

( * ) Notice: Subject to any disclaimer, the term of this patent is extended or adjusted under 35 U.S.C. 154(b) by 0 days.

(21) Appl. No.: 13/637,577

(22) PCT Filed: Apr. 1, 2011

(86) PCT No.: PCT/EP2011/055128
§ 371 (c)(1),
(2), (4) Date: Dec. 17, 2012

(87) PCT Pub. No.: WO2011/121123
PCT Pub. Date: Oct. 6, 2011

(65) Prior Publication Data
US 2013/0095108 A1    Apr. 18, 2013

Related U.S. Application Data

(60) Provisional application No. 61/282,801, filed on Apr. 1, 2010.

(30) Foreign Application Priority Data

Apr. 1, 2010 (EP) .................................... 10003652

(51) Int. Cl.
*A61K 39/00* (2006.01)
*C07K 14/81* (2006.01)
*A61K 38/55* (2006.01)
*A61K 39/395* (2006.01)
*A61K 45/06* (2006.01)
*C07K 16/40* (2006.01)
*A61K 38/00* (2006.01)

(52) U.S. Cl.
CPC ................ *C07K 14/81* (2013.01); *A61K 38/55* (2013.01); *A61K 39/3955* (2013.01); *A61K 45/06* (2013.01); *C07K 14/8135* (2013.01); *C07K 16/40* (2013.01); *A61K 38/00* (2013.01); *C07K 2319/31* (2013.01); *C07K 2319/50* (2013.01)

(58) Field of Classification Search
None
See application file for complete search history.

(56) References Cited

U.S. PATENT DOCUMENTS

| 4,963,657 | A | * | 10/1990 | Pixley ..................... 530/388.25 |
| 5,723,439 | A | * | 3/1998 | Zhirnov et al. ............... 424/499 |
| 5,866,122 | A | | 2/1999 | Turecek et al. |
| 6,403,077 | B1 | | 6/2002 | Strom et al. |
| 6,583,108 | B1 | * | 6/2003 | Tamburini et al. ........... 514/13.7 |
| 6,613,890 | B2 | | 9/2003 | White et al. |
| 6,989,369 | B2 | * | 1/2006 | Ladner et al. ................. 514/1.5 |
| 7,939,632 | B2 | * | 5/2011 | Metzner et al. ............... 530/362 |
| 8,119,137 | B2 | * | 2/2012 | Nieswandt et al. ........ 424/145.1 |
| 2001/0020003 | A1 | * | 9/2001 | White et al. .................... 514/12 |
| 2003/0194398 | A1 | | 10/2003 | Tamburini et al. |
| 2004/0087778 | A1 | | 5/2004 | Feige et al. |
| 2008/0026998 | A1 | * | 1/2008 | Kisiel et al. ..................... 514/12 |
| 2009/0304685 | A1 | * | 12/2009 | Pritchard .................. 424/133.1 |

FOREIGN PATENT DOCUMENTS

| EP | 1867660 A1 | 12/2007 |
| WO | WO 91/17258 A1 | 11/1991 |
| WO | WO 01/79271 A1 | 10/2001 |
| WO | WO 03/076567 A2 | 9/2003 |
| WO | WO 2004/101740 A2 | 11/2004 |
| WO | WO 2005/000892 A2 | 1/2005 |
| WO | WO 2005/001025 A2 | 1/2005 |
| WO | WO 2005/024044 A2 | 3/2005 |
| WO | WO 2005/063808 A1 | 7/2005 |
| WO | WO 2006/000448 A2 | 1/2006 |
| WO | WO 2006/066878 A1 | 6/2006 |
| WO | WO 2007/072012 A1 | 6/2007 |
| WO | 2007/144173 A1 | 12/2007 |
| WO | WO 2008/098720 A1 | 8/2008 |
| WO | WO 2009/094641 A2 | 7/2009 |

OTHER PUBLICATIONS

Dempsey et al., QJM. Oct. 2006;99(10):643-54. Epub Sep. 6, 2006.*
Ansel et al., "Pharmaceutical dosage forms and drug delivery systems," 7th Edition, 1999, 2 pages.
Beattie et al., "Structure and evolution of human α-fetoprotein deduced from partial sequence of cloned cDNA," Gene, vol. 20, 1982, pp. 415-422.
Campos et al., "Identification and characterization of a novel factor XIIa inhibitor in the hematophagous insect, *Triatoma infestans* (Hemiptera: Reduviidae)," FEBS Letters, vol. 577, 2004, pp. 512-516.
Campos et al., "Infestin, a thrombin inhibitor presents in *Triatoma infestans* midgut, a Chagas' disease vector: gene cloning, expression and characterization of the inhibitor," Insect Biochemistry and Molecular Biology, vol. 32, 2002, pp. 991-997, XP-002446470.
Chen et al., "Inhibition of plant-pathogenic fungi by a corn trypsin inhibitor overexpressed in *Escherichia coli*," Applied and Environmental Microbiology, vol. 65, No. 3, Mar. 1999, pp. 1320-1324.
Communication for European Application No. 10003652.4, dated Sep. 25, 2012.
Cooke et al., "Serum vitamin D-binding protein is a third member of the albumin and alpha fetoprotein gene family," J. Clin. Invest., vol. 76, Dec. 1985, pp. 2420-2424.

(Continued)

*Primary Examiner* — Michael Szperka
(74) *Attorney, Agent, or Firm* — Birch, Stewart, Kolasch & Birch, LLP

(57) ABSTRACT

The present invention provides methods for treating interstitial lung diseases, comprising administering to an individual an effective amount of an inhibitor of coagulation factor XII. The invention further provides uses and pharmaceutical kits for that treatment.

24 Claims, 34 Drawing Sheets

(56) References Cited

OTHER PUBLICATIONS

Extended European Search Report for European Application No. 10003652.4, dated Jan. 28, 2011.
Frokjaer et al., "Pharmaceutical formulation development of peptides and proteins," European Journal of Pharmaceutics and Biopharmaceutics, vol. 50, 2000, pp. 329.
Gennaro, "Remington: The Science and Practice of Pharmacy," Lippincott Williams and Wilkins, 20th Edition, Dec. 2000, 4 pages.
International Search Report and Written Opinion of the International Searching Authority (PCT Forms PCT/ISA/220, PCT/ISA/210 and PCT/ISA/237) for International Application No. PCT/EP2011/055128, dated Aug. 4, 2011.
Isawa et al., "A mosquito salivary protein inhibits activation of the plasma contact system by binding to factor XII and high molecular weight kininogen," The Journal of Biological Chemistry, vol. 277, No. 31, Aug. 2, 2002, pp. 27651-27658.
Jablonska et al., "Factor XII is a novel mitogenic factor for lung fibroblasts in lung fibrosis," Journal of Thrombosis and Haemostasis, AS-TH-037, vol. 7, Suppl. 2, Jul. 1, 2009, p. 92, XP009149430.
Jablonska, "Inhibition of FXIIa or knockout of FXII protects against lung fibrosis," Role of intrinsic coagulation pathway in the pathogenesis of idiopathic pulmonary fibrosis, VVB Laufersweiler Verlag, 1st Edition, 2010, pp. 60-62 (108 pages provided), XP-002643103.
Jin et al., "Crystal structures of the FXIa catalytic domain in complex with ecotin mutants reveal substrate-like interactions," The Journal of Biological Chemistry, vol. 280, No. 6, Feb. 11, 2005, pp. 4704-4712.
Kannemeier et al., "Extracellular RNA constitutes a natural procoagulant cofactor in blood coagulation," PNAS, vol. 104, No. 15, Apr. 10, 2007, pp. 6388-6393.
Kibbe, "Handbook of pharmaceutical excipients," Pharmaceutical Press, Third Edition, London, 2000, p. 665, In: Book Reviews, Journal of Controlled Release, vol. 71, 2001, pp. 351-353.
Laskowski, Jr. et al., "Protein inhibitors of proteinases," Ann. Rev. Biochem., vol. 49, 1980, pp. 593-626.
Lichenstein et al., "Afamin is a new member of the albumin, α-fetoprotein, and vitamin D-binding protein gene family," The Journal of Biological Chemistry, vol. 269, No. 27, Jul. 8, 1994, pp. 18149-18154.
Partial European Search Report for European Application No. 10003652.4, dated Sep. 29, 2010.
Tani et al., "Thrombin enhances lung fibroblast proliferation in bleomycin-induced pulmonary fibrosis," Am. J. Respir. Cell Mol. Biol., vol. 5, Jul. 1991, pp. 34-40, XP009138698.
Wen et al., "Nucleotide sequence of a cDNA clone that encodes the maize inhibitor of trypsin and activated Hageman factor," Plant Molecular Biology, vol. 18, 1992, pp. 813-814.
Werle et at, "Strategies to improve plasma half life time of peptide and protein drugs," Amino Acids, vol. 30, 2006, pp. 351-367.
Williams et al., "DX-88 and HAE: a developmental perspective," Transfusion and Apheresis Science, vol. 29, 2003, pp. 255-258.
European Office Action dated Jun. 17, 2014, issued in corresponding European Patent Application No. 10 003 652.4.
European Office Action dated Jun. 17, 2014, issued in corresponding European Patent Application No. 11 711 598.0.
Rongqi Wang et al.; "Abrogation of bleomycin-induced epithelial apoptosis and lung fibrosis by captopril or by a caspase inhibitor"; American Journal of Physiology. Lung cellular and molecular physiology; vol. 279; No. 1 23-1; Jan. 1, 2000; pp. L143-L151.
English Translation of Japanese Notice of Reasons for Rejection for Application No. 2013-501866 dated Mar. 24, 2015.
Tani et al., Japanese Journal of Thoracic Diseases, 1991, vol. 29, No. 2, pp. 211-219 with English language abstract.

* cited by examiner

E

FACTOR XII INHIBITORS FOR TREATING INTERSTITIAL LUNG DISEASE

CROSS REFERENCE TO RELATED APPLICATIONS

This application is the National Phase of PCT/EP2011/055128 filed on Apr. 1, 2011, which claims priority under 35 U.S.C. 119(e) to U.S. Provisional Application No. 61/282,801 filed on Apr. 1, 2010 and under 35 U.S.C. 119(a) to Patent Application No. 10003652.4 filed in European Patent Office on Apr. 1, 2010, all of which are hereby expressly incorporated by reference into the present application.

The present invention relates to the use of non-endogenous inhibitors of the cellular activity of factor XII and/or factor XIIa for treating and/or preventing fibroproliferative interstitial lung diseases such as idiopathic pulmonary fibrosis.

BACKGROUND OF THE INVENTION

Interstitial lung disease (ILD), also known as diffuse parenchymal lung disease (DPLD), refers to a group of lung diseases affecting the interstitium (the tissue and space around the air sacs of the lungs). It concerns alveolar epithelium, pulmonary capillary endothelium, basement membrane, perivascular and perilymphatic tissues. Idiopathic pulmonary fibrosis (IPF) is defined as a distinctive type of chronic fibrosing interstitial pneumonia of unknown cause limited to the lungs and associated with a histological pattern of usual interstitial pneumonia (UIP). IPF lungs are characterized by architectural destruction, dense scarring with honeycombing and scattered fibroblasts foci (areas of intensive fibroblasts proliferation). IPF has a progressive and usually fatal course with a medium survival of 2-3 years following diagnosis. Patients with IPF are usually between 50 to 70 years old and the incidence is 7.4 cases per 100,000 for women and 10.7 cases per 100,000 for men per year. The incidence, prevalence and death increase with age. To date, most treatment strategies have been based on eliminating or suppressing the inflammatory component. No pharmacological therapy has been proven to be effective in IPF treatment. All currently available therapeutic trials in IPF are severely limited by the lack of clear understanding of the disease etiology. The original hypothesis of the pathogenesis of IPF is that chronic inflammation in response to unknown etiological agents (idiopathic) leads to tissue destruction, initiation and propagation of wound healing responses and, subsequently, to progressive fibrosis. A recent proposal indicates that inflammation is necessary to trigger the initiation of the fibrotic process, but plays a minor role in the progression of the disease. In contrast to other forms of chronic interstitial lung diseases such as sarcoidosis and hypersensitivity pneumonitis, IPF is characterized by only limited inflammation.

Recently, it has been suggested that IPF is mainly a disorder of alveolar epithelial injury, abnormal alveolar wound repair and remodelling.

Transforming growth factor-β1 (TGF-β1) is a highly pleiotropic cytokine which plays a fundamental role in wound healing, embryonic development and disease states associated with inflammation and proliferation, for example tissue fibrosis. In the adult mice, TGF-β overexpression in the lungs leads to progressive pulmonary fibrosis. TGF-β is thought to promote fibrotic responses in the lungs mainly due to suppression of alveolar epithelial cell proliferation, stimulation of fibroblasts proliferation, activation of resident lung cells including epithelial cells, which differentiate into collagen-producing myofibroblasts. TGF-β1 enhances synthesis and inhibits degradation of extracellular matrix components. Moreover, recent studies suggest that TGF-β1 may contribute to fibrotic conditions by modulating procoagulant and fibrinolytic activities. In particular, TGF-β1 has been shown to upregulate the expression of tissue factor, the key initiator of the extrinsic coagulation pathway, and of the plasminogen activator inhibitor (PAI)-1 in different cell populations including fibroblasts.

The cellular response to TGF-β1 involves ligand binding to TGF-β receptor type II (TβR-II) which phosphorylates TGF-β receptor type I (TβR-I). Activated TβR-I phosphorylates receptor associated Smads (Smad 1, 2, 3, 5, and 8), promoting their heterodimerization with common-mediator Smad (Smad 4) and translocation from the cytoplasm to the nucleus. Within the nucleus, the Smad hetero-complex interacts with canonical smad-binding elements (SBEs) of target genes to activate their transcription. Human Smad 3 and Smad 4 have been shown to bind to SBE comprising CAGA box.

Alterations of the alveolar haemostatic balance and excessive deposition of intraalveolar fibrin have been observed in the lungs of IPF patients. Intraalveolar fibrin accumulation, observed under these conditions, arises from the imbalance between locally produced pro- and anti-coagulant factors, in combination with leakage of plasma proteins (including fibrinogen) into the alveolar space. Increased procoagulant activity in bronchoalveolar lavage (BAL) fluids of patients with IPF is accompanied by a decreased fibrinolytic activity. Identical alterations of the haemostatic balance in the alveolar space have been observed in the bleomycin animal model of pulmonary fibrosis. In clinical and experimental lung fibrosis the procoagulant response is mainly attributable to tissue factor (TF) associated with factor VIIa, whereas the decreased fibrinolytic activity is ascribed to inhibition of urokinase type (u-PA) and tissue type (t-PA) plasminogen activators by plasminogen activator inhibitor (PAI)-1 as well as blockage of plasmin by α2-plasmin inhibitor. Although fibrin is required for reparative processes and normal wound healing, persistent and excessive deposition of extravascular fibrin is thought to contribute to the pathomechanisms of fibrotic lung diseases in several ways. Fibrin may serve as a reservoir of profibrotic growth factors. It incorporates and inactivates pulmonary surfactant, the lung lipoprotein complex critical for maintaining low alveolar surface tension. Surfactant dysfunction leads to atelectasis and loss of lung compliance. Moreover, inactivation of the surfactant system, in conjunction with "glueing" of the adjacent alveolar walls by fibrin, is thought to provide a provisional matrix on which fibroblasts proliferate and produce collagen.

In addition, the u-PA/PAI-1 system may contribute to development of lung fibrosis by regulation of cell migration, cell adhesion and cell proliferation. Furthermore, various coagulation proteases such as thrombin, factor Xa and the TF/factor-VIIa complex exhibit cellular activities that may also contribute to fibrotic processes in the lung. Most of these functions are mediated via proteolytic activation of protease activated receptors (PARs). For instance, thrombin and factor Xa stimulate fibroblast proliferation and procollagen production in a PAR-1-dependent manner. Additionally, thrombin induces differentiation of normal lung fibroblasts to myofibroblasts via PAR-1 activation. Furthermore, activation of PAR-1 by thrombin, factor Xa and by the TF/factor VIIa complex can increase the expression of profibrotic and proinflammatory cytokines. A potential role of PAR-1 in pulmonary fibrosis is underscored by the recent finding demonstrating that PAR-1-deficient mice are protected against bleomycin-induced lung fibrosis. Additional evidence under-lying the importance of cellular effects mediated by haemostatic factors in the development of lung fibrosis came from the recent observation indicating no protection against bleomycin-induced lung fibrosis in fibrinogen-null mice.

SUMMARY OF THE INVENTION

The inventors surprisingly found that factor XII (FXII) plays a role during the fibrotic phases of experimentally induced lung injury. In addition, it was observed that FXII-dependent induction of lung fibroblast proliferation was attenuated by pharmacological blockade of the ERK1/2 pathway and by FXIIa-specific inhibition.

These results place FXII/FXIIa in a central position in the pathology of pulmonary fibrosis. Hence substances capable of interfering and blocking FXII activation or FXIIa activity may be suited to block fibrotic processes in lungs and the clinical consequences thereof i.e. such substances may be suitable to limit lung fibroplast proliferation by specifically inhibiting the cellular activity of FXII/FXIIa.

In a first aspect, the present invention relates to a non-endogenous inhibitor of the cellular activity of factor XII and/or factor XIIa (FXII/FXIIa) for treating and/or preventing a fibroproliferative interstitial lung disease such as idiopathic pulmonary fibrosis.

A second aspect of the invention is a method of treating and/or preventing fibroproliferative interstitial lung diseases such as idiopathic pulmonary fibrosis, said method comprising administering to an individual a pharmaceutically effective amount of a non-endogenous inhibitor of the cellular activity of FXII and/or FXIIa.

In a special aspect of the invention the treatment comprises combination treatment with a second therapeutic agent or therapeutic principle to treat interstitial lung disease. Said second therapeutic principle may be oxygen therapy. Said second therapeutic agent for the treatment of interstitial lung disease may be a corticosteroid drug, azathioprine, pirfenidone, cyclophosphamide, acetylcysteine and/or anti-fibrotics.

A further aspect of the present invention is a method of prolonging the survival time of a patient suffering from a fibroproliferative interstitial lung disease, said method comprising administering to said patient a pharmaceutically effective amount of a non-endogenous inhibitor of the cellular activity of FXII and/or FXIIa.

Yet another aspect of this invention is a method of reducing the symptoms associated with fibroproliferative interstitial lung diseases such as idiopathic pulmonary fibrosis, said method comprising administering to a patient a pharmaceutically effective amount of a non-endogenous inhibitor of the cellular activity of FXII and/or FXIIa.

Yet another aspect of this invention is a pharmaceutical kit for treating and/or preventing fibroproliferative interstitial lung disease such as idiopathic pulmonary fibrosis, said kit comprising (1) a non-endogenous inhibitor of the cellular activity of FXII and/or FXIIa and (2) a further drug for treating interstitial lung disease. Said further drug may be selected from the group consisting of corticostereoid drugs, azathioprine, pirfenidone, cyclophosphamide, acetylcysteine and anti-fibrotics.

DETAILED DESCRIPTION OF THE INVENTION

Figure 1:
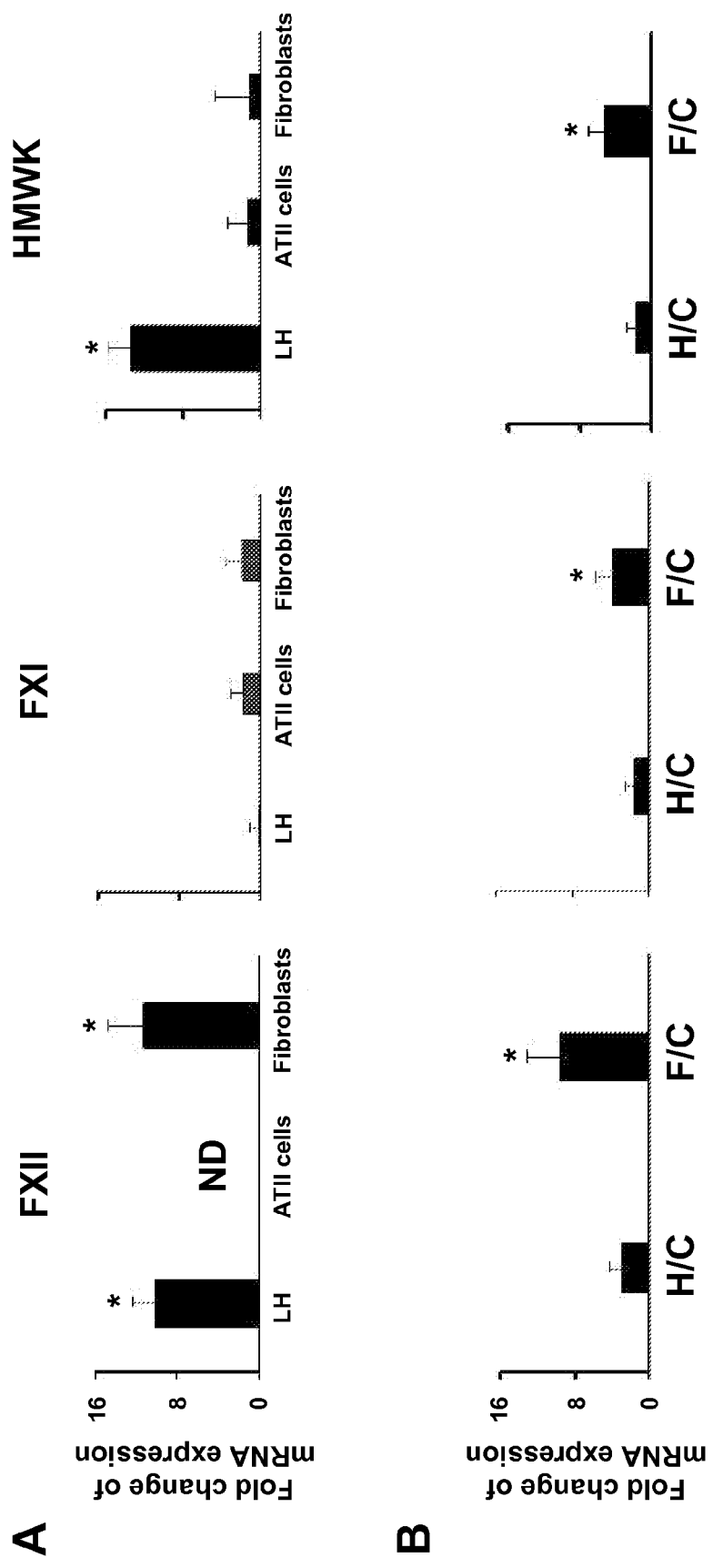
FIG. 1: mRNA level of FXII, FXI and HMWK is elevated in lungs of IPF patients. (A) The expression of FXII, FXI and HMWK mRNA was assessed in donor and IPF lung tissue homogenates (LH) as well as in lung fibroblasts and alveolar epithelial type II cells (AT II) isolated from donor (n=10) and IPF (n=10) lungs by RT-PCR. Given is the fold-increase in mRNA expression in IPF specimens (normalized for β-actin expression) versus values obtained for donor samples. (B) Expression of FXII, FXI and HMWK in healthy (H) and fibrotic (F) regions of IPF lungs. Given is the fold-increase in mRNA expression in IPF specimens (normalized for β-actin expression) versus values obtained for donor samples (C). Results are presented as mean±s.e.m., *p<0.05; Student's t-test. ND; not detected

The invention relates to methods for treating and/or preventing interstitial lung disease, comprising administering to a subject a pharmaceutically effective amount of a non-endogenous inhibitor of the cellular activity of FXII/FXIIa i.e. administering such an inhibitor prevents and/or limits the proliferation of lung fibroblast cells. Likewise, the invention pertains to the use of a non-endogenous cellular FXII inhibitor for the manufacture of a medicament for treating and/or preventing interstitial lung disease.

Factor XII

FXII is a polypeptide produced in the liver as a single chain 78kD zymogen. Upon activation FXII is converted into a two chain form consisting of a heavy and a light chain. The heavy chain contains the following domains: leader peptide, fibronectin type II domain, the epidermal growth factor (EGF) domain, fibronectin type I domain, the kringle domain, and the proline-rich domain, which is unique for FXII. The light chain contains the catalytic domain typical for serine proteases, whereby FXII has a similar domain organization as other members of the serine protease family such as tissue-type plasminogen activator (t-PA), urokinase-type plasminogen activator (u-PA), or Factor VII-activating protease. The heavy chain contains binding regions for negatively-charged surfaces localized at the amino terminus, along the fibronectin type I region, and possibly localized at the second EGF-like domain or kringle domain. The active site of FXII in the light chain consists of the canonical catalytic triad including His40, Asp89 and Ser191 residues. This site is also a target for major intrinsic coagulation pathway inhibitor, C1 inhibitor. Cleavage of FXII by kallikrein or its autoactivation, result in the splitting of the Arg353-Val354 bound in the FXII zymogen, leading to the generation of the active alphaXIIa form, which contains heavy and light chain linked by a disulfide bond. Hydrolysis of two additional peptide bonds in alphaXIIa form generates 30kD betaXIIa, containing the light chain and a truncated fragment of the heavy chain. AlphaXIIa is able to bind to negatively charged surfaces and activate FXI and prekallikrein (PK). BetaXIIa has no surface-binding ability but can activate PK.

As used herein, the term "factor XII" or "FXII" refers to any of the above-described forms of factor XII. In particular, the term includes the activated form factor XIIa (FXIIa).

Interstitial Lung Disease

Interstitial lung disease (ILD) also known as diffuse parenchymal lung disease (DPLD), refers to a group of lung diseases affecting the interstitium (the tissue and space around the air sacs of the lungs). It concerns alveolar epithelium, pulmonary capillary endothelium, basement membrane, perivascular and perilymphatic tissues. The ILD in the sense of the present application particularly relates to lung fibroblast proliferation and therefore the term "fibroproliferative ILD" is used. This lung fibroblast proliferation should be treated and/or prevented by the present invention.

Preferably, the ILD to be treated in accordance with this invention is pulmonary fibrosis. Most preferably, the pulmonary fibrosis is idiopathic pulmonary fibrosis. Idiopathic pulmonary fibrosis (IPF) is defined as a distinctive type of chronic fibrosing interstitial pneumonia of unknown cause limited to the lungs and associated with a histological pattern of usual interstitial pneumonia (UIP). IPF lungs are characterized by architectural destruction, dense scarring with honeycombing and scattered fibroblasts foci (areas of intensive fibroblasts proliferation).

Non-endogenous Inhibitors of the Cellular Activity of FXII

The term "non-endogenous inhibitor of the cellular activity of FXII" or "non-endogenous cellular FXII inhibitor" refers to any non-endogenous compound capable of reducing the cellular activity of FXII and/or FXIIa or its amount. FXII inhibitors in the sense of the present invention include compounds which interfere with the catalytic activity of FXIIa. Further included are compounds capable of reducing the amount of FXII or FXIIa in vivo. Such inhibitors include compounds which are capable of reducing the expression of FXII. Further, included are inhibitors which interfere with the conversion of FXII into FXIIa.

Such inhibitors reduce the biological function of FXII and/or FXIIa to at least 50%, preferably to at least 75%, more preferred to at least 90% and even more preferred to at least 95% such as at least 98% or even at least 99%. Biological function denotes any known cellular effect of FXII/FXIIa. Examples of said cellular function are the proliferative and/or mitogen effect on cells, in particular lung fibroblasts or smooth muscle cells.

A "non-endogenous" inhibitor in the sense of the invention is a FXII/FXIIa inhibitor not naturally occurring in the species in which the FXII/FXIIa should be inhibited. Endogenous inhibitors of FXII/FXIIa are e.g. antithrombin, C1 inhibitor, alpha-1 protease inhibitor. Non-endogenous FXII/FXIIa inhibitors of the invention are much more specific than endogenous FXII/FXIIa inhibitors, i.e. the inhibitor according to the present invention is very specific for FXII/FXIIa. This specificity can be expressed e.g. as the molar ratio of the specific inhibitor to FXII/FXIIa which is needed to obtain a reduction of 50% of the activity of FXII/FXIIa. This is called the molar inhibitory ratio in the sense of the invention. A molar inhibitory ratio of 0.5 means that 0.5 pmol of inhibitor added to 1 pmol of FXII/FXIIa leads to a 50% reduction of the activity of FXII/FXIIa. Specific, i.e. non-endogenous inhibitors of the invention are inhibitors having a molar inhibitory ratio of less or equal than 10, or preferred less or equal than 5 or more preferred less or equal than 2 or even more preferred less or equal than 1 such as less or equal than 0.5.

A test for determining the catalytic activity of FXIIa is described in Kannemeier C, Shibamiya A, Nakazawa F, Trusheim H, Ruppert C, Markart P, Song Y, Tzima E, Kennerknecht E, Niepmann M, Bruehl M L, Sedding D, Massberg S, Gunther A, Engelmann B, Preissner K T. Extracellular RNA constitutes a natural procoagulant cofactor in blood coagulation. Proc Natl Acad Sci USA. 104:6388-6393, 2007. Briefly, the FXIIa-sample and a chromogenic substrate peptide is mixed, and the release of p-nitroanilin is followed over time in a photometer at 405 nm. A compound is suitable as an inhibitor of the catalytic, in particular the enzymatic activity of FXIIa if it is capable of reducing the catalytic activity in that assay in a significant manner, preferably by at least 10%, more preferably by at least 25%, most preferably by at least 50% such as at least 75% or even at least 90%.

A test for determining the degree of conversion of FXII into FXIIa is described in a similar way as described above by following the increase of FXIIa in a chromogenic peptide assay, A compound is suitable as an inhibitor interfering with the conversion of FXII into FXIIa if the compound is capable of inhibiting this conversion to a significant extent according to that assay; preferably, the reduction in conversion affected by the inhibitor is at least 10%, more preferably at least 25%, most preferably at least 50%.

Methods of determining the amount of FXII and/or FXIIa are described in which the total amount of FXII/FXIIa is quantitated by a Enzyme-linked Immunosorbent Assay (ELISA) using FXII-specific antibodies, and the portion of activated FXII is determined by analysing the sample by SDS-polyacrylamid gelelectrophoresis, followed by Western-blotting to quantitate the protein banding pattern. Such methods include known methods of protein detection such as ELISA and other immunological techniques.

Anti-FXII Antibodies

Antibodies directed against FXII and/or FXIIa may be used to inhibit the function of FXIIa. Such antibodies include, e.g., anti-FXII antibodies, include poly- and monoclonal antibodies.

The antibody may also be a fragment of same or mimetic retaining the inhibitory activity, for example analogues of Kunitz Protease Inhibitor domain of amyloid precursor protein as disclosed in U.S. Pat. No. 6,613,890 especially in columns 4 through 8.

Protease Inhibitors

An efficient way to inhibit FXIIa activity is the use of specific, non-endogenous protease inhibitors such as serine protease inhibitors. Examples include aprotinin, Z-Pro-Pro-aldehyde-dimethyl acetate, DX88 (Dyax Inc., 300 Technology Square, Cambridge, Mass. 02139, USA; cited in: Williams A. and Baird LG., Transfus Apheresis Sci. 2003 Dec. 29 (3):255-8), inhibitors of prolyl oligopeptidase such as Fmoc-Ala-Pyr-CN, Corn-Trypsin Inhibitor (CTI), mutants of the bovine pancreatic trypsin inhibitor and Pro-Phe-Arg-chloromethyl-ketone (PCK).

Other suitable inhibitors may be Hamadarin as disclosed by H. Isawa et al. (J Biol Chem 277:27651-27658, 2002). A suitable Corn Trypsin Inhibitor and methods of its production are disclosed in Z. Y. Chen et al. (Appl Environm Microbiol 65:1320-1324, 1999 and reference 19 cited ibidem). All references cited are incorporated for reference including their entire content in this application. Last but not least, small molecules isolated for example via use of FXII respective FXIIa inhibition as the assay on which selection is based are part of the invention, as well as their respective use described above or below. These small molecule FXIIa inhibitors could be designed on the basis of a crystal structure of FXII. Therefore, several FXII domains or the light chain could be expressed recombinantly in expression systems such as $E. coli$, yeast or mammalian cells. Then the protein is purified and crystallized using standard procedures as described for the FXII substrate FXI (Jin L et al. J Biol Chem. 280:4704-4712, 2005). Crystal structures of the FXIa catalytic domain in complex with ecotin mutants reveal substrate-like interactions. Alternatively, small molecule serine protease inhibitors could be included to stabilize the FXII structure.

Recently, a novel inhibitor of FXII/FXIIa was discovered in insects: Infestin domains 3-4 (Infestin 3-4) and Infestin domain 4 (Infestin-4) from the midgut of *Triatoma infestans*, a hematophagous insect (Campos ITN et al. 2002. Infestin, a thrombin inhibitor present in *Triatoma infestans* midgut, a Chagas' disease vector: gene cloning, expression and characterization of the inhibitor. Insect Biochem. Mol. Biol. 32:991-997; Campos ITN et al. 2004. Identification and characterization of a novel factor XIIa inhibitor in the hematophagous insect, *Triatoma infestans* (Hemiptera: Reduviidae). FEBS Lett. 577:512-516). These proteins are known as potent FXIIa inhibitors of the Kazal-type serine protease inhibitors, prolonging activated partial thromboplastin time approximately three-fold.

In the international patent application WO 2008/098720 use of Infestin 3-4 and Infestin-4 as well as an albumin fusion protein of Infestin 4 (rHA-Infestin-4) as potent inhibor of FXIIa are described as well as these molecules per se. Furthermore, a human protein with a very high similarity to Infestin-4 was described to be SPINK-1, Kazal-type serine protease inhibitor expressed in the pancreas (also known as pancreatic secretory trypsin inhibitor, PSTI). Based on the wild-type SPINK-1 sequence, three different mutants have been described with increased homology of the SPINK-1 sequence to Infestin-4. The amino acid sequences of the mature SPINK-1 wild-type protein, the three mutants and Infestin-4 are given as SEQ ID NO 29 to 33. In an embodiment the FXII inhibitor of the invention comprises mutant Kazal inhibitors derived from SPINK-1 wherein the inhibitor has an increased homology to Infestin-4. The term "SPINK-1 mutants with increasing respective increased homology" refers to mutants containing more than 20 identical amino acids with Infestin-4, or a conservative substitution instead of identity meaning a conservative substitution instead of an identical amino acid. Preferably the contact sites of said mutant Kazal inhibitors with the inhibited FXIIa are derived from domain 4 of Kazal-type inhibitor Infestin. The entire description of WO 2008/098720 is hereby incorporated by reference in this application.

Therefore infestin or a fragment thereof, or Infestin 3-4 or Infestin-4, or said mutant Kazal inhibitors derived from SPINK-1, wherein, the inhibitor has an increased homology to Infestin-4, and fusion proteins rHA-Infestin-4 as described below are suitable non-endogenous inhibitors of cellular activity of FXII/FXIIa according to the present invention.

In other words in one embodiment, the application provides a FXII inhibitor comprising Infestin domain 4, Infestin-4. In one embodiment, a FXII inhibitor comprises a variant of Infestin-4. In another embodiment, FXII inhibitors comprise Infestin domain 4, and optionally Infestin domains 1, 2, and/or 3; these proteins are known to be potent inhibitors of FXII. The wild type polypeptide sequence of Infestin-4 is provided (SEQ ID NO: 33). As used herein, the term "variant" refers to a polypeptide with an amino acid mutation, wherein a "mutation" is defined as a substitution, a deletion, or an addition, to the wild type Infestin-4 sequence, wherein such changes do not alter the functional ability of the polypeptide to inhibit FXII. The term "variant" includes fragments of the wild type or mutated Infestin-4 sequence. Further examples of such variants are provided below.

In one embodiment, an Infestin-4 variant comprises the N-terminal amino acids 2-13 of the wild type Infestin-4 sequence, and at least one and up to five amino acid mutations outside the N-terminal amino acids that result in differences from the wild type Infestin-4 sequence, or six conserved cysteine residues and homology of at least 70% to the wild type Infestin-4 sequence. The N-terminal amino acids 2-13 of the Infestin-4 sequence may be important for binding to FXII based on analysis of structural data for a related inhibitor *Rhodnius prolixus* (PDB: 1 TSO) binding to thrombin, and analysis of SPINK-1 binding to chymotrypsin, which both share a common feature of the accumulation of contact sites in the N-terminal region. Therefore in one embodiment, a variant of Infestin-4 comprises the conserved N-terminal region of amino acids 2-13 of the wild type Infestin-4 sequence, and at least one and up to five amino acid mutations outside these conserved N-terminal amino acids that result in differences from the wild type Infestin-4 sequence. A mutation may be a substitution, a deletion, or an addition. As used herein, the term "outside said N-terminal amino acids" refers to any amino acid along the polypeptide chain of the variant other than the contiguous stretch of amino acids that comprises the sequence VRNPCACFRNYV, i.e., amino acids 2-13 from the wild type Infestin-4 sequence (SEQ ID NO: 33). In another embodiment, an Infestin-4 variant comprises six conserved cysteine residues and has homology of at least 70% to the wild type Infestin-4 sequence. In one embodiment, the six conserved cysteine residues are amino acids at positions 6, 8, 16, 27, 31, and 48 of the wild type Infestin-4 sequence. In one embodiment, the variant comprises the final conserved cysteine. In other embodiments, the exact positions of the cysteine residues, and relative positions to each other, may change from positions 6, 8, 16, 27, 31, and 48 of the wild type Infestin-4 sequence due to insertions or deletions in the Infestin-4 variant. Nevertheless, in these embodiments, an Infestin-4 variant comprises all six cysteines and may share 70%, 75%, 85%, 90%, 91%, 92%, 93%, 94%, 95%, 96%, 97%, 98% or 99% homology to the wild type Infestin-4 sequence.

In embodiments, a variant of Infestin-4 is characterized in that it inhibits FXII. The functional activity of inhibiting FXII may be assessed for example, through in vitro and/or in vivo characterization, including direct assays to test inhibition of FXII enzyme activity, prolonged coagulation time, i.e. activated partial thromboplastin time (aPTT), or in vivo methods that evaluate coagulation. Further examples of Infestin-4 variants are SPINK-1 mutants, which are described below.

Figure 12:
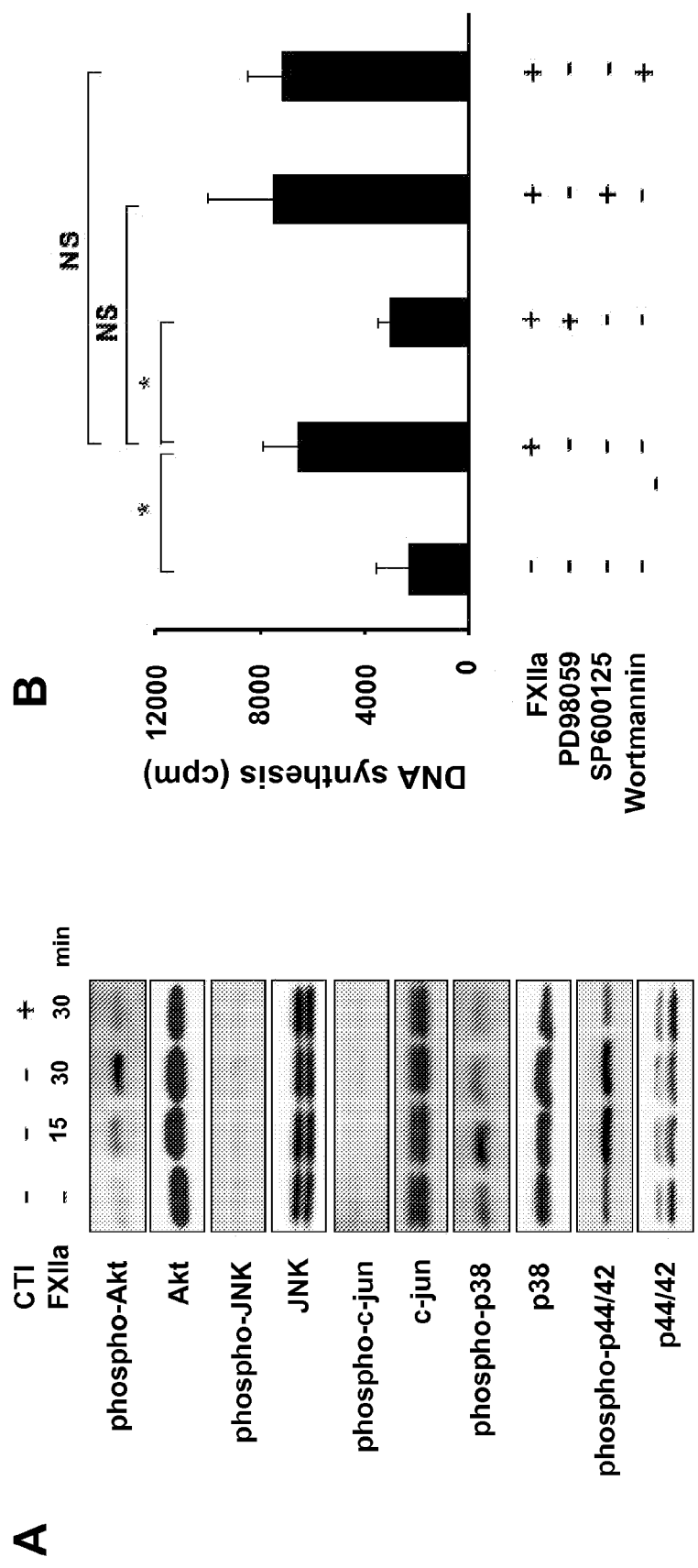
FIG. 12: p44/42 kinase regulates FXII-induced proliferation of murine lung fibroblasts. (A) Murine lung fibroblasts were treated for the indicated time points with FXIIa and the activity and expression of p44/42, JNK, c-jun, p38 and Akt kinases were analyzed by Western blotting. Phosphoproteins were detected via phospho-specific antibodies as indicated. Equal loading was confirmed via pan-specific antibodies. Data are representative of three independent experiments. (B) [$^3$H]-thymidine incorporation in murine lung fibroblasts pretreated with specific inhibitors of JNK, PI3K, MEK and p38 kinases (SP600125, Wortmannin, PD98059, and SB203580, respectively) prior to FXIIa stimulation. The values are presented as the mean±SEM of four determinations performed within one experiment of at least three; *P<0.05; ANOVA, Tukey's post test.

One embodiment involves FXII inhibitors for therapeutic use in humans. A human protein with high similarity to Infestin-4 may be employed. For example, the human protein with the highest similarity to Infestin-4 is SPINK-1, a Kazal-type serine protease inhibitor expressed in the pancreas (also known as pancreatic secretory trypsin inhibitor, PSTI). The Kazal-type serine protease inhibitor family is one of numerous families of serine protease inhibitors. Many proteins from different species have been described (Laskowski M and Kato I, 49 *Ann. Rev. Biochem.* 593-626, 1980). The amino acid sequence similarities between Infestin-4 and SPINK-1 are outlined in FIG. 12.

Based on the wild-type SPINK-1 sequence (SEQ ID NO: 29) different variants may be generated in order to increase homology of the SPINK-1 sequence to Infestin-4. The phrase "increased homology to Infestin-4" refers to the process whereby amino acid mutations are made to SPINK-1 to bring the SPINK-1 sequence closer to the Infestin-4 sequence.

In one embodiment, SPINK-1 is mutated to comprise the N-terminal amino acids 2-13 of the wildtype Infestin-4 sequence; the polypeptide sequence is given and is referred to as K1 (SEQ ID NO: 30). As described above, the N-terminal portion of the Infesin-4 sequence is thought to be important for FXII inhibitory function.

Therefore, in one embodiment, a variant of the mutated SPINK-1 also comprises N-terminal amino acids 2-13 of the wildtype Infestin-4 sequence, and at least one and up to five amino acid mutations outside said N-terminal amino acids that result in differences from the wildtype SPINK-1 sequence and which increase the homology of the variant to the wildtype Infestin-4 sequence. In another embodiment, a variant of mutated SPINK-1 comprises six conserved cysteine residues and has homology of at least 70% to the wildtype SPINK-1 sequence. A mutation may be a substitution, a deletion, or an addition. As defined above, the term "outside said N-terminal amino acids" refers to any amino acid along the polypeptide chain of the variant other than the contiguous stretch of amino acids that is comprised of the sequence VRNPCACFRNYV, i.e., amino acids 2-13 from the wildtype Infestin-4 sequence (SEQ ID NO: 33). The term "variant" includes fragments of said mutated SPINK-1 sequence. In one embodiment, the six conserved cysteine residues may be amino acids at positions 9, 16, 24, 35, 38, and 56 of the wildtype SPINK-1 sequence. In one embodiment, the variant comprises the final conserved cysteine. In another embodiment, the exact positions of the cysteines, and relative positions to each other, may change from positions 9, 16, 24, 35, 38, and 56 of the wild type SPINK-1 sequence due to insertions or deletions in the SPINK-1 variant. Nevertheless, in these embodiments, a SPINK-1 variant comprises all six cysteines. In embodiments, a SPINK-1 variant is also characterized in that it inhibits FXII.

Examples of such SPINK-1 variants are given and are named K2, and K3 (SEQ ID NO: 31 and 32 respectively). In SPINK-1 variants K2 and K3, further amino acid substitutions outside the N-terminus were made in order to increase homology to Infestin-4, wherein the variants are also characterized in that they inhibit FXII activity. See WO 2008/098720. In the case of the SPINK-1 variant K3, five amino acid substitutions were made to increase homology to Infestin-4. Thus in embodiments, a SPINK-1 variant may share 70%, 75%, 85%, 90%, 91%, 92%, 93%, 94%, 95%, 96%, 97%, 98% or 99% homology with the wildtype SPINK-1 sequence.

Inhibitors with Extended Half-Lives

A preferred embodiment of the present invention is the use of FXII/FXIIa inhibitors in particular Infestin-4 and modified mammalian Kazal-type serine protease inhibitors based on Infestin homologs or fragments thereof with extended half-life. As the Kazal-type serine protease inhibitors are rather small proteins, a rapid renal clearance as published for other small proteins can be expected (Werle M. and Bernkop-Schnurch A. 2006. Strategies to improve plasma half-life time of peptide and protein drugs. Amino Acids 30:351-367). One way to overcome a short plasma half-life of a polypeptidic compound is to inject it repeatedly or via continuous infusion. Preferably the intrinsic plasma half-life of the polypeptide itself is increased. It is therefore preferred to use FXII inhibitors in particular serine protease inhibitors fused to half-life extending proteins (HLEP).

A HLEP as used herein is selected from the group consisting of albumin, a member of the albumin-family, the constant region of immunoglobulin G and fragments thereof and polypeptides capable of binding under physiological conditions to albumin, to members of the albumin family as well as to portions of an immunoglobulin constant region. As specific examples, albumin and immunoglobulins and their fragments or derivatives have been described as HLEP.

Ballance et al. (WO 01/79271) described fusion polypeptides of a multitude of different therapeutic polypeptides which, when fused to human serum albumin, are predicted to have an increased functional half-life in vivo and extended shelf-life. The therapeutic protein may be fused directly or via a peptidic linker to the albumin moiety, and C- and N-terminal fusions are described.

The terms human serum albumin (HSA) and human albumin (HA) are used interchangeably in this application. The terms "albumin" and "serum albumin" are broader, and encompass human serum albumin (and fragments and variants thereof) as well as albumin from other species (and fragments and variants thereof).

As used herein, "albumin" refers collectively to an albumin polypeptide or amino acid sequence, or an albumin fragment or variant, having one or more functional activities (e.g. biological activities) of albumin. In particular, "albumin" refers to human albumin or fragments thereof, especially the mature form of human albumin as shown in SEQ ID No:34 herein or albumin from other vertebrates or fragments thereof, or analogs or variants of these molecules or fragments thereof.

The albumin portion of the albumin fusion proteins may comprise the full length of the HA sequence as described above, or may include one or more fragments thereof that are capable of stabilizing or prolonging the therapeutic activity. Such fragments may be of 10 or more amino acids in length or may include about 15, 20, 25, 30, 50, or more contiguous amino acids from the HA sequence or may include part or all of specific domains of HA.

The albumin portion of the albumin fusion proteins which can be used according to the invention may be a variant of normal HA. The therapeutic polypeptide portion of the fusion proteins of the invention may also be variants of the corresponding therapeutic polypeptides as described herein. The term "variants" includes insertions, deletions and substitutions, either conservative or non-conservative, where such changes do not substantially alter the active site, or active domain, which confers the therapeutic activities of the therapeutic polypeptides.

In particular, the albumin fusion proteins which can be used according to the invention may include naturally occurring polymorphic variants of human albumin and fragments of human albumin. The albumin may be derived from any vertebrate, especially any mammal, for example human, monkey, cow, sheep, or pig. Non-mammalian albumins include, but are not limited to, such derived from hen and salmon. The albumin portion of the albumin-linked polypeptide may be from a different animal than the therapeutic polypeptide portion. The albumin portion of an albumin fusion protein which can be used according to the invention may comprise at least one subdomain or domain of HA or conservative modifications thereof.

Generally speaking, an albumin fragment or variant will be at least 20, preferably at least 40, most preferably more than 70 amino acids long. The albumin variant may preferentially consist of or alternatively comprise at least one whole domain of albumin or fragments of said domains, for example domains 1 (amino acids 1-194 of SEQ ID NO 34), 2 (amino acids 195-387 of SEQ ID NO 34), 3 (amino acids 388-585 of SEQ ID NO 34), 1+2 (1-387 of SEQ ID NO 34), 2+3 (195-585 of SEQ ID NO 34) or 1+3 (amino acids 1-194 of SEQ ID NO 34 +amino acids 388-585 of SEQ ID NO 34). Each domain is itself made up of two homologous subdomains namely 1-105, 120-194, 195-291, 316-387, 388-491 and 512-585, with flexible inter-subdomain linker regions comprising residues Lys106 to Glu119, Glu292 to Val315 and Glu492 to Ala511.

Besides albumin, alpha-fetoprotein, another member of the albumin family, has been claimed to extend the half-life of an attached therapeutic polypeptide in vivo (WO 2005/024044). The albumin family of proteins, evolutionarily related serum transport proteins, consists of albumin, alpha-fetoprotein (AFP; Beattie & Dugaiczyk 1982. Structure and evolution of human alpha-fetoprotein deduced from partial sequence of cloned cDNA. Gene 20:415-422), afamin (AFM; Lichenstein et al. 1994. Afamin is a new member of the albumin, alpha-fetoprotein, and vitamin D-binding protein gene family. J. Biol. Chem. 269:18149-18154) and vitamin D binding protein (DBP; Cooke & David 1985. Serum vitamin D-binding protein is a third member of the albumin and alpha fetoprotein gene family. J. Clin. Invest. 76:2420-2424). Their genes represent a multigene cluster with structural and functional similarities mapping to the same chromosomal region in humans, mice and rat. The structural similarity of the albumin family members suggests their usability as HLEPs. It is therefore another embodiment of the invention to use such albumin family members, fragments and variants thereof as HLEPs. The term "variants" includes insertions, deletions and substitutions, either conservative or non-conservative, where such changes do not substantially alter the active site, or active domain, which confers the therapeutic activities of the therapeutic polypeptides.

Albumin family members may comprise the full length of the respective protein AFP, AFM and DBP, or may include one or more fragments thereof that are capable of stabilizing or prolonging the therapeutic activity. Such fragments may be of 10 or more amino acids in length or may include about 15, 20, 25, 30, 50, or more contiguous amino acids of the respective protein sequence or may include part or all of specific domains of the respective protein.

Albumin family member fusion proteins of the invention may include naturally occurring polymorphic variants of AFP, AFM and DBP. The proteins may be derived from any vertebrate, especially any mammal, for example human, monkey, cow, sheep, or pig. Non-mammalian albumin family members include, but are not limited to, such derived from hen and salmon.

IgG and IgG-fragments without an antigen-binding domain may also be used as HLEPs. The therapeutic polypeptide portion is connected to the IgG or the IgG fragments preferably via the hinge region of the antibody or a peptidic linker, which may even be cleavable. Several patents and patent applications describe the fusion of therapeutic proteins to immunoglobulin constant regions to extend the therapeutic proteins' in vivo half-lives. US 2004/0087778 and WO 2005/001025 describe fusion proteins of Fc domains or at least portions of immunoglobulin constant regions with biologically active peptides that increase the half-life of the peptide, which otherwise would be quickly degraded in vivo. Fc-IFN-β fusion proteins were described that achieved enhanced biological activity, prolonged circulating half-life and greater solubility (WO 2006/000448). Fc-EPO proteins with a prolonged serum half-life and increased in vivo potency were disclosed (WO 2005/063808) as well as Fc fusions with G-CSF (WO 2003/076567), glucagon-like peptide-1 (WO 2005/000892), clotting factors (WO 2004/101740) and interleukin-10 (U.S. Pat. No. 6,403,077), all with half-life extending properties.

Therefore such immunoglobulin sequences, preferably Fc fragments and variants thereof can be used as HLEPs. Kazal-type serine protease inhibitors like Infestin-4 and modified Kazal-type serine protease inhibitors with enhanced inhibitory specificity for FXIIa like the SPINK-1 mutants may be fused to Fc domains or at least portions of immunoglobulin constant regions as HLEPs and expressed in *E. coli*, yeast, insect, plant or vertebrate cells or in transgenic animals. A SPINK-K2-Fc fusion protein is exemplarily shown in SEQ ID No 53.

According to the present invention preferred FXII inhibitors are fusion proteins, linking a Kazal-type serine protease inhibitor like Infestin-4 and modified Kazal-type serine protease inhibitors like the SPINK-1 mutants or fragment or variant thereof to the N- or C-terminus of a HLEP or fragment or variant thereof such that the fusion protein formed has an increased in vivo half-life compared to the corresponding Kazal-type serine protease inhibitor which has not been linked to a HLEP. An intervening peptidic linker may be introduced between the therapeutic polypeptide and the HLEP. Should the HLEP interfere with the therapeutic polypeptide's specific activity e.g. by steric hindrance, cleavable linkers may be introduced. Preferred enzymes for linker cleavage are the coagulation proteases of the intrinsic coagulation pathway, FXIIa, FXIa, FIXa, FVIIIa or FXa, wherein the most preferred cleaving enzyme is FXIIa.

The Kazal-type serine protease inhibitor family is one of the numerous families of serine protease inhibitors. Many proteins from different species have been described (Laskowski M and Kato I. 1980. Protein inhibitors of proteinases. Ann. Rev. Biochem. 49: 593-626).

"Infestin-4 and modified Kazal-type serine protease inhibitors" within the above definition include polypeptides that have the natural amino acid sequence or SEQ ID 30 to 33 or 49 to 52. However, such definition also includes polypeptides with a slightly modified amino acid sequence, for instance, a modified N-terminal or C-terminal end including terminal amino acid deletions or additions as long as those polypeptides substantially retain the activity of the respective Kazal-type serine protease inhibitors. "Kazal-type serine protease inhibitor" within the above definition also includes natural allelic variations that may exist and occur from one individual to another. "Kazal-type serine protease inhibitor" within the above definition further includes variants of Kazal-type serine protease inhibitors. Such variants differ in one or more amino acid residues from the wild type sequence. Examples of such differences may include truncation of the N- and/or C-terminus by one or more amino acid residues (e.g. 1 to 10 amino acid residues), or addition of one or more extra residues at the N- and/or C-terminus, as well as conservative amino acid substitutions, i.e. substitutions performed within groups of amino acids with similar characteristics, e.g. (1) small amino acids, (2) acidic amino acids, (3) polar amino acids, (4) basic amino acids, (5) hydrophobic amino acids, and (6) aromatic amino acids. Examples of such conservative substitutions are shown in Table 1.

TABLE 1

| (1)  | Alanine       | Glycine       |           |        |
|------|---------------|---------------|-----------|--------|
| (2)  | Aspartic acid | Glutamic acid |           |        |
| (3a) | Asparagine    | Glutamine     |           |        |
| (3b) | Serine        | Threonine     |           |        |
| (4)  | Arginine      | Histidine     | Lysine    |        |
| (5)  | Isoleucine    | Leucine       | Methionine| Valine |
| (6)  | Phenylalanine | Tyrosine      | Tryptophane|       |

The Kazal-type serine protease inhibitors and the modified Kazal-type serine protease inhibitors of the invention may be produced as recombinant molecules in prokaryotic or eukaryotic host cells, such as bacteria, yeast, plant, animal (including insect) or human cell lines or in transgenic animals according to WO 2008/098720. Optionally, the polypeptides are secreted from the host cells.

Dosages, Formulations, and Routes of Administration

It is preferred to purify the FXII inhibitor in particular the serine protease inhibitor of the present invention to greater than 80% purity, more preferably greater than 95% purity, and particularly preferred is a pharmaceutically pure state that is greater than 99.9% pure with respect to contaminating macromolecules, particularly other proteins and nucleic acids, and free of infectious and pyrogenic agents. Preferably, an isolated or purified serine protease inhibitor of the invention is substantially free of other polypeptides.

The therapeutic FXII inhibitors described in this invention can be formulated into pharmaceutical preparations for therapeutic use. The purified proteins or antibodies may be dissolved in conventional physiologically compatible aqueous buffer solutions to which there may be added, optionally, pharmaceutical excipients and carriers to provide pharmaceutical preparations.

A wide variety of pharmaceutically acceptable excipients and carriers are known in the art. Such pharmaceutical carriers and excipients as well as suitable pharmaceutical formulations have been amply described in a variety of publications (see for example "Pharmaceutical Formulation Development of Peptides and Proteins", Frokjaer et al., Taylor & Francis (2000) or "Handbook of Pharmaceutical Excipients", 3$^{rd}$ edition, Kibbe et al., Pharmaceutical Press (2000) A. Gennaro (2000) "Remington: The Science and Practice of Pharmacy", 20$^{th}$ edition, Lippincott, Williams, & Wilkins; Pharmaceutical Dosage Forms and Drug Delivery Systems (1999) H. C. Ansel et al., eds 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc). In particular, the pharmaceutical composition comprising the polypeptide of the invention may be formulated in lyophilized or stable soluble form. The polypeptide may be lyophilized by a variety of procedures known in the art. Lyophilized formulations are reconstituted prior to use by the addition of one or more pharmaceutically acceptable diluents such as sterile water for injection or sterile physiological saline solution.

In the subject methods, the inhibitor(s) may be administered to the individual using any convenient means capable of resulting in the desired therapeutic effect. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal, etc., administration i.e. formulations of the composition are delivered to the individual by any pharmaceutically suitable means of administration. Various delivery systems are known and can be used to administer the composition by any convenient route. Preferentially the compositions of the invention are administered systemically. For systemic use, the therapeutic proteins of the invention are formulated for parenteral (e.g. intravenous, subcutaneous, intramuscular, intraperitoneal, intracerebral, intrapulmonar, intranasal or transdermal) or enteral (e.g., oral, vaginal or rectal) delivery according to conventional methods. The most preferential route of administration is intravenous or intrapulmonary administration. The formulations can be administered continuously by infusion or by bolus injection. Some formulations encompass slow release systems.

Tablets and capsules for oral administration may contain conventional excipients such as binding agents, fillers, lubricants and wetting agents, etc. Oral liquid preparations may be in the form of aqueous or oily suspensions, solutions, emulsions, syrups, elixirs or the like, or may be presented as a dry product for reconstitution with water or other suitable vehicle for use. Such liquid preparations may contain conventional additives, such as suspending agents, emulsifying agents, non-aqueous vehicles and preservatives.

In general, for oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Formulations suitable for topical application may be in the form of aqueous or oily suspensions, solutions, emulsions, gels or, preferably, emulsion ointments. Formulations useful for spray application may be in the form of a sprayable liquid or a dry powder.

The agents can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

The FXII inhibitors of the present invention are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, and mode of administration and has to be determined in preclinical and clinical trials for each respective indication.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor (s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Those of skill will readily appreciate that dose levels can vary as a function of the specific compound, the severity of the symptoms and the susceptibility of the subject to side effects. Preferred dosages for a given compound are readily determinable by those of skill in the art by a variety of means. A preferred means is to measure the physiological potency of a given compound.

Depending on the mode of application, a considerable lower dose would be feasible for inhalation or spraying as compared to systemic administration by iv injection.

The pharmaceutical composition may be administered alone or in conjunction with other therapeutic agents. These agents may be incorporated as part of the same pharmaceutical.

The various products of the invention are useful as medicaments for the therapy of fibroproliferative interstitial lung disease. Accordingly, the invention relates to a pharmaceutical composition comprising a FXII inhibitor as describes herein in particular a Kazal-type serine protease inhibitor polypeptide as described herein, for the therapy cited above, notably pulmonary fibrosis, preferably idiopathic pulmonary fibrosis.

The modified DNAs of this invention may also be integrated into a transfer vector for use in the human gene therapy.

Specific siRNAs against FXII can be used for down-regulation or knock-down of FXII expression.

Any of the above-described embodiments is applicable to the inhibitor of the invention, to the methods of the invention, to the uses of the invention and to the kits of the invention, irrespective of whether they have been described only in combination with one of these categories.

EXAMPLES

Methods
Intratracheal Bleomycin Administration in Mice

Male mice weighing between 20-22 g were used in all experiments. Animals were kept according to NIH guidelines and experiments were undertaken with permission of local authorities. The animals were anesthetized by intraperitoneal injection of a mixture of ketamine hydrochloride and xylazine hydrochloride. Bleomycin in dosis 5U/kg body weight was given as aerosol. For bleomycin delivery, animals were orotracheally intubated and mechanically ventilated. A microsprayer (Penn-Century Inc, Philadelphia, Pa.) was filled with 100 µl of saline solution containing bleomycin, introduced into the tracheal cannula, positioned slightly above the carina and aerosol generation was achieved under end-expiratory breath arrest by rapidly emptying the syringe. Controls mice received vehicle only (0.9% saline). 5 mg/kg CTI and 8 mg/kg PCK, both diluted in 0.9% saline, were administrated intratracheally on day 9, 12, 15 and 18 in dosis or of mouse body weight, respectively. The mice were sacrificed after 21 days post application (if not indicated in the text) with a lethal dose of ketamine and xylazine.

Pulmonary Compliance Measurements

Mice were tracheotomised and ventilated in a volume driven mode at a positive end-expiratory pressure of 0 kPa. Respiration rate was set at 20 breaths·$min^{-1}$ and ventilation pressure was recorded while inflating the lung at a tidal volume of 200 µL.

Lung Preparation

After sacrifice of animals, the chest was opened and the lungs were flushed via a catheter that was placed into the pulmonary artery with PBS buffer. Once the effluent was clear of blood, lungs were removed and placed in paraformaldehyde or nitrogen for further examination. For cells isolation lungs were placed in PBS buffer.

Isolation of Murine and Human Lung Fibroblasts and Cell Culture

Human lung specimens of the pulmonary parenchyma and mouse lungs were chopped into <1 $mm^3$ pieces. The minced pieces were washed twice with PBS and then plated in 100-mm dishes (Greiner-bio-one, Frickenhausen, Germany). The specimens were cultured with Dulbecco's modified Eagle's medium (DMEM; Invitrogen, Karlsruhe, Germany) supplemented with 10% fetal calf serum (FCS; HyClone, South Logan, UT), and 1% penicillin/streptomycin (Invitrogen) in humidified atmosphere of 5% $CO_2$ at 37° C. Purity of isolated fibroblasts was verified by positive staining for vimentin, fibronectin and collagen IV. All experiments were carried out with lung fibroblasts from passages 3-4. The mouse NIH3T3 fibroblasts were cultured in DMEM supplemented with 10% FCS, and 1% penicillin/streptomycin in humidified atmosphere of 5% $CO_2$ at 37° C.

Microdessection of Lung Tissue and Alveolar Epithelial Type II Cells

Frozen speciments of lungs were sectioned at 10 µm in cryostat, mounted on noncoated, thin glass slides and stained with haemalaun (Roth) for 45 seconds. The sections were then immersed in 70% and 96% ethanol until use. Not more than 10 sections were prepared at once to restrict the storage time. Chosen areas of lung speciment were laser-microdessected under visual control (PALM, Bernried, Germany). Tissue was harvested by a syringe needle and transferred into a reaction tube containing 10 µl first strand buffer (52 mM Tris pH 8.3, 78 mM KCl, 3.1 mM MgCl$_2$,). Samples were frozen in liquid nitrogen and stored for further preparation. For alveolar type II cell microdessection, cryostat sections (10 μm thick) were mounted on poly-L-lysine (0.01%; Sigma, Deisenhofen, Germany)-covered slides and stored in acetone for 5 minutes. For proSP-C staining a polyclonal rabbit anti pro-SP-C antibody was applied (1:100 in PBS; Chemicon, Temecula, Calif.) followed by incubation with FITC-labeled goat anti-rabbit IgG (1:40 in PBS, Santa Cruz Biotechnology, CA). Not more then two sections were prepared at once to restrict the storage time. Alveolar type II cells were selected according to their staining pattern and lasser-microdessected under visual control. Samples with 50 cell profiles each were snap frozen in liquid nitrogen and stored for further preparation.

RNA Isolation and Reverse Transcriptase Reaction

Total RNA was extracted using a PeqGOLD Total RNA Kit (PeqLab, Erlangen, Germany) according to the manufacturer's instruction. One μg RNA each obtained from lung homogenate, microdessected lungs specimens, isolated fibroblasts or microdessected ATII cells was used in a reaction containing 4 μl 5× first strand buffer (FSB, 52 mM TRIS pH 8.3, 78 mM KCl, 3.1 mM MgCl2), 2 μl dNTP (10 mM each, Fermentas, St. Leon-Rot, Germany), 1 μl random hexamers (50 μM), 1 μl DDT (0.1 M), 1 μl Rnase inhibitor (40 U/μl) and 1 μl MuLV reverse transcriptase (200 U/μl, all from Applied Biosystems, Foster City, Calif.) in Rnase-free water (final volume 20 μl). The reaction was incubated at 43° C. for 1 hour and then at 94° C. for 2 minutes (TGradient Thermocycler, Biometra, Goettingen, Germany).

Real Time PCR

Real time PCR was performed by a Sequence Detection System 7700 (PE Applied

Biosystems, Foster City, Calif.). Reactions were set up with Platinum SYBR Green qPCR Super Mix-UDG (Invitrogen Karlsruhe, Germany) using 2 ml of cDNA. The β-actin gene was used as a reference gene. Cycling conditions were 95° C. for 6 min, followed by 45 cycles of 95° C. for 20 s, 55° C. for 30 s, and 73° C. for 30 s. Melting curve analysis and gel electrophoresis were performed to confirm the exclusive amplification of the expected PCR product. Gene expression was assessed using 2-$^{\Delta\Delta}$CT method as already described. The fold change in target gene relative to the endogenous control β-actin was determined by using equation fold change= 2-$^{\Delta\Delta}$CT, where -$^{\Delta\Delta}$CT=($C_{tTarget}$-$C_{tActin}$)treated-($C_{tTarget}$-$C_{tActin}$)control. Primers sequences are listed in Table 2.

TABLE 2

Primers sequence

| GENE | PRIMER SEQUENCE | SEQ ID NO: |
|---|---|---|
| human β-actin | F-5' ATT GCC GAC AGG ATG CAG GAA-3' | 1 |
| | R-5' GCT GAT CCA CAT CTG CTG GAA-3' | 2 |
| human FXII | F-5' ACG ACC TGG CTC TGT TGC-3' | 3 |
| | R-5'CTT GGC AGG CAC ACC GG-3' | 4 |
| human FXI | F-5' TCT GGC TTG TAT TAG GGA C-3' | 5 |
| | R-5' TCT TTG GGC CAT TCC TGG-3' | 6 |
| human HMWK | F-5' AAG AGT ACA GGT GGT CGC-3' | 7 |
| | R-5' CAA TCT AGG CTT TGG CCA AG3' | 8 |

TABLE 2-continued

Primers sequence

| GENE | PRIMER SEQUENCE | SEQ ID NO: |
|---|---|---|
| murine FXII | F-5' ACA GTG CTC TGC GAG GTG G-3' | 9 |
| | R-5' CGT TAG AGT TGG AGC AGC GAT-3' | 10 |
| murine FXI | F-5' TTA CAC AGA TTT TCA GCG GCC-3' | 11 |
| | R-5' TGT GTA CCC CCA TCC AGT CAC-3' | 12 |
| murine HMWK | F-5' GGA GAA CAA AGT CGT CCC GA-3' | 13 |
| | R-5' TGT GAC ACT CCG GAA AGG AGA-3' | 14 |
| murine β-actin | F-5' AGA GGG AAA TCG TGC GTG AC-3' | 15 |
| | R-5'CAA TAG TGA TGA CCT GGC CGT-3' | 16 |

Protein Isolation and Quantification

Harvested cells and frozen lungs specimens were lysed in RIPA buffer (50 mM TRIS-HCl pH 7.4, 150 mM NaCl, 1 mM EDTA, 1% Triton-X-100, 1% Sodium deoxycholate, 0.1% SDS) containing protease inhibitor cocktail (Roche, Mannheim, Germany). Lysates were incubated on ice for 30 min and then centrifugated (10000 rpm for 10 min at 4° C.). Supernatants were placed in new tubes and stored at −80° C. Protein quantification was performed using BCA™ Protein Assay Kit (Pierce, Rockford, Ill.) according to manufacturer's instructions. Different bovine serum albumin (BSA) concentrations were used as a standard.

SDS Polyacrylamide Gel Electrophoresis

Protein samples were mixed with 5×SDS-loading buffer (0.25 mol/l Tris-HCl pH 6.8, 10% (w/v) SDS, 50% Glycerol, 10% β-mercaptoethanol), boiled for 10 min, loaded into the SDS acrylamide gel (stacking gel: 4% acrylamide:bisacrylamide, 125 mM Tris-HCl pH 6.8, 0.1% (w/v) SDS, 0.1% (w/v) APS, 0.1% (v/v) TEMED; resolving gel (10%): 10% acrylamide:bisacrylamide, 375 mM Tris-HCl pH 8.8, 0.1% (w/v) SDS, 0.1% (w/v) APS, 0.1% (v/v) TEMED) and run in SDS-running buffer (25 mM Tris, 250 mM Glycine, 0.1% (w/v) SDS) at 100V.

Immunoblotting

Proteins separated on SDS polyacrylamide gel were transferred to a PVDF membrane (Amersham Biosciences, Freiburg, Germany) using wet transfer technique in transfer buffer (25 mM Tris, 192 mM Glycine, 20% (v/v) Methanol) for 1 h at 100V. After blocking with 5% non-fat dry milk in tris-buffered saline (TBS; 25 mM Tris-Cl, 150 mM NaCl, pH 7.5) containing 0.1% (v/v) Tween 20 (TBS-T), the membranes were incubated at 4° C. overnight with appropriate primary antibody diluted in 1% BSA in TBS-T. After 1 h incubation with peroxidase-labelled secondary antibody (all from Dako, Gostrup, Denmark) proteins were detected using ECL Plus Kit (Amersham Biosciences, Freiburg, Germany). To determine the amounts of protein loaded on the gel, blots were in 1 hour (stripping buffer: 100 mM Glycine, 1% HCl) and reprobed using an anti-β-actin or appropriate anti-pan antibody.

Immunocytochemistry

For immunocytochemical analysis, HLF were fixed with 4% paraformaldehyde for 10 min, permeabilized with 0.2% Triton X-100 in phosphate-buffered saline (PBS; 137 mM NaCl, 2.7 mM KCl, 10 mM Na$_2$HPO$_4$, 2 mM KH$_2$PO$_4$, pH 7.4) for 10 min, blocked with 3% BSA in PBS for 1 h at room temperature, and incubated overnight at 4° C. with one of the following antibodies: mouse anti-FXII, rabbit-anti-collagen IV, mouse anti-fibronectin (all from Abcam), goat anti-vimentin (Santa Cruz Biotechnology, Santa Cruz, Calif.), and rabbit anti-phospho-Smad 3 (Cell Signaling). Slides were incubated with rhodamine-conjugated secondary antibody (Dianova, Hamburg, Germany), and mounted with Vectashield mounting medium (Vector, Burlingame, Calif.). Nuclei were visualized by 4, 6-diamidino-2-phenylindole (DAPI; Sigma) staining. Controls were performed by substituting the primary antibody by a non-specific antibody. Images were captured by a Leica DMR microscope (Leica, Heidelberg, Germany) with 40'/1.25-0.75 oil-objective at room temperature and photographed using MetaMorph 7.0 (Molecular Devices, Downingtown, Pa.). All images illustrated are representative of at least four other areas per section, seen on at least three independent sections.

Immunohistochemistry

Paraffin-embedded, formalin-fixed lung tissue was sectioned at 5 microns and processed for immunohistochemical staining using appropriate primary antibody and ZytoChem Plus AP-Fast Red Kit according to the manufacturer's instructions (Zytomed Systems, Berlin, Germany). Negative controls were obtained in all cases by omitting the primary antibody.

Proliferation Assay

The primary murine lung fibroblasts were seeded in 48-well plates and starved in serum free DMEM (Dulbecco's Modified Eagle's Medium) for 24 hours prior to FXIIa (American Diagnostica, Stamford, Conn.) stimulation. In some experiments cells were preincubated with 5 µg/ml anti-uPAR (R&D Systems, Wiesbaden, Germany), anti-β1-integrin or anti-α5-integrin (both from Millipore, Billerica, Mass.) blocking antibodies 1-2 hours before exposure to FXIIa. In addition in some experiment 10.0 µM PD98059, 5 µM SP600125, 0.7 µM Wortmannin, 3 µM SB203580 (all from Calbiochem, Darmstadt, Germany) were added to the cell culture medium 1-2 hours prior to the addition of FXIIa. Cells were treated with 3-9 µg/ml FXIIa alone or in the presence of its specific inhibitors: Corn Trypsin Inhibitor (CTI, Calbiochem), H-D-Pro-Phe-Arg-chloromethylketone (PCK, Bachem, Weil am Rhein, Germany) or uPAR synthetic peptides. After 24-36 hours the cells were exposed to [3H] Thymidine (0.2 µCi per well) for 6-12 hours, rinsed three times with PBS and solubilized with 0.2 ml 0.5M sodium hydroxide. 0.1 ml of the solubilized material was quantified by liquid scintillation counting (TRI-CARB® 1500, A Canbera Company, Meriden, Conn.). [$^3$H]Thymidine incorporation was expressed as absolute radioactivity (counts per minute per well).

Immunoprecipitation

Primary murine fibroblasts were either unstimulated or stimulated with 6 µg/ml FXIIa for 30 minutes and lysed in buffer containing 20 mM HEPES pH=7.5, 10 mM EGTA, 40 mM β-glycerophosphate, 1% Triton X-100, 2.5 mM MgCl2, 1 mM DTT, 2 mM PMSF, 20 µg/ml aprotinin, 20 µg/ml leupeptin, 2 mM sodium vanadate. After 30 minute incubation at 37° C., insoluble material was pelleted by centrifugation at 10000 rpm for 10 minutes at 4° C. 100 µl of cell lysates were further incubated overnight at 4° C. with the 5 µg goat anti-uPAR antibody (Santa Cruz) or with goat IgG control antibody (R&D Systems). Next 100 µl of G-Sepharose (Amersham Biosciences) was added and immune complexes were allowed to bind for 1 hour at 4° C. Next, the beads were washed four times with lysis buffer, and adsorbed material was eluted in 2×SDS loading buffer. After boiling, the uPAR bound proteins were analyzed by Western blotting using mouse anti-FXII antibody (Abcam).

Generation FXII Promoter Constructs and Site-directed Mutagenesis

The human FXII promoter fragments were amplified by PCR from human lung DNA using Long PCR Enzyme Mix (Fermantas, St. Leon-Rot, Germany) according to the manufacturer's instruction. Cycling conditions were: 95° C. for 5 min, followed by 35 cycles at 95° C. for 30 s, 55° C. for 30 s, and 72° C. for 3 min. The following primers were used: human FXII-1630 forward 5'-CCGCTCGAGTGCTCTGT-GCTTAGTAACC-3' (SEQ ID NO:17); human FXII-907 forward 5'-CCGCTCGAGCAGCTACCCAGGAGGCT-3' (SEQ ID NO:18); human FXII-577 forward 5'-CCGCTC-GAGGCGTGGTGGTGGGCTCCT-3' (SEQ ID NO:19); human FXII-299 forward 5'-CCGCTC-GAGCTTAACCTCCTGATCTCC-3' (SEQ ID NO:20); human FXII-183DSBE-272 forward 5'-CCGCTC-GAGAAACTCCCAAACTTTCC-3' (SEQ ID NO:21); human FXII reverse 5'-CCCAAGCTTC-GTTGGTC-CAGCTGCCTATC-3 (SEQ ID NO:22)'. The PCR fragments were cloned into pGL3 Enhancer Vector (Promega, Mannheim, Germany) using XhoI and HindIII restriction sites (in bold). Point mutation was introduced into the CAGA box in pGL3-299 construct using the QuikChange Site-Directed Mutagenesis Kit (Stratagene, La Jolla, Calif.) according to the manufacturer's instructions. The following primers were used: human FXII-299C/T forward 5'-CCACAGGACCTA-GAGCATAAGAATG-3' (SEQ ID NO:23), human FXII-299C/T reverse: 5'-CATTCTTATGCTCTAGGTCCTGTGG-3' (SEQ ID NO:24). Successful cloning and insertion of the mutation into the CAGA box were confirmed by sequencing.

Transient Transfection and Luciferase Assay

NIH3T3 cells were transfected with indicated plasmids using FuGene6 (Roche, Mannheim, Germany) according to manufacturer's instruction. After 48 hours cells were either unstimulated or stimulated with 10 ng/ml TGF-β1 (R&D Systems) for further 24 hours. Subsequently, the cells were harvested and assayed for luciferase reporter activity using Promega Luciferase Assay Kit according to manufacturer's instruction. Cotransfection with pEGF-N1 (Clontech, Mountain View, Calif.) control vector was used to normalize for transfection efficiency.

Antisense Oligonucleotides

Pre-designed, commercially available siRNA sequences directed against human Smad 3 (Dharmacon, Chicago, Ill.), human JNK1 (Abnova, Heidelberg, Germany), and an universal negative-control siRNA (Ambion, Austin, Tex.) were employed. Cells were treated with siRNA (250 nM each) using the X-treme Gene siRNA Transfection Reagent (Roche). The siRNA-mediated downregulation of the target genes was assessed 72 h after transfection by Western blotting. At this time point cells were either unstimulated or stimulated with 10 ng/ml TGF-β1 for 24 hours and the Western blots for FXII were prepared as described above.

Chromatin Immunoprecipitation (ChIP)

ChIP was performed using Chromatin Immunoprecipitation Assay Kit from Millipore (Schwalbach, Germany) according to manufacturer's instruction. Briefly, NIH3T3 cells either unstimulated or stimulated with 10 ng/ml TGF-β1 (R&D Systems) were treated with 1% formaldehyde for 10 min. The cross-linked chromatin was then prepared and sonicated to an average size of 500-800 bp. The DNA fragments were immunoprecipitated with rabbit anti-Smad 3 antibody (Cell Signaling) or IgG isotype control overnight at 4° C. After reversal of cross-linking, the immunoprecipitated chromatin was amplified by PCR using following primers: human FXII-299 bp forward: 5'-CTTAACCTCCTGATCTCC-3' (SEQ ID NO:25); human FXII-299 bp reverse: 5'-CGTTGGTCCAGCTGCCTATC-3' (SEQ ID NO:26). PCR products were separated on the 2% agarose gel and visualized by ethidium bromide staining.

Streptavidin Pull-down Assay

The double-stranded biotynylated DNA fragment (SBE-283/-258: 5'-biotin-CTTAACCTCCTGATCTCCACAGGACCCAGAGCATAAGAATGTCCC-3' (SEQ ID NO:27) or SBE-283/-258 C/T: 5'-biotin-CTTAACCTCCTGATCTCCACAGGACCTAGAGCATAAGAATGTCCC-3') (SEQ ID NO:28) spanning SBE was assayed for protein interaction in 100 ml binding reaction containing 20 µg of nuclear extract, 20 pmol/µl of biotinylated template, and 1 µg of poly(dI-dC). After incubation for 1 h at 30° C., streptavidin MagneSphere paramagnetic particles (Promega) pre-equilibrated in binding buffer (20 mM Hepes (pH 7.9), 80 mM KCl, 10 mM MgCl2, 10% (v/v) glycerol, 2 mM DTT, 500 µg/ml of BSA and 0.05% (v/v) Nonidet P-40) were added to the reaction, and incubated for another 1 h at 30° C. The DNA-protein complexes were washed three times with wash buffer (20 mM HEPES (pH 7.9), 50 mM KCl, 6.25 mM MgCl2, 0.5 mM EDTA, 2 mM DTT, and 8.5% (v/v) glycerol) using a magnetic device (Dynal MPC®-E, Magnetic Particle Concentrator). After boiling, the DNA-bound proteins were analyzed by Western blot using rabbit anti-phospho Smad 3 antibody (Cell Signaling). Nuclear extracts were prepared using NE-PER™ Nuclear and Cytoplasmic Extraction Reagent (Pierce, Rockford, Ill.) according to manufacturer's instruction.

Statistics

Data are presented as mean±SD unless otherwise stated. Normal distribution was analysed by Shapiro-Wilk test. Statistical comparisons between two populations were performed using unpaired Student t-tests. Differences between multiple groups were compared by One-way ANOVA followed by Tukey post test or Kruskal-Wallis followed by Dunn's post test. A level of $p<0.05$ was considered statistically significant. The statistical significance between survival curves was assessed by log-rank test.

Results

Expression of FXII, FXI and HMWK is altered in idiopathic pulmonary fibrosis lungs.

To reveal potential role of intrinsic coagulation pathway components in the pathogenesis of Idiopathic Pulmonary Fibrosis (IPF), expression of FXII, FXII and HMWK in lung tissue from IPF patients and donors was analyzed using quantitative real-time (q)RT-PCR. As shown in FIG. 1A, FXII and HMWK mRNA level was markedly upregulated in IPF lung specimens. The cell-specific expression of intrinsic coagulation pathway components was quantified in primary human alveolar epithelial cells type II (ATII) and fibroblasts derived from lungs of IPF patients and donors. Lung fibroblasts isolated from IPF lung tissue expressed FXII mRNA at higher levels then cells from donor lungs. FXII mRNA was not detected in ATII cells. FXI and HMWK expression in ATII cells and lung fibroblasts derived from lungs of IPF patients was not changed comparing to donor samples. Furthermore, expression of FXII, FXI and HMWK in alveolar septae microdesected from fibrotic (FIG. 1F) and healthy (FIG. 1H) regions of IPF tissue was analyzed (FIG. 1B). mRNA level of FXII, FXI and HMWK in healthy regions from IPF lungs was not changed in comparison to donor tissue (FIG. 1C). In contrast, there was significant upregulation of FXII, FXI and HMWK genes in fibrotic areas of IPF lungs.

Figure 2:
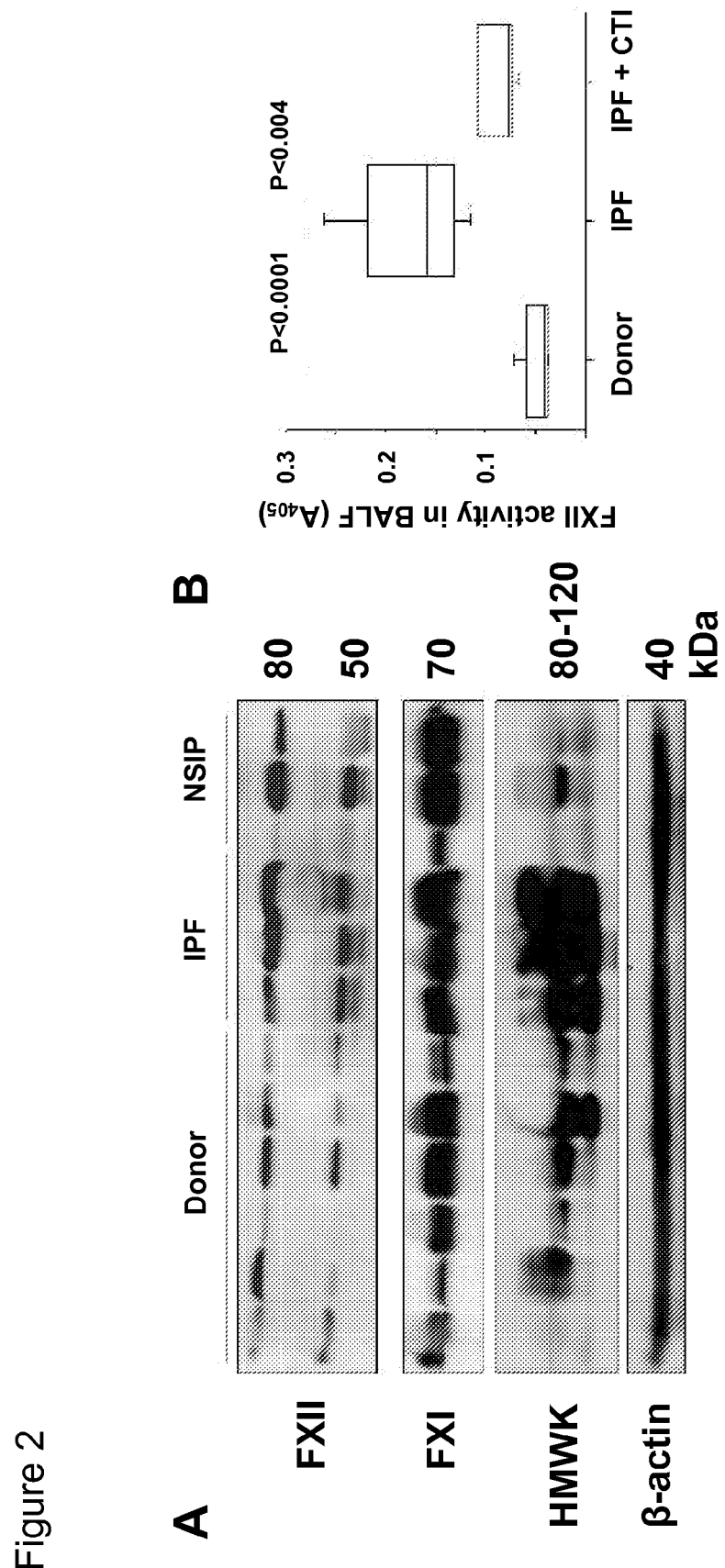
FIG. 2: Protein level of FXII, FXI and HMWK is increased in lung homogenates of IPF patients. (A) Representative immunoblot showing the expression of FXII, FXI and HMWK in lung homogenates of donor and IPF patients. β-actin served as a loading control. (B) FXII activity assay using chromogenic substrate (B). Corn Trypsin Inhibitor was used to specifically block FXII activity. Results are derived from 10 donors and 10 IPF patients. Data are presented as box and whisker plots, in which the horizontal line within each box represents the median, the limits of each box represent the interquartile range and the whiskers represent the maximum and minimum values. Tested for statistical significance by Mann-Whitney test. Significance levels are indicated.

In line with the mRNA expression, protein levels of FXII and HMWK were upregulated in IPF lungs. The expression of FXI protein in IPF lungs was not changed (FIG. 2A). Activity assay using FXII chromogenic substrate demonstrated increased enzymatic activity FXII in broncholaveolar lavage fluid (BALF) from IPF patients (FIG. 2B). The specificity of performed assay was proved by blockade of FXII activity by its inhibitor, Corn Trypsin Inhibitor (CTI).

Figure 3:
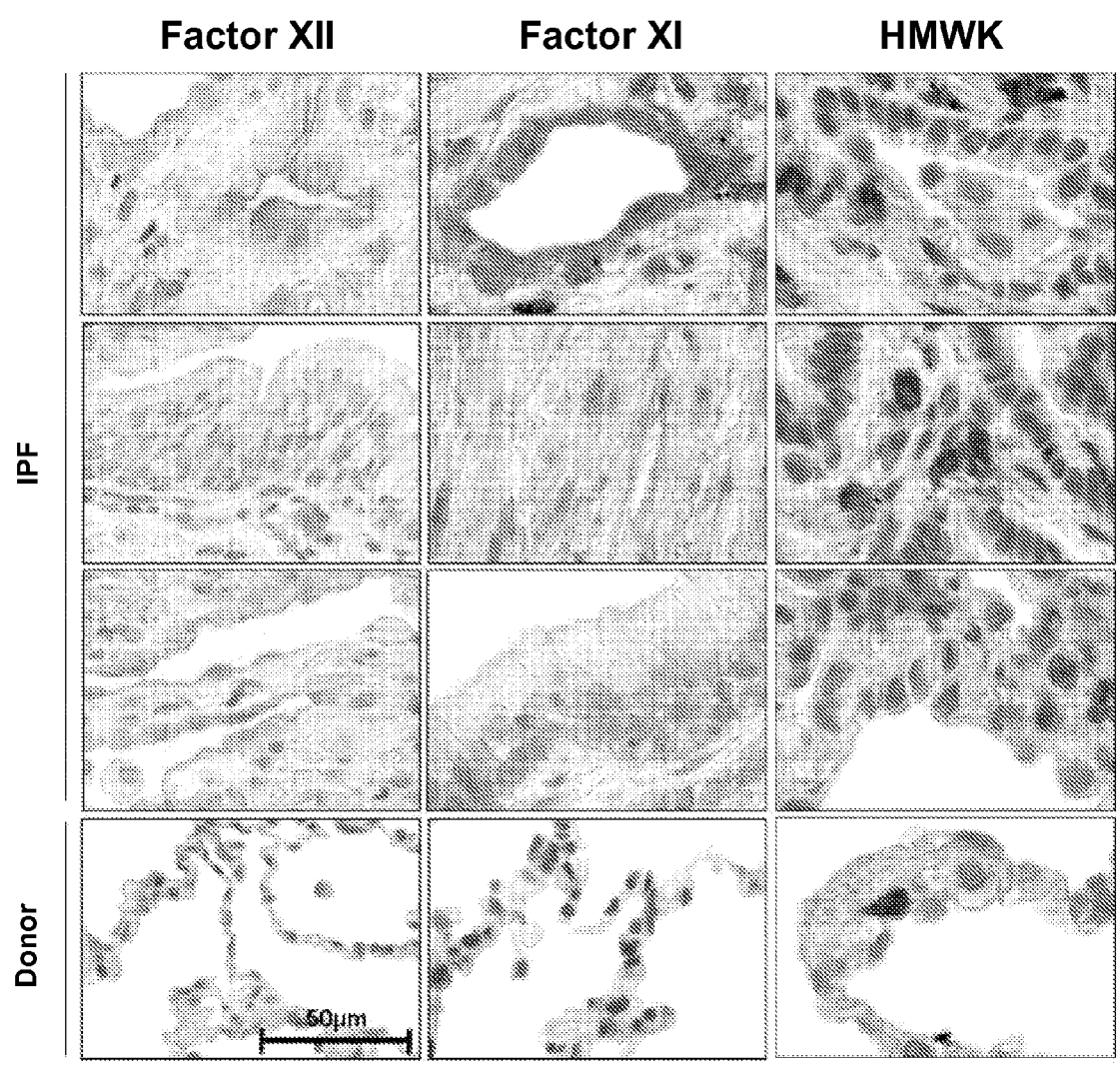
FIG. 3: Expression and localization of FXII, FXI and HMWK in lung tissues of donor and IPF patients. Immunohistochemical staining was performed on parafine lung tissue sections obtained from donors and IPF patients. One representative IPF patient and one control out of five per group are shown. Bar size is indicated.

Immunohistochemistry staining of FXII, FXI and HMWK was performed to characterize localization of these factors in donor and IPF lungs. As shown in FIG. 3 the expression of all intrinsic coagulation factors was markedly increased in IPF sections compared to donor tissue. The strongest immunoreactivity of FXII was observed in fibroblasts and on the surface of ATII cells. FXI was mainly expressed in ATII cells and in fibroblasts, whereas HMWK was mostly present in monocytes.

Expression of FXII, FXI and HMWK is Elevated in Bleomycin Lungs.

Figure 4:
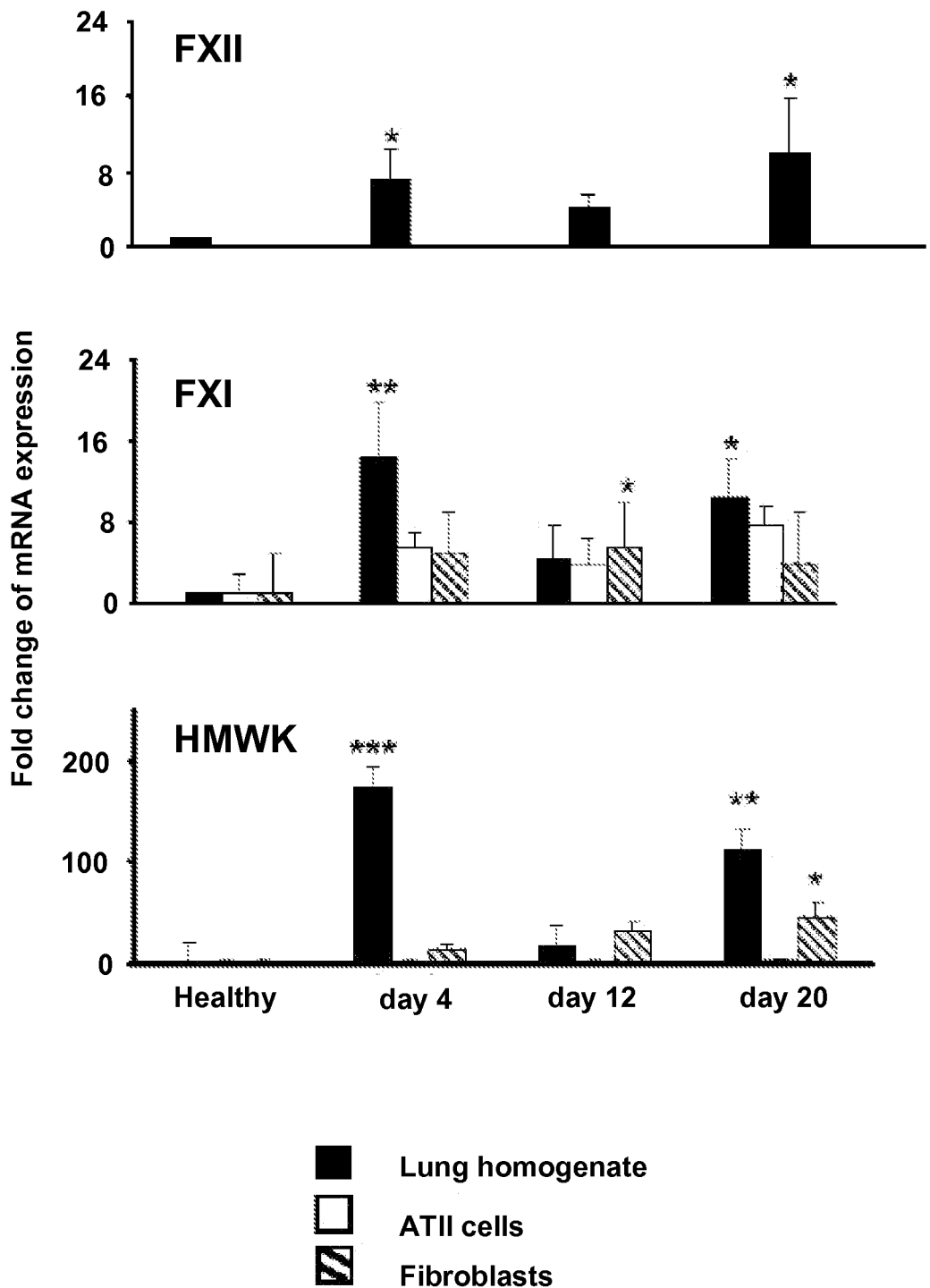
FIG. 4: mRNA level of FXII, FXI and HMWK is elevated in the lungs of bleomycin treated mice. The quantative RT-PCR analyse of FXII, FXI and HMWK expression in control and bleomycin lung homogenates as well as in lung fibroblasts and alveolar epithelial type II cells (AT II) isolated from lungs of control (n=10) and bleomycin challenged (n=10) mice. Given is the fold-increase in mRNA expression in bleomycin lungs (normalized for β-actin expression) versus values obtained for control lungs. Results are presented as mean±s.e.m., *p<0.0005, p<0.005, *p<0.05; Student's t-test.

To determine whether the findings in the IPF lungs translate to animal model of lung fibrosis, the expression of FXII, FXI and HMWK was quantified in lungs of bleomycin challenged mice. The RT-PCR revealed upregulation of FXII, FXI and HMWK in lung homogenate from bleomycin treated mice at day 4 and day 20 post bleomycin instillation (FIG. 4). Interestingly, FXII mRNA was not detected in primary murine lung fibroblasts and ATII cells. FXI expression in ATII cells derived from bleomycin lungs was not changed, while its expression in lung fibroblasts was upregulated at day 12 post bleomycin administration. There was significant upregulation of HMWK mRNA in lung fibroblasts at day 20 post bleomycin application, while no change in HMWK expression was observed in ATII cells.

Figure 5:
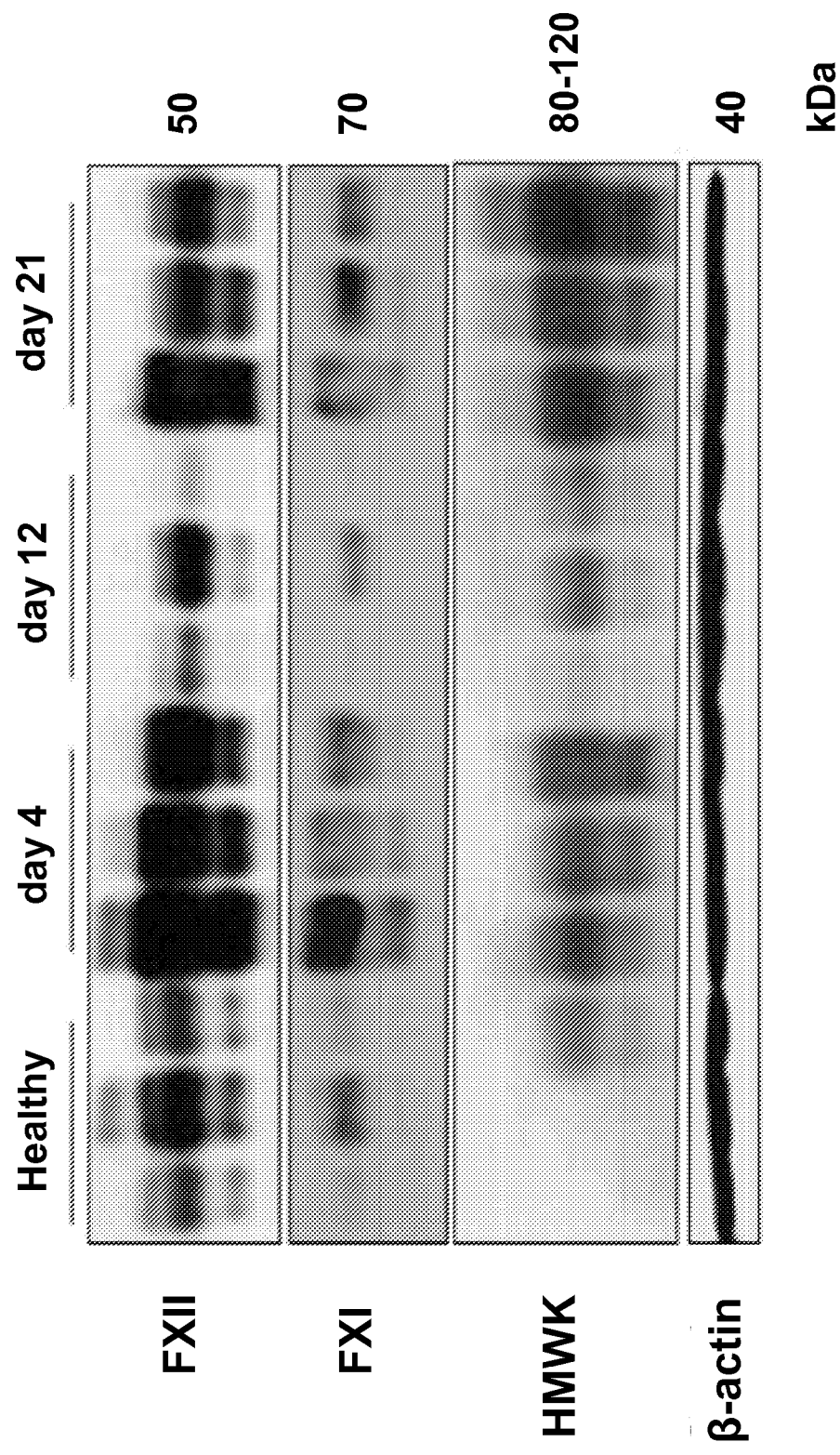
FIG. 5: Increased protein level of FXII, FXI and HMWK in lung homogenates of control and bleomycin challenged mice. Representative immunoblot showing the expression of FXII, FXI and HMWK in lung homogenate of saline control and bleomycin lungs. β-actin served as a loading control.

As compared to findings from IPF tissue speciments, immunoblotting showed a similar upregulation of FXII, FXI and HMWK protein level in lung homogenate at day 4 and 20 post bleomycin application (FIG. 5.).

Figure 6:
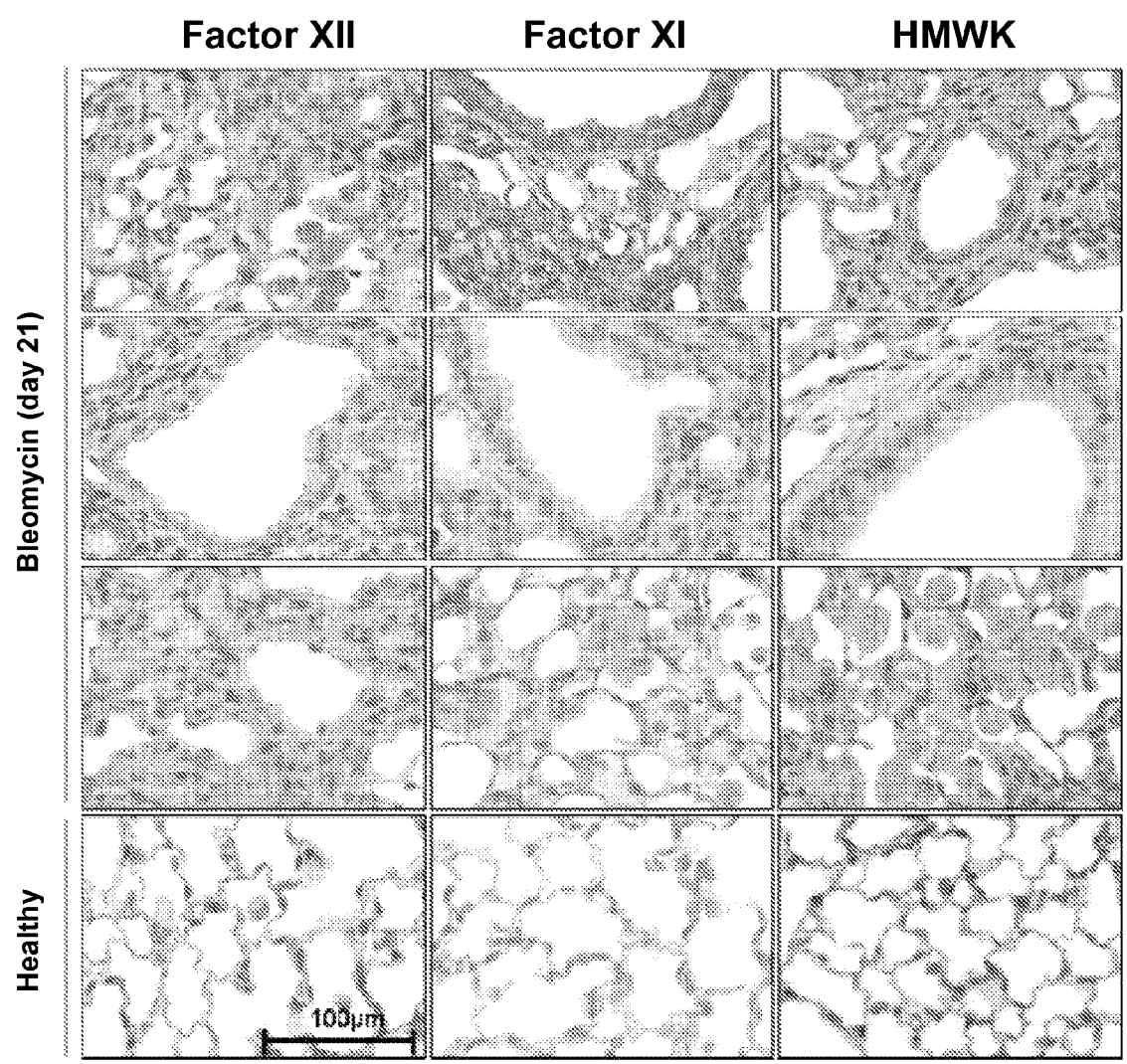
FIG. 6: Expression and localization of FXII, FXI and HMWK in the lungs of control and bleomycin treated mice. Representative histological section showing FXII, FXI and HMWK immunolocalization in the lungs from saline or bleomycin treated mice. One representative bleomycin mouse and one control out of ten per group are shown. Bar size is indicated.

Immunolocalization studies confirmed strong expression of FXII, FXI and HMWK in bleomycin-injured lungs (day 20 post application) compared to the weak signal observed in the lungs of saline treated mice (FIG. 6). Weak FXII, FXI and HMWK staining in normal control lungs was mainly observed in alveolar macrophages. After bleomycin application strong FXII, FXI and HMWK immunoreactivity was visible in fibrotic regions and alveolar macrophages.

FXII Knockout or Inhibition Protects Against Bleomycin Induced Lung Fibrosis.

Figure 7:
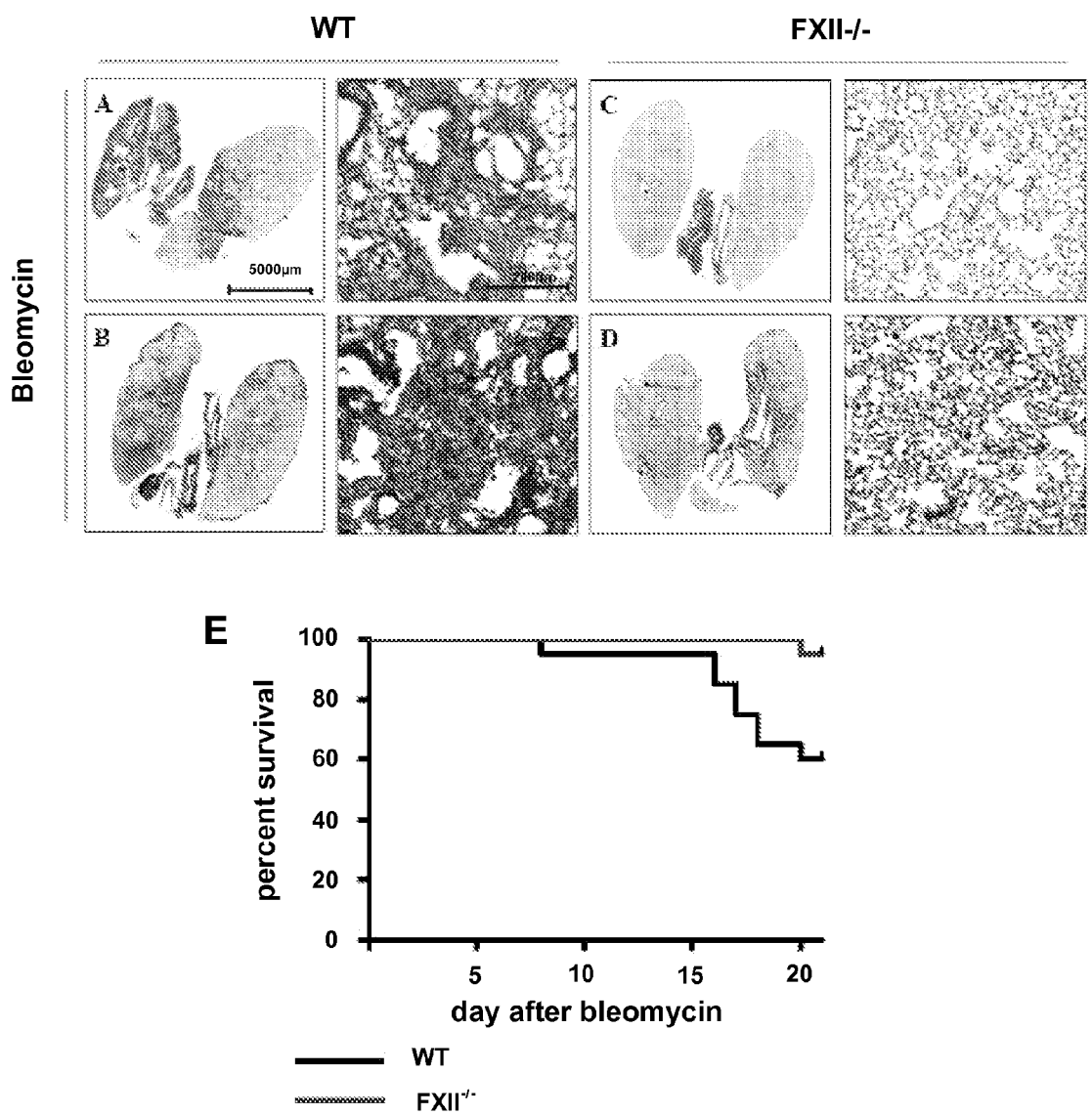
FIG. 7: FXII-/- mice are protected against bleomycin-induced lung fibrosis. Hematoxylin and eosin staining of lungs of (A) wild type and (C) FXII-/- mice 21 days after bleomycin challenge. Trichrom staining of (B) wild type and (D) FXII-/- mice 21 days after bleomycin challenge. Green colour indicates collagen staining. Bar size is indicated. (E) Survival curve demonstrating mortality rate of WT and FXII-/- mice after bleomycin challenge, n=20 mice/group. Significant difference by log-rank test, P=0.007 FXII-/- versus WT survival.

To determine the role of FXII in lung fibrosis, mice deficient in FXII were challenged with bleomycin. As revealed by hematoxylin and eosin staining, at day 21, wild type (WT) animals treated with bleomycin showed remarkable lung fibrosis characterized by distortion of the normal lung architecture, increased interstitial wall thickness and increased number of fibroblasts (FIG. 7A). In contrast FXII-deficient (FXII-/-) mice had markably decreased fibrotic changes in the lungs (FIG. 7C).

Figure 8:
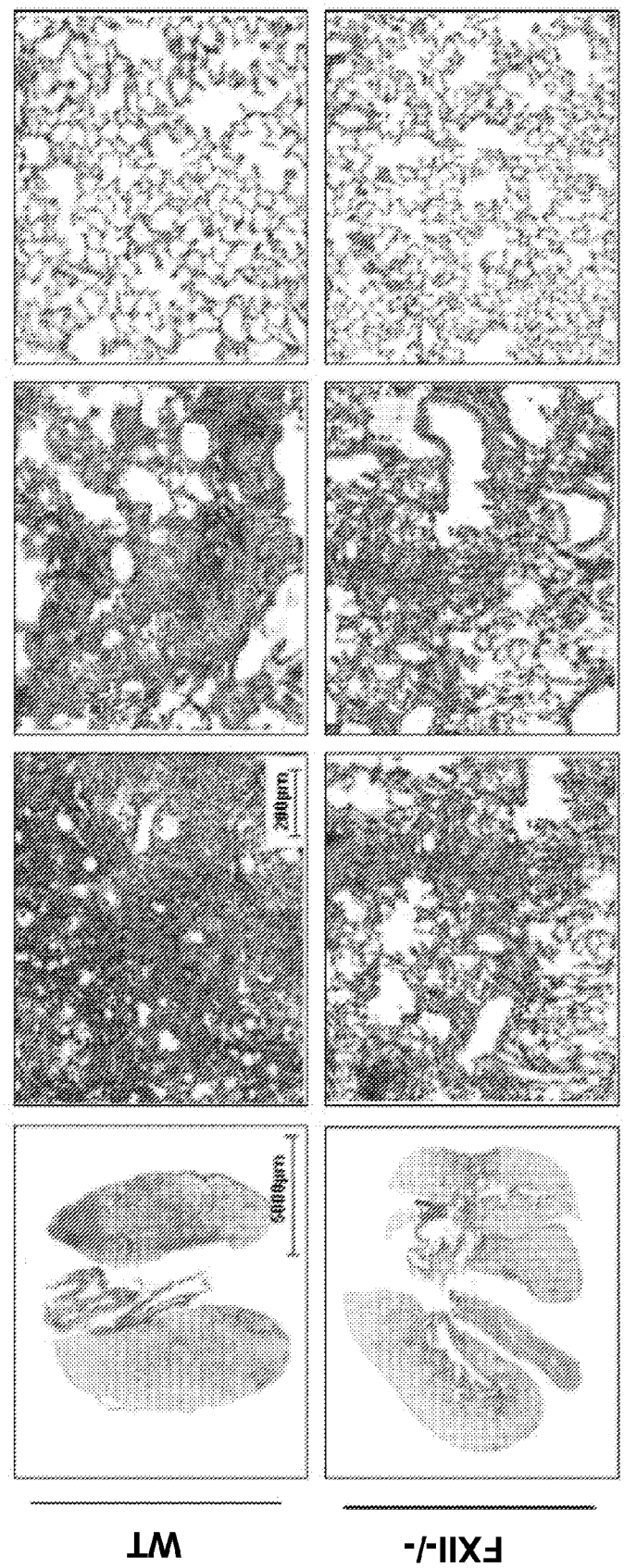
FIG. 8: Fibrin deposition in the lungs of FXII-/- mice is not impaired after bleomycin application. Fibrin immunostaining in lung tissue from bleomycin treated WT and FXII-/-mice 3 weeks after bleomycin instillation. Red colour indicates fibrin. The photomicrographs were selected to illustrate the pattern and extent of fibrin deposition in the abnormal and normal regions of lung for each experimental group. Bar size is indicated.

Masson trichrome staining was performed to assess abnormalities in lung collagen deposition after bleomycin challenge. Accumulation of collagen was more remarkable in WT animals (FIG. 7B) as compared to FXII-/- mice (FIG. 7D). Finally, mortality of FXII-/- mice was significantly lower in comparison to WT mice (FIG. 7E). At day 21 day post bleomycin challenge, the mortality of WT mice was 40%, whereas the mortality of FXII-/- was 5%. To determine whether any changes in fibrin deposition occur in WT and FXII-/- mice after bleomycin application, lung section were stained with anti-fibrin antibody (FIG. 8). WT animals receiving bleomycin showed extensive fibrin deposition in fibrotic areas. Fibrin staining was observed in alveolar space in close proximity and in areas of fibrosis. Similar pattern was visible in the lungs of FXII-/- mice challenged with bleomycin.

Figure 9:
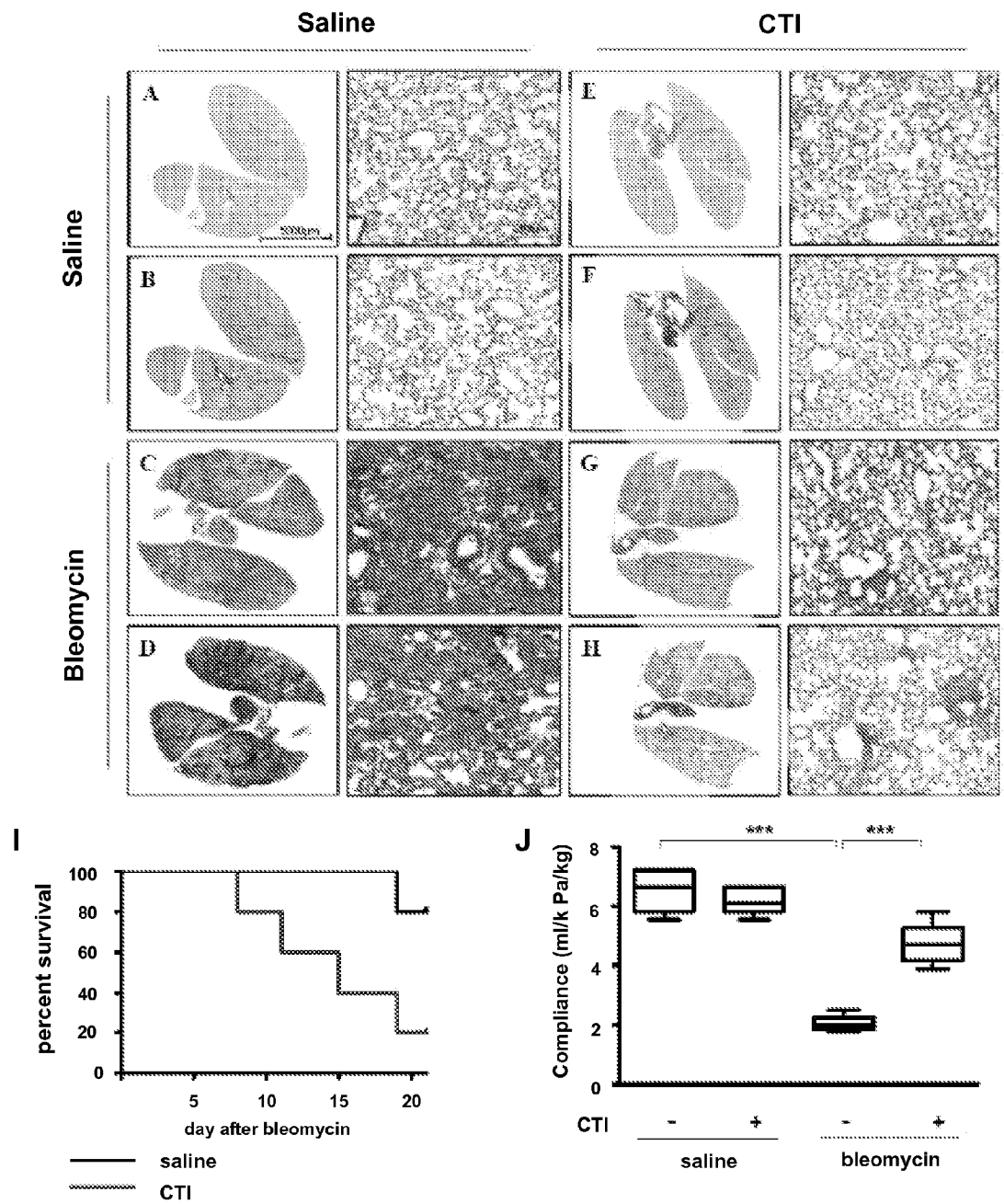
FIG. 9: FXIIa inhibitor attenuates bleomycin induced lung fibrosis. Hematoxylin and eosin staining of lungs at day 21 days post (C,G) bleomycin or (A,E) saline application. Trichrom staining of lungs at day 21 post bleomycin (D,H) or saline (B,F) instillation. Green colour indicates collagen staining. Bar size is indicated. (I) Survival curve demonstrating mortality rate of WT and FXII-/- mice after bleomycin challenge, n=20 mice/group. Significant difference by log-rank test, P=0.007. (J) Compliance measurement 21 days after bleomycin or saline administration. Data are presented as box and whisker plots, in which the horizontal line within each box represents the median, the limits of each box represent the interquartile range and the whiskers represent the maximum and minimum values. n=5 mice/group; ***P<0.05; ANOVA, Tukey's post test.

To evaluate the possible therapeutical effects of FXII inhibition on bleomycin induced lung injury, the saline control mice and bleomycin challenged mice received Corn Trypsin Inhibitor, a specific FXII activity inhibitor. Saline or CTI were administered intratracheally at a dose 5 mg/kg body weight at day 9, 12, 15 and 18. At day 21 the mice were sacrified, the lung compliance was measured and lung tissue specimens were collected. Bleomycin-treated mice which received saline showed severe fibrotic changes with loss of normal architecture and extensive collagen deposition (FIG. 9C, D). Extensive fibrosis development was reflected by strong decrease in compliance (FIG. 9J). In contrast histologic findings in the lungs of bleomycin treated mice that obtained CTI demonstrated less fibrotic lesions (FIG. 9G). Collagen accumulation as assessed by Masson-Trichrom staining was markedly reduced in FXII inhibitor treated animals (FIG. 9H). Moreover, the compliance of CTI treated animals was significantly improved (FIG. 9J). At day 21 post bleomycin challenge, the mortality of saline treated mice was 80%, whereas the mortality of animals, which received CTI was 20% (FIG. 9I). The control animals, which received CTI, had no histological changes in the lung but they showed a mild degree of inflammatory cells infiltration into airspaces (FIG. 9E). This side effect of CTI may limit its therapeutical application.

Bradykinin Receptor 1/2 Knockout Mice are not Protected Against Bleomycin Induced Lung Fibrosis.

Figure 10:
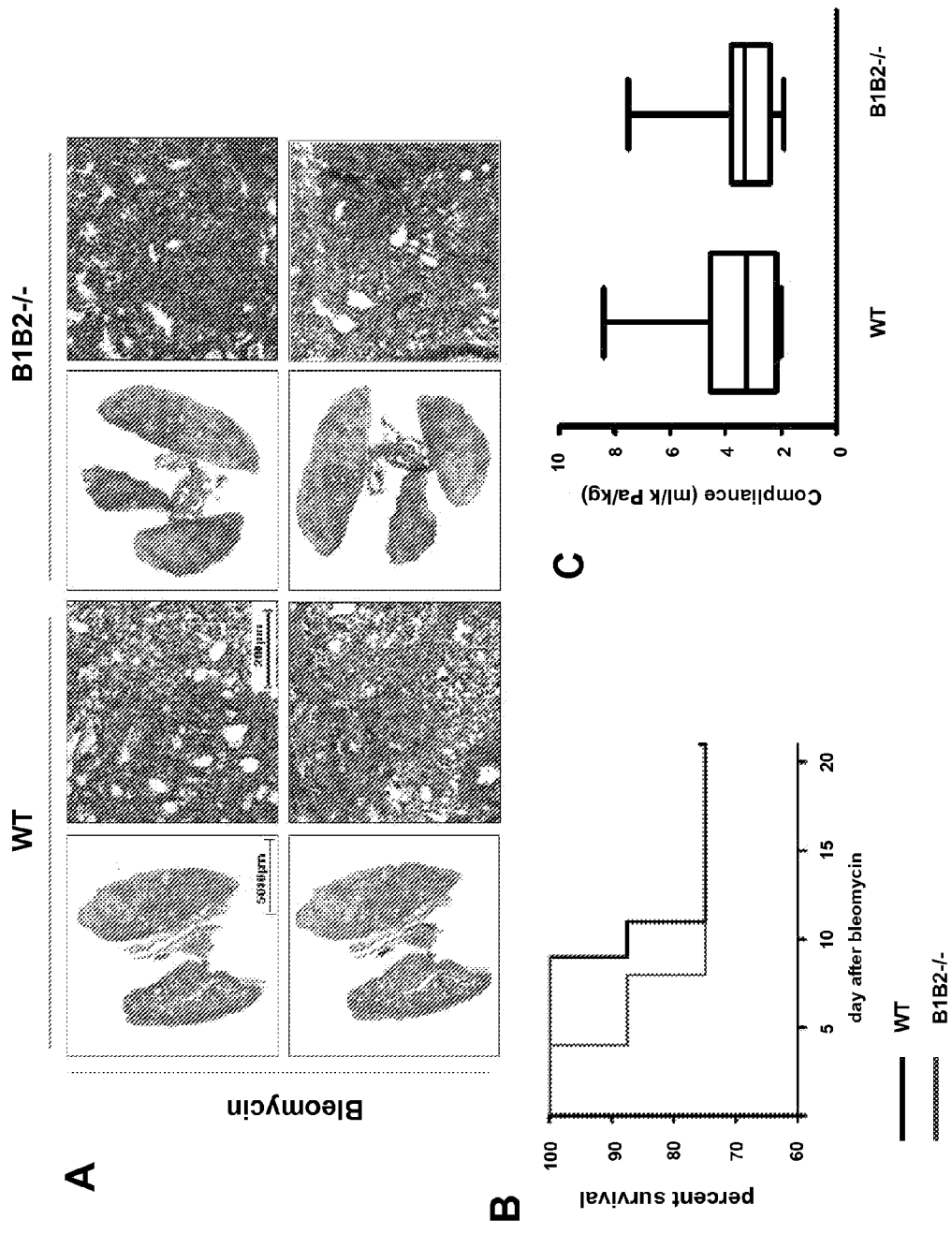
FIG. 10: B1B2-/- mice are not protected against bleomycin induced lung fibrosis. (A) H&E and Masson-Trichrom stainings of lungs of WT and B1B2-/- treated mice 21 days after bleomycin instillation. Green colour indicates collagen staining. Bar size is indicated. (B) Survival curve demonstrating mortality rate of WT and B1B2-/- mice after bleomycin challenge, n=20 mice/group. Significant difference by log-rank test, p=0.86. (C) Compliance measurement 21 after days after bleomycin administration. Data are presented as box and whisker plots, in which the horizontal line within each box represents the median, the limits of each box represent the interquartile range and the whiskers represent the maximum and minimum values. n=20 mice/group; difference not significant; Mann-Whitney test.

FXIIa is a potent activator of plasma prekallikrein. Activated kallikrein cleaves further HMWK to HKa and Bradykinin (BK), which acts as a vasodilator and proinflamatory peptide through two G-protein-coupled receptors: B1 and B2. To determined if FXII induced bradykinin delivery contributes to development of lung fibrosis, bradykinin 1 and 2 receptors deficient mice (B1B2-/-) were challenged with bleomycin. After 21 days of bleomycin application, both WT and B1 B2-/- animals developed strong fibrotic changes and collagen accumulation in the lung as evidenced by H&E staining and Masson-Trichrom staining respectively (FIG. 10A). No improvement in lung compliance (FIG. 10C) and survival (FIG. 10B) was observed in B1B2-/- in comparison to WT mice after bleomycin administration.

FXII Stimulates Proliferation of Lung Fibroblasts.

Figure 11:
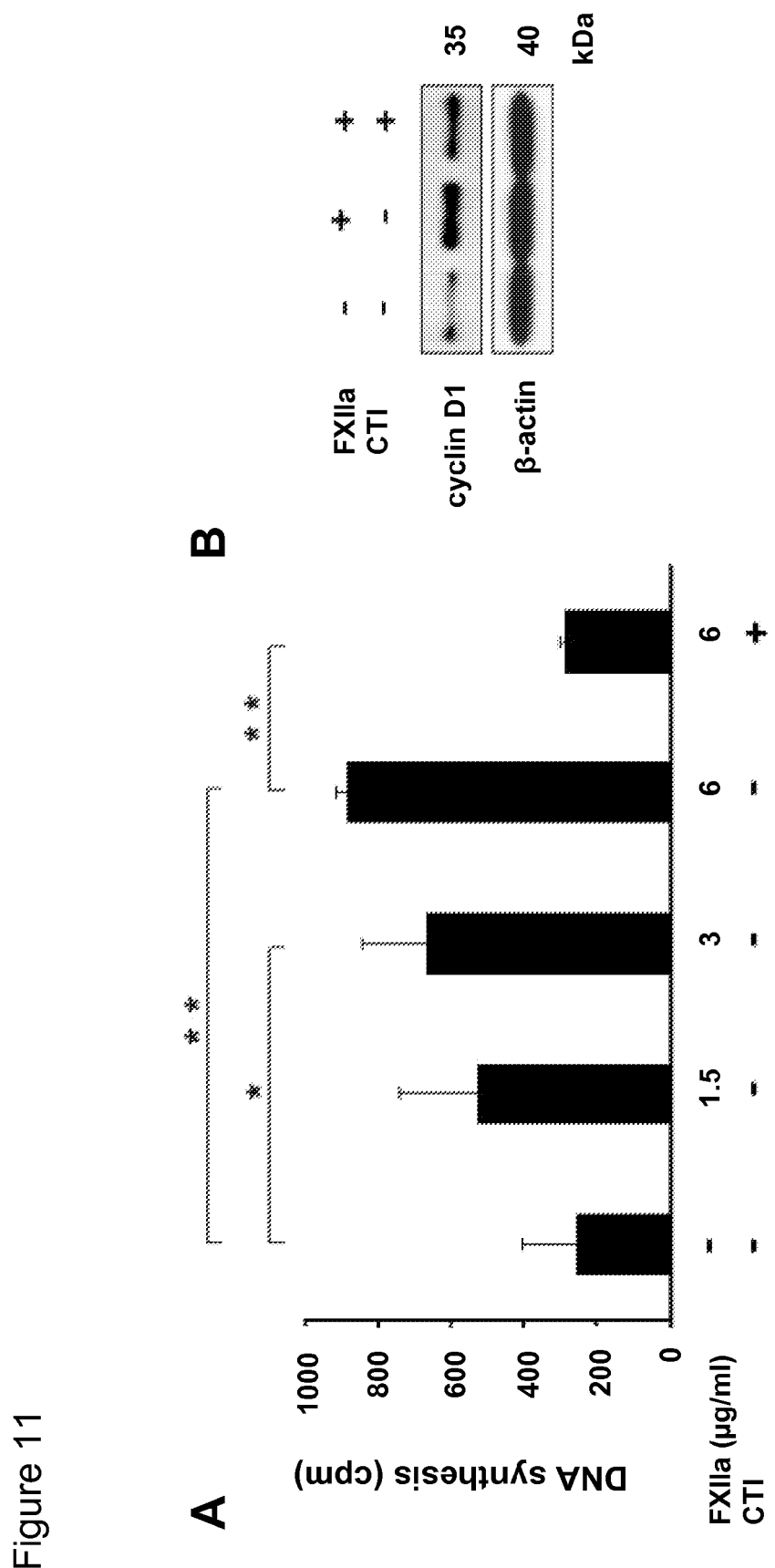
FIG. 11: FXIIa stimulates proliferation of murine lung fibroblasts. (A) [$^3$H]-Thymidine incorporation in murine lung fibroblasts exposed to FXIIa. The values are presented as the mean±SEM of four determinations performed within one experiment of at least 3. **P<0.0005; *P<0.05; ANOVA, Tukey's post test (B) Representative immunoblot showing cyclin D1 expression in murine lung fibroblasts 6 hours after 6 µg/ml FXIIa stimulation. β-actin served as a loading control.

FXII has been reported to act as mitogen for human hepatoma (Hep2) cells, smooth muscle cells, alveolar type II cells and endothelial cells. Taking into consideration that intensive fibroblasts proliferation is a hallmark of lung fibrosis, it was of interest to check if FXII may control lung fibroblasts proliferation as well. To answer this question murine lung fibroblasts were stimulated with increasing concentration of FXIIa and [3H]-thymidine incorporation was measured. The dose-dependent increase in DNA synthesis was observed after FXIIa treatment (FIG. 11A). FXII-induced proliferation was blocked by FXIIa specific inhibitor, CTI. Additionally, increased cyclin D expression after exposure to FXIIa confirmed FXIIa mitogenic activities toward murine lung fibroblasts (FIG. 11B).

In order to investigate the contribution of different signal transduction pathways to FXIIa-induced proliferation of murine lung fibroblasts, MAPKs and Akt phosphorylation kinetics in response to FXIIa stimulation were analyzed. A marked increase in p38, p44/42 and Akt activity was visible after 15 min, whereas no phosphorylation of JNK and c-jun was observed. CTI attenuated p44/42 and Akt phosphorylation after 30 min of FXIIa exposure. After determination of the phosphorylation kinetics, it was next analysed whether interference with these pathways would affect FXIIa-induced proliferation of murine lung fibroblasts. To assess this question, specific inhibitors of JNK, P13K, MEK and p38 kinases (SP600125, Wortmannin, PD98059, and SB203580, respectively) were used and their effect on FXIIa mitogenic activities was evaluated. As shown in FIG. 12A, B inhibition of MEK activity by PD98059 led to reduction of murine lung fibroblasts proliferation in response to FXIIa. No change in DNA sythesis was visible when cells were pretreated with inhibitors of P13K, JNK, and p38 kinases.

Figure 13:
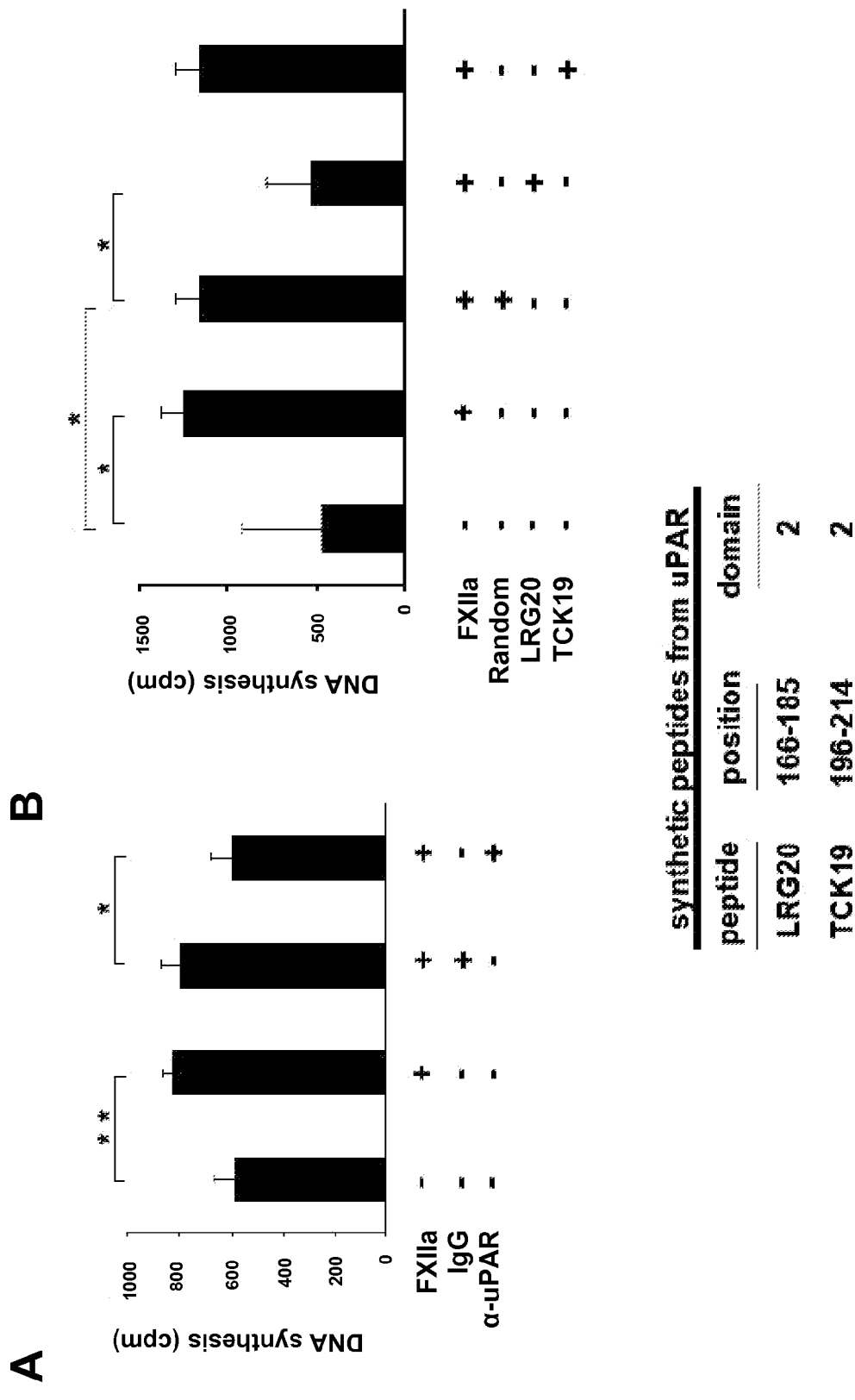
FIG. 13: uPAR mediates FXIIa induced murine lung fibroblasts proliferation. (A) [$^3$H]-thymidine incorporation in murine lung fibroblasts preatreated with uPAR blocking antibody or IgG isotype control antibody prior to FXIIa stimulation. (B) [$^3$H]-thymidine incorporation in murine lung fibroblasts after exposure to FXIIa in the presence of peptides from uPAR's domain 2 (LRG or TCK) or random peptide. The values are presented as the mean±SEM of four determinations performed within one experiment of at least three. **P<0.0005; *P<0.05; ANOVA, Tukey's post test.

FXII has been reported to bind to endothelial cell surface in complex with gC1qR, urokinase plasminogen activator receptor (uPAR) and cytokeratin 1 (CK1). Furthermore, there are studies indicating that uPAR is involved in FXII-induced endothelial cells proliferation. To investigate whether uPAR mediates FXIIa mitogenic activities towards murine lung fibroblasts, cells were treated with anti-u PAR blocking antibody prior to FXIIa stimulation. Cell proliferation, as measured by [$^3$H]-thymidine incorporation was blocked by anti-uPAR antibody (FIG. 13A). Moreover, experiments using peptides corresponding to uPAR's domain 2 confirmed importance of this receptor for FXIIa mitogenic activities and revealed the potential FXII binding site on uPAR. Peptide LRG20 (position 166-185) from uPAR's domain 2 blocked increase in DNA synthesis after FXIIa stimulation (FIG. 13B). In comparison, peptide TCK from domain 2 (position 196-214) and random peptide had no effect on FXIIa induced proliferation.

Figure 14:
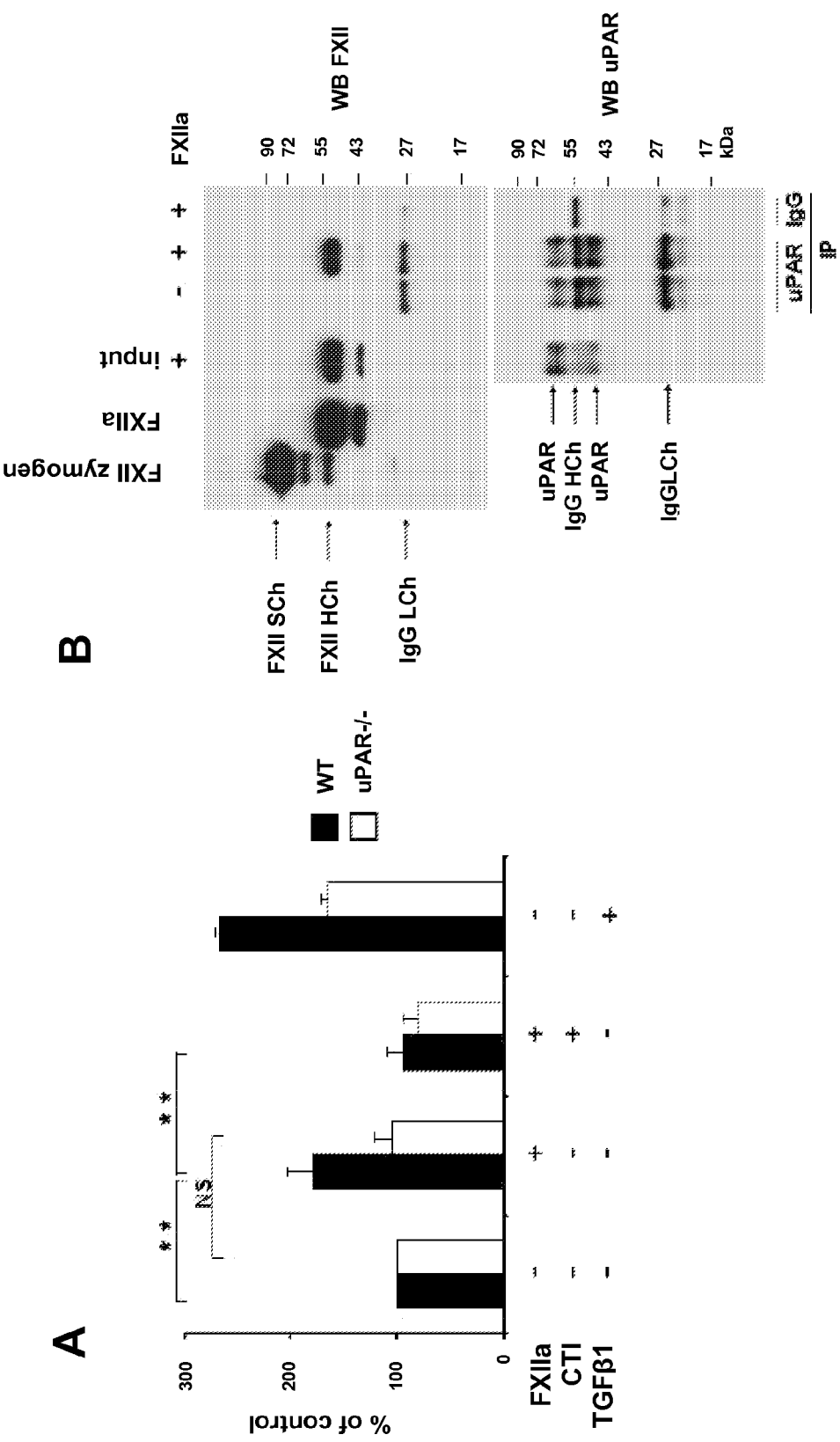
FIG. 14: uPAR is required for FXIIa mitogenic activities. (A) [$^3$H]-thymidine incorporation in murine lung fibroblasts isolated from wild type (WT) or uPAR deficient (uPAR-/-) mice after FXIIa stimulation. TGFβ exposure served as a positive control. CTI, Corn Trypsin Inhibitor. The values are presented as the mean±SEM of four determinations performed within one experiment of at least three. **P<0.0005; ANOVA, Tukey's post test. (B) Immunnoprecipitation of FXII. Antibodies specific for uPAR were incubated with lysates from cells either stimulated or unstimulated with FXIIa for 30 minutes. Immunocomplexes were precipitated using protein A-agarose beads and analyzed by Western blotting using antibodies against FXII. uPAR served as a loading control. IgG LCh, IgG light chain; IgGHCh, IgG heavy chain.
Figure 15:
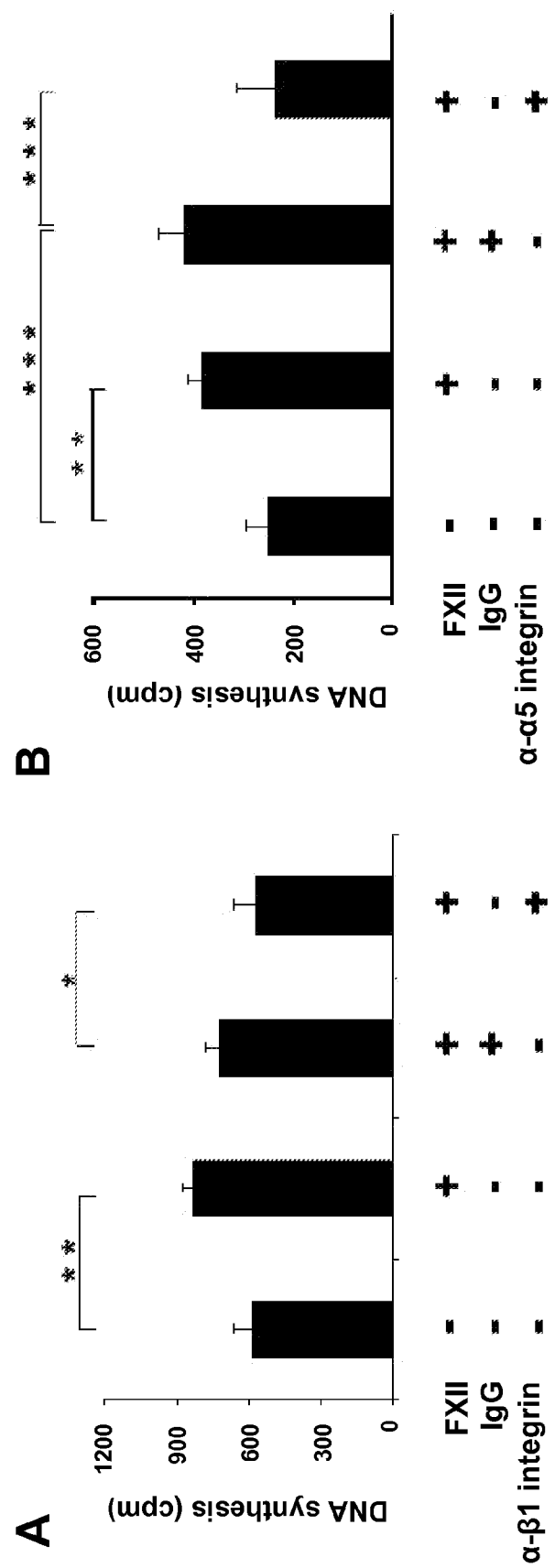
FIG. 15: α5β1 integrin regulates FXIIa mediated murine lung fibroblasts proliferation. (A) [$^3$H]-thymidine incorporation in murine lung fibroblasts preatreated with (A) β1 or (B) α5 integrin blocking antibodies or IgG isotype control prior to FXIIa stimulation. The values are presented as the mean±SEM of four determinations performed within one experiment of at least three. *p<0.0005; p<0.005; *p<0.05; ANOVA, Tukey's post test.

To confirm earlier findings, we isolated murine lung fibroblasts from uPAR deficient mice (uPAR-/-) and exposed them to FXIIa. In contrast to wild type cells, uPAR deffifcient lung fibroblasts did not response to FXIIa (FIG. 14A). These data indicates that uPAR is required for FXIIa mitogenic activities. This observation raised the question whether uPAR interacts with FXIIa protein. To investigate this issue, immunoprecipitation assay was performed. For immunoprecipitation, lysates were prepared from cells either stimulated or unstimulated with FXIIa for 30 min. Using anti-uPAR antibody FXII was immunoprecipitated from lysates of cells exposed to FXIIa. uPAR did not immunoprecipitated with isotype control antibody. Taken together, these results demonstrated that FXII induced murine lung fibroblasts proliferation in uPAR dependent manner. Based on the fact, that uPAR has no kinase activity and does not directly interact with intracellular pathways, the question whether other proteins are involved in in this mechanism was raised. It is unclear how glycosyl phosphatidylinositol-anchored uPAR, which lacks a transmembrane structure, mediates signal transduction. It has been proposed that uPAR forms cis-interactions with integrins as an associated protein and thereby transduces proliferative or migratory signals to cells upon binding of its ligand, urokinase. Studies using resonance energy transfer microscopy and co-immunoprecipitation with purified recombinant proteins indicate that uPAR forms complexes with a subset of β1- and β2-integrins and modulates the signaling capacity of these molecules. Based on these reports and our own studies, showing increased adhesion of fibroblasts to fibronectin after FXIIa stimulation, it was investigated whether fibronectin receptor α5β1 integrin influences FXII mitogenic activities. Pretreatment of lung fibroblasts with α5 or β1 integrin blocking antibodies abolished [3H]-thymidine incorporation after exposure to FXII, while IgG control antibody had no effect (FIG. 15). This observation suggests that α5β1 integrin is involved in FXIIa-induced murine lung fibroblasts proliferation.

TGF-β1 regulates FXII Expression in Human Lung Fibroblasts.

TGF-β1 Upregulates FXII mRNA and Protein Levels in HLF.

Figure 16:
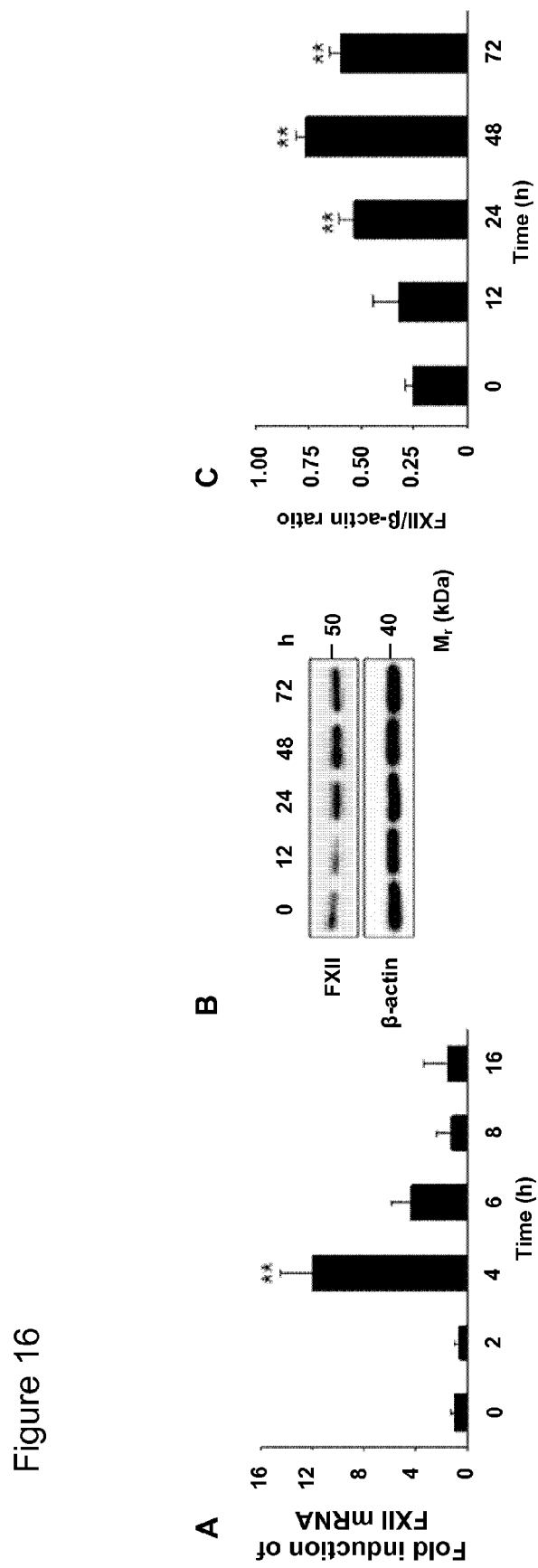
FIG. 16: TGF-β1 upregulates FXII expression in HLF. (A, B) Time course of FXII expression in HLF following TGF-β1 stimulation as assessed by (A) real time PCR and (B) western blotting. Real time PCR results are expressed as the fold-increase in FXII expression (normalized for β-actin expression) versus values obtained for unstimulated cells, and are mean±SD; n=3; p<0.01. A representative blot out of three is illustrated. (C) Densytometric analysis of the blot presented in (B); p<0.01.

Exposure of HLF to 10 ng/ml TGF-β1 stimulated the synthesis of FXII in a time dependent manner. Real time RT-PCR analysis demonstrated the strongest induction of FXII mRNA expression 4 h after treatment (FIG. 16A). The maximal FXII protein level was achieved within 48 h stimulation period and slightly decline over 72 h (FIG. 16B, C). Immunofluorescence staining revealed pronounced expression of FXII in response to TGF-β1. FXII was detected on the cell surface, as well as in the cytoplasmic compartment of HLF. The purity of isolated HLF was verified by positive staining for fibronectin, vimentin, and collagen IV.

TGF-β1 Induces Phosphorylation of MAPK, Akt and Smad3.

Figure 17:
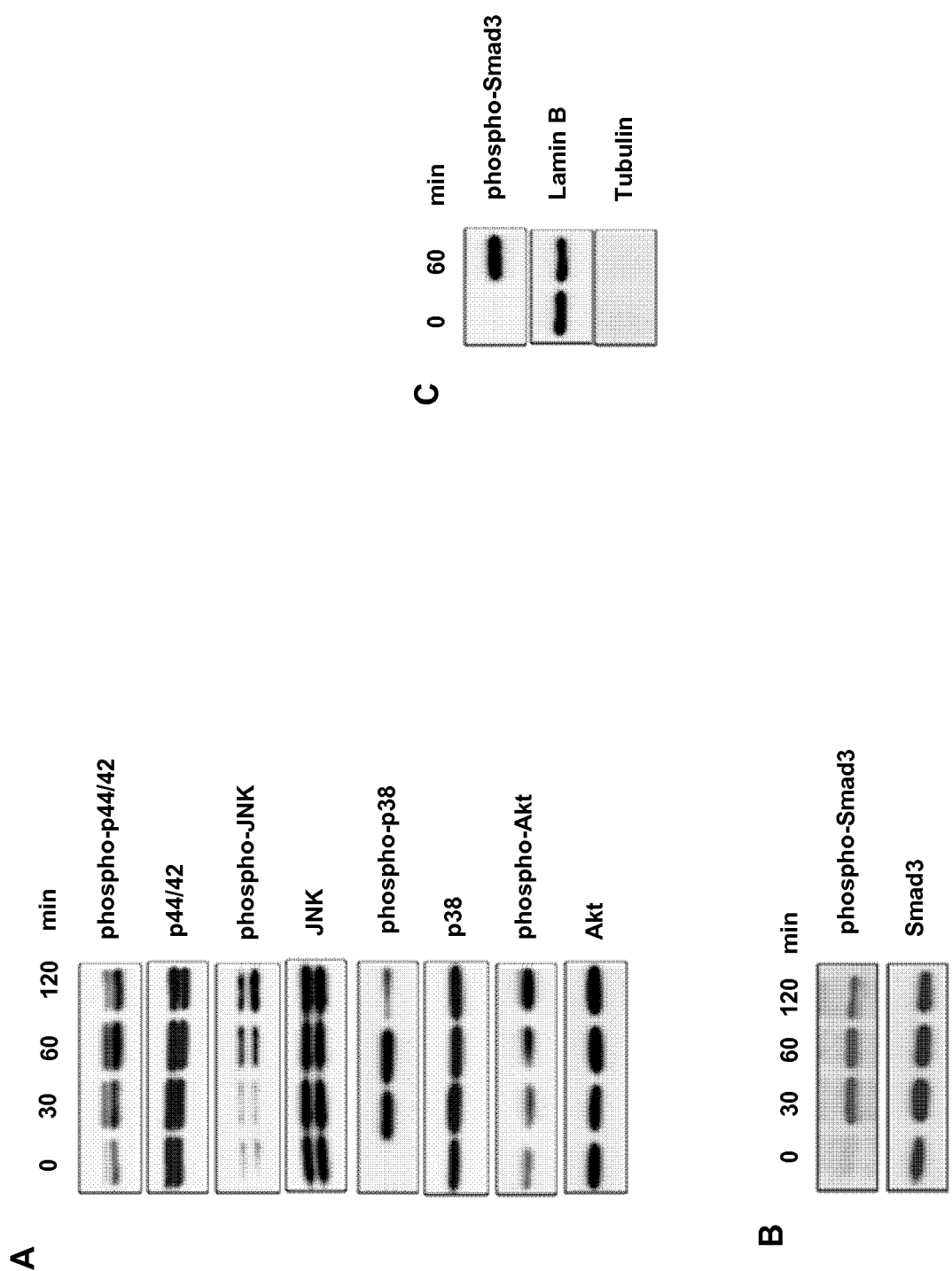
FIG. 17: TGF-β1 induces phosphorylation of MAPK, Akt and Smad3. (A) HLF were treated for the indicated time points with TGF-β1 and the activity and expression of p44/42, JNK, p38 and Akt kinases were analyzed by Western blotting. Phosphoproteins were detected via phospho-specific antibodies as indicated. Equal loading was confirmed via pan-specific antibodies. Data are representative of four independent experiments. (B) TGF-β1 dependent translocation of phospho-Smad 3 to the nucleus. HLF were incubated with TGF-β1 for 1 h then washed, fixed and stained with phospho-Smad 3 antibody. Arrows indicate nuclear localisation of Smad 3. Original magnification 40'/1.25-0.75 oil-objective. Bar size 10 µm. Data are representative of three independent experiments. (C) Western blot analysis of TGF-β1 driven translocation of phospho-Smad 3 to the nucleus. HLF were treated for 1 h with TGF-β1, nuclear extracts were prepared and immunoblotted with antibodies against phospho-Smad 3, lamin B, and tubulin. Lamin B was used as a loading control and tubulin to assess the purity of the nuclear fraction. Data are representative of three independent experiments.

To dissect the contribution of different signal transduction pathways to TGF-β1-induced FXII production in HLF, MAPKs, Akt, and Smad phosphorylation kinetics in response to TGF-β1 stimulation were analyzed. Phosphorylation of p42/44 and p38 kinases reached a peak at 60 min, and then gradually decreased. A marked increased in JNK activity was visible after 60 min, whereas enhanced phosphorylation of Akt was noted after 120 min (FIG. 17A). As expected, TGF-β1 induced rapid phosphorylation of Smad 3 with maximal response within 30-60 min (FIG. 17B). No activation of c-jun was detectable (data not shown). Immunofluorescence analysis demonstrated TGF-β1 induced translocation of phospho-Smad 3 to the nucleus. Accordingly increased levels of phospho-Smad 3 were observed in the nuclear extracts after TGF-β1 treatment (FIG. 17C). Lamin B was used as a loading control and tubulin to assess the purity of the nuclear fraction.

Smad 3 and JNK Kinase Regulate TGF-β1-induced FXII Expression in HLF.

Figure 18:
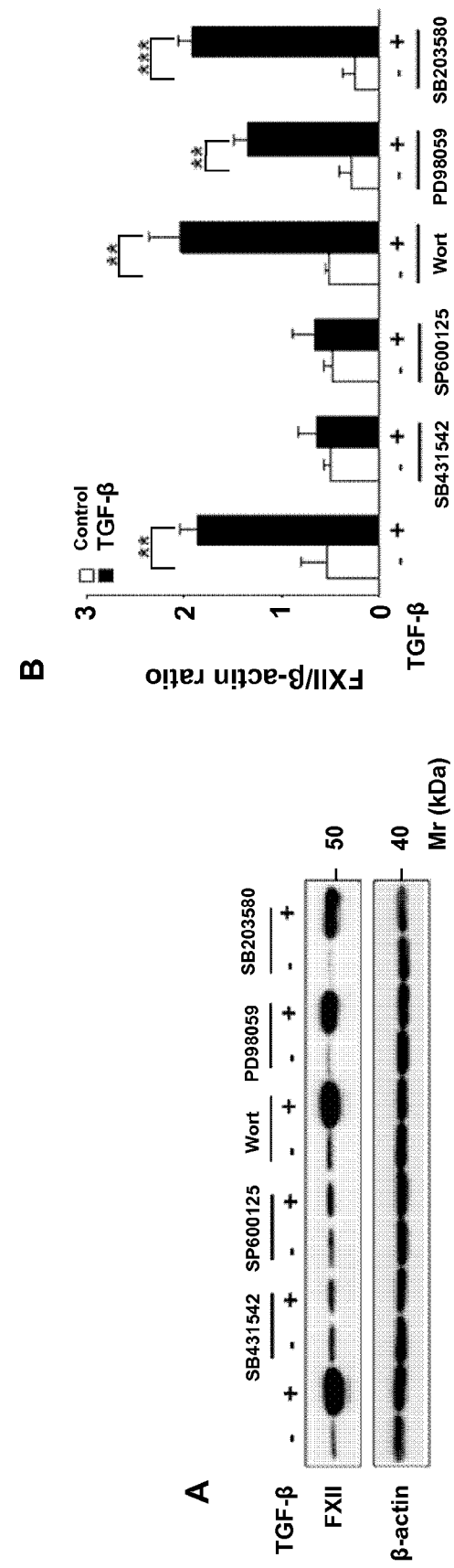
FIG. 18: Smad 3 and JNK kinase regulate TGF-β1-induced FXII expression in HLF. (A) Western blot analysis of TGF-β1 induced FXII expression in HLF. HLF were treated with SB431542, SP600125, Wortmannin (Wort), PD98059, or SB203580 for 1 h prior to incubation with TGF-β1 for 48 h. Cell lysates were prepared and FXII expression was examined. β-actin was used as a loading control. A representative blot out of three is illustrated. (B) Densytometric analysis of the blot presented in (A); p<0.01; *p<0.001. (C, F) Determination of knockdown efficiency in HLF by siRNA transfection against (C) JNK1 or (F) Smad 3 by Western blotting. Data are representative of three independent experiments. (D, G) Effect of (D) JNK1 or (G) Smad 3 knockdown on TGF-β1 induced FXII expression in HLF. Data are representative of three independent experiments. (E, H) Densytometric analysis of the blots presented in (D) and (G), respectively; *p<0.05; p<0.01, *p<0.001. siR, scrumble siRNA; wort, wortmannin.
Figure 18:
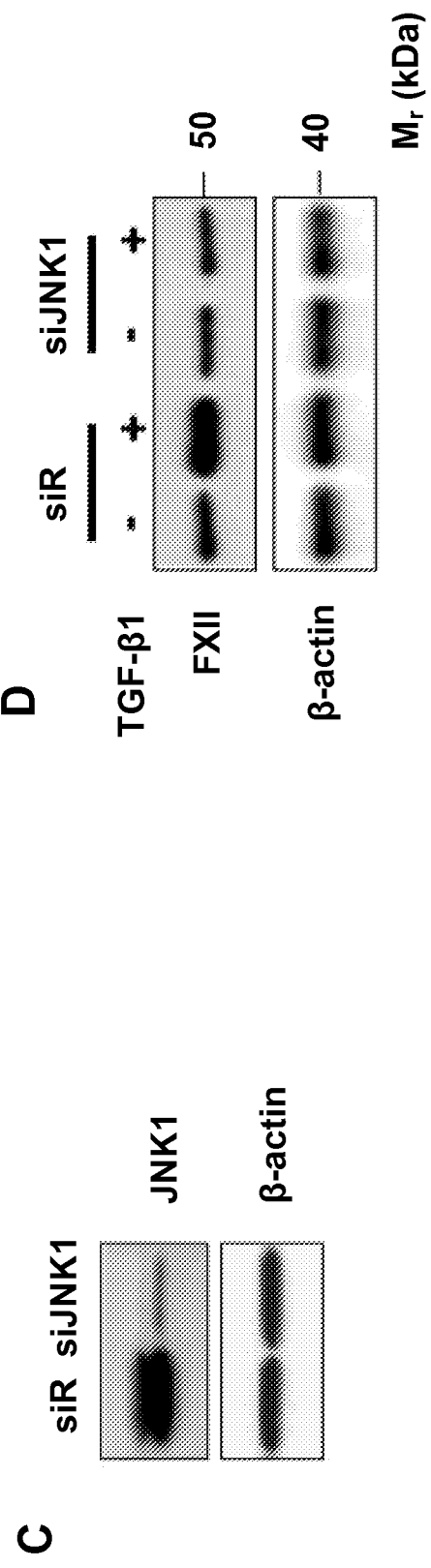
Figure 18:
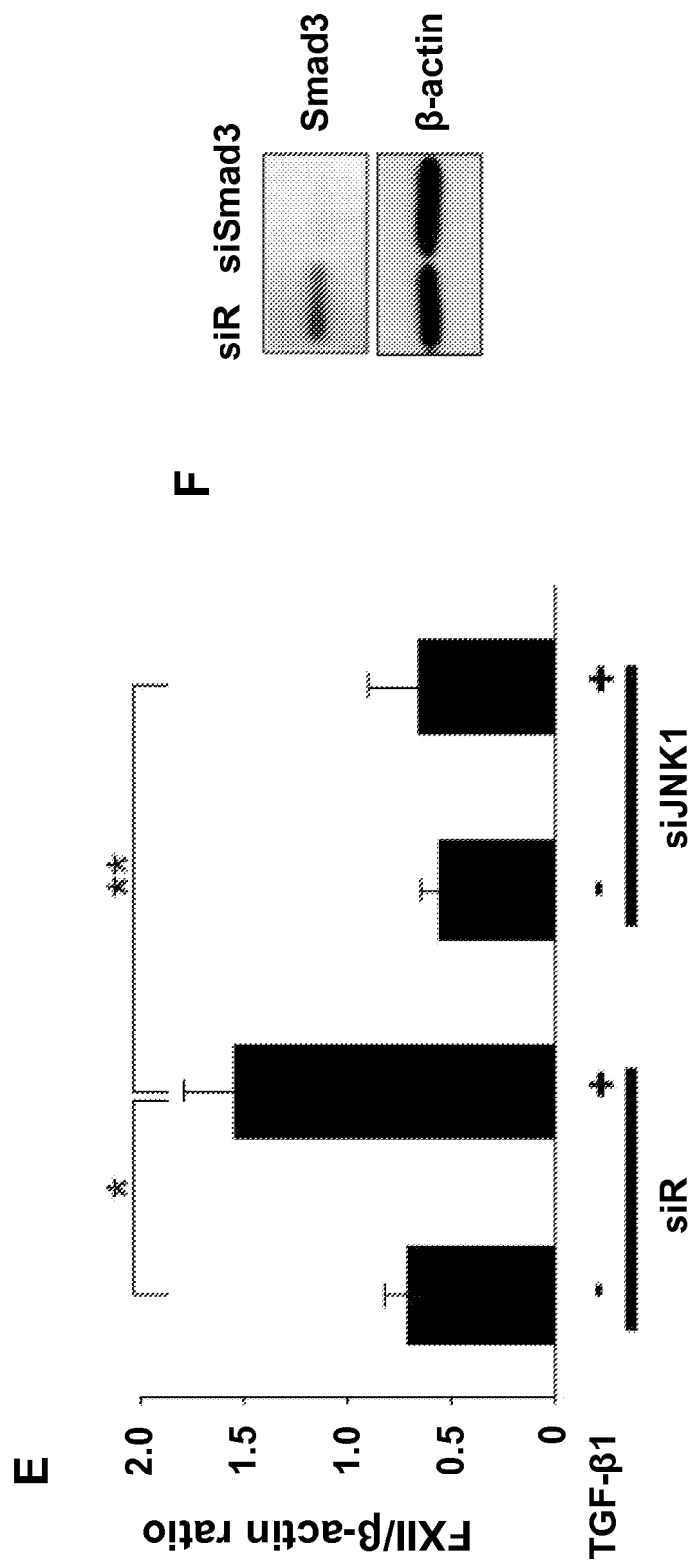
Figure 18:
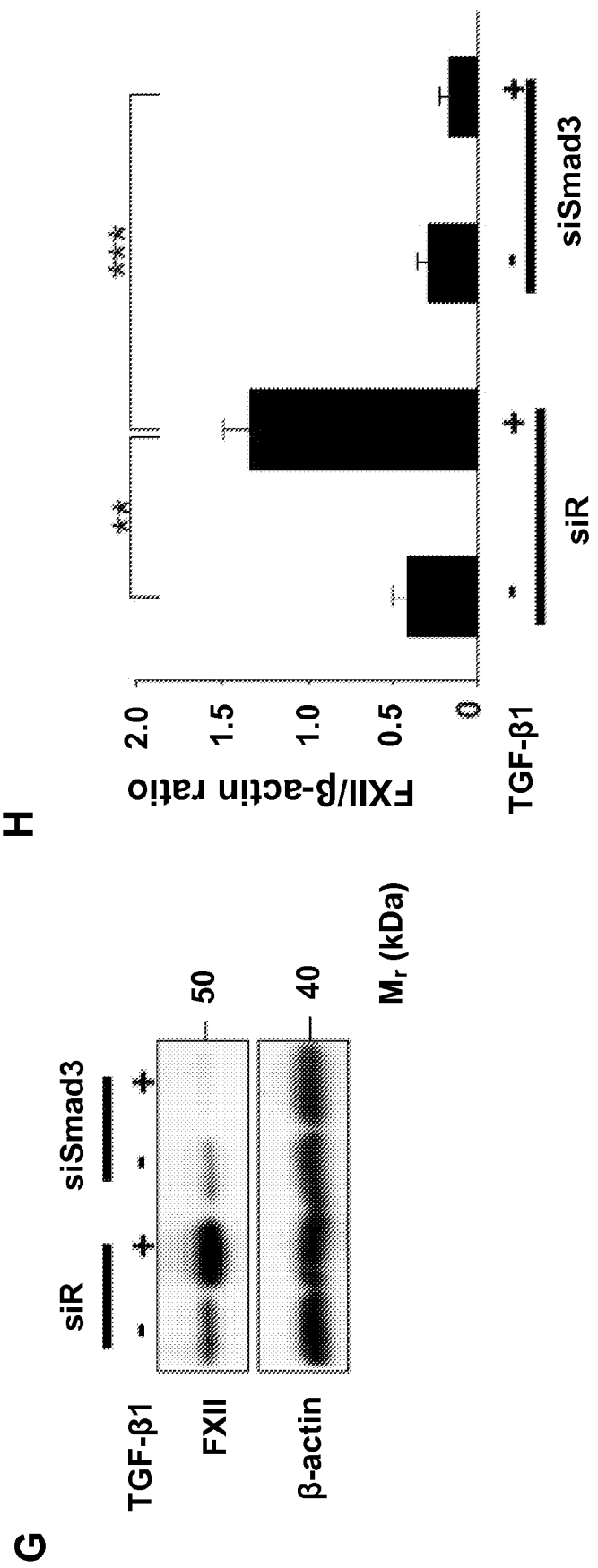

After determination of the phosphorylation kinetics, we next sought to analyse whether interference with these pathways would affect TGF-β1-induced FXII expression in HLF. To characterize this, specific inhibitors of TβRI, JNK, PI3K, MEK and p38 kinases (SB431542, SP600125, Wortmannin, PD98059, and SB203580, respectively) were used and their effect on TGF-β1 stimulated expression of FXII was evaluated. As depicted in FIG. 18A, B inhibition of TβRI and JNK activity by SB431542 and SP600125, respectively, led to reduction of FXII expression in response to TGF-β1. No change in FXII expression was visible when HLF were pretreated with inhibitors of Akt, p44/42, and p38 kinases. To further confirm these results, HLF were transfected with JNK1- or Smad 3-specific siRNAs, which caused significant knock-down of these proteins as demonstrated by Western blotting (FIG. 18C, F). As shown in FIGS. 18D and E, knockdown of JNK1 resulted in inhibition of FXII expression after TGF-β1 stimulation. Similar results were obtained when Smad 3 was depleted (FIG. 18G, H).

JNK Kinase does not Regulate Smad3 Phosphorylation and Translocation to the Nucleus.

Figure 19:
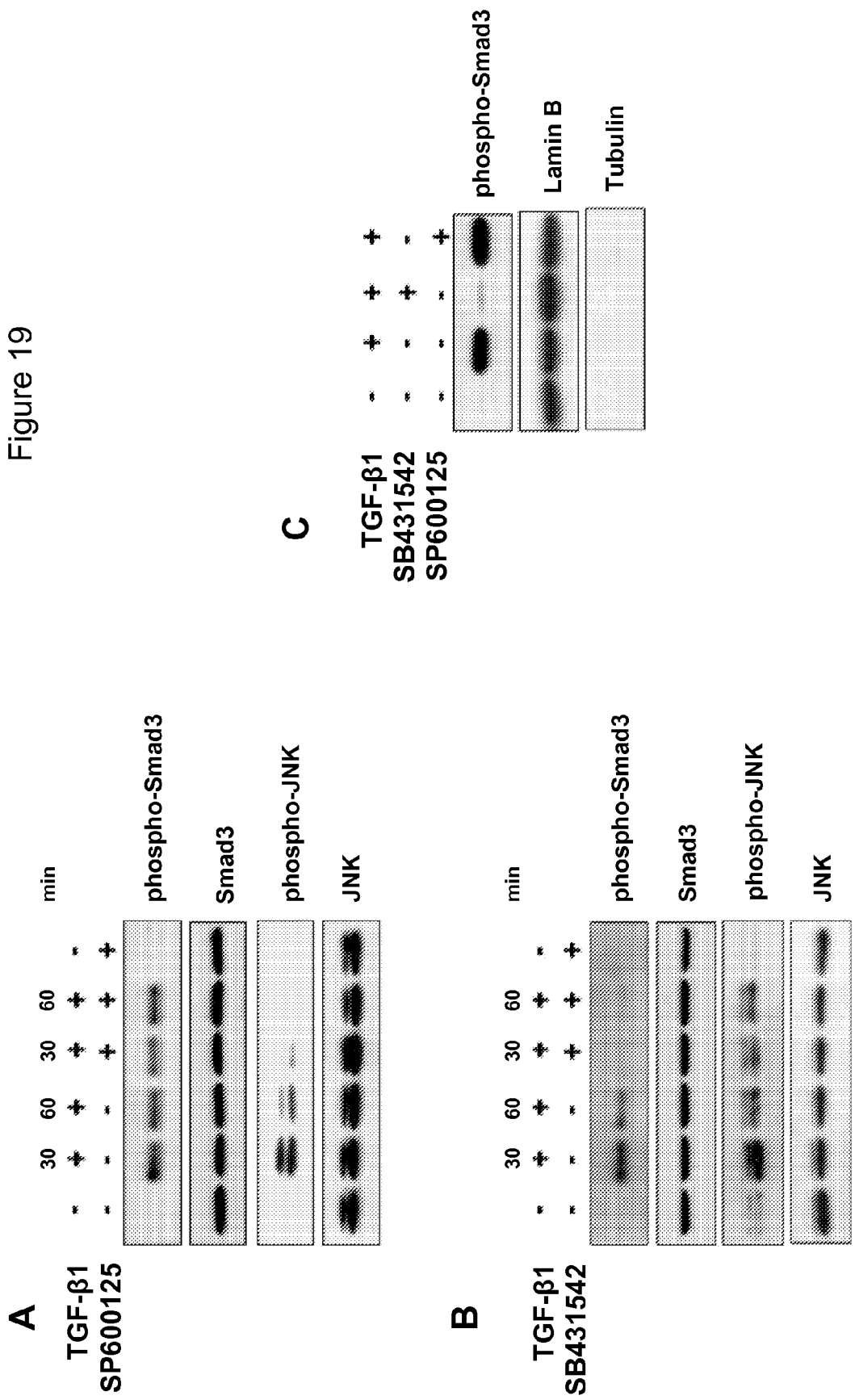
FIG. 19: JNK1 kinase does not regulate Smad3 phosphorylation and translocation to the nucleus. (A, B) HLF were treated with TGF-β1 in the absence or presence of (A) JNK inhibitor (SP600125) or (B) TβRI inhibitor (SB431542), as indicated, and the activity and expression of Smad 3 and JNK were analyzed by Western blotting. Data are representative of four independent experiments. (C) Western blot analysis of TGF-β1 driven translocation of phospho-Smad 3 to the nucleus. HLF were pretreated with SB431542 or SP600125 and then either unstimulated or stimulated for 1 h with TGF-β1, nuclear extracts were prepared and immunoblotted with antibodies against phospho-Smad 3, lamin B, and tubulin. Lamin B was used as a loading control and tubulin to assess the purity of the nuclear fraction. Data are representative of three independent experiments.

In next experiments the role of JNK kinase in Smad3 phosphorylation and translocation to the nucleus was investigated. Incubation of HLF with JNK inhibitor (SP600125) did not reduced Smad 3 phosphorylation, but completely abolished JNK activity (FIG. 19A). TβRI inhibitor (SB431542) attenuated phosphorylation of Smad 3 and JNK1 in response to TGF-β1, indicating that phosphorylation of Smad 3 and JNK originates from TβRI, the most proximal molecule in TGF-β1 signal transduction pathway (FIG. 19B). Furthermore, exposure of HLF to SP600125 had no effect on TGF-β1-induced Smad 3 translocation to the nucleus, whereas SB431542 completely blocks this process (FIG. 19C). Similar results were obtained by immunofluorescence analysis. SB431542 and SP600125 alone did not affect accumulation of Smad 3 in the nucleus (data not shown). These results indicate that JNK kinase can regulate TGF-β1 induced FXII expression in the absence of any effects on phosphorylation and translocation of Smad 3 to the nucleus.

TGF-β1 Induces FXII Promoter Activity via SBE Located at the Position -272.

Figure 20:
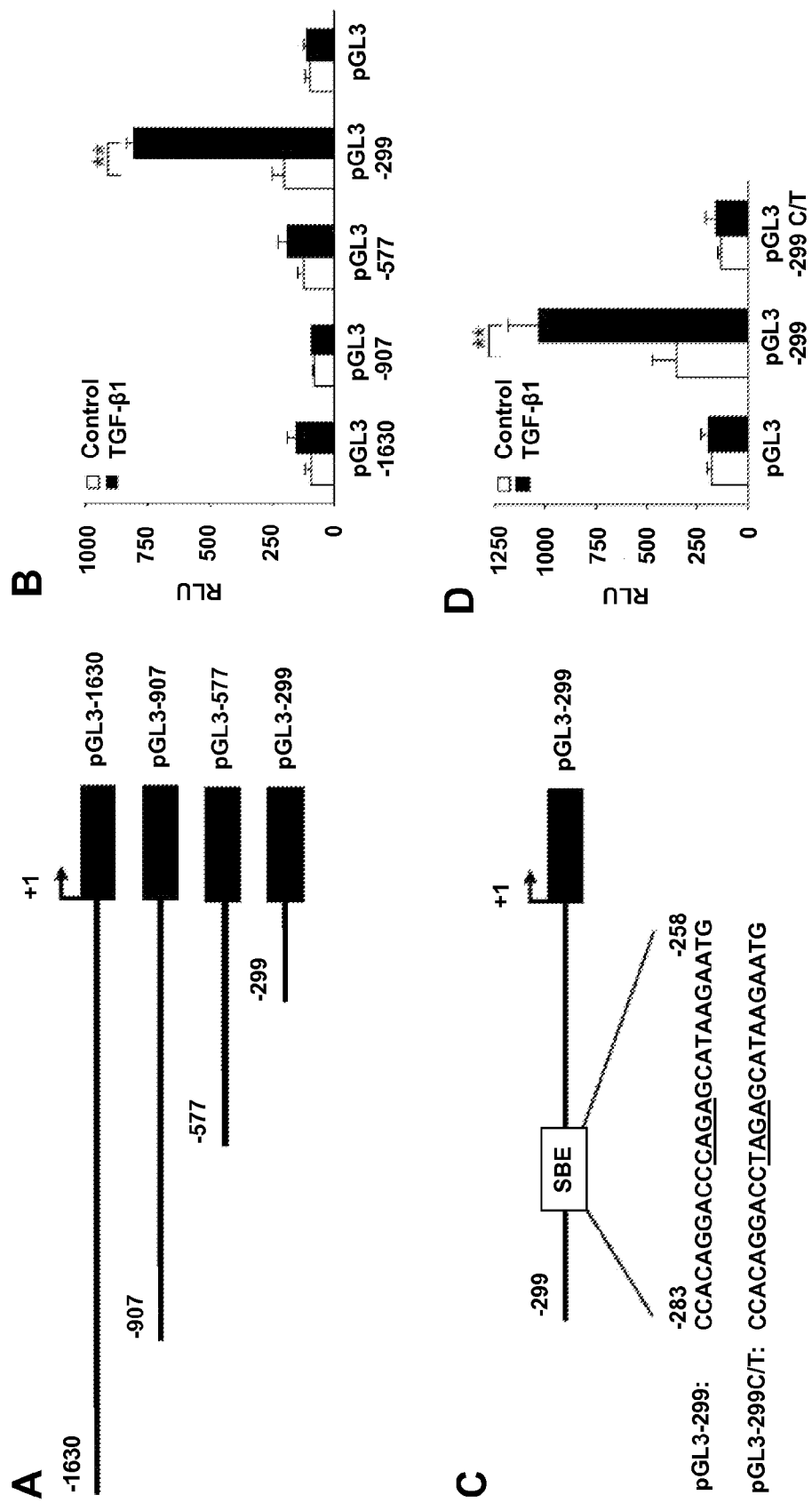
FIG. 20: TGF-β1 induces FXII promoter activity via SBE located at the position -272. (A) Schematic representation of FXII promoter deletion luciferase reporter constructs. Angled arrow indicates the transcription start site. (B) NIH3T3 cells were transfected with the indicated FXII promoter deletion constructs and then either unstimulated (white bars) or stimulated with TGF-β1 (black bards). Luciferase activity was measured as described in "Experimental procedures". Data represent mean values±SD from four independent experiments, each performed in triplicate; p<0.01. (C) Schematic representation of FXII promoter region containing putative smad binding site (SBE) at the position -272. pGL3-299 C/T represents a construct in which the SBE-272 was mutated by the replacement of C residue at the position -273 by T. (D) NIH3T3 cells were transfected with the pGL3-299 or pGL3-299 C/T constructs. Luciferase activity was determined in untreated (white bars) and TGF-β1 treated (black bards) cells. Data represent mean values±SD from four independent experiments, each performed in triplicate; p<0.01.

To identify DNA elements required for TGF-β1 induced FXII production, NIH3T3 cells were transiently transfected with a series of human FXII promoter deletion constructs (−1630 bp; −907 bp; −577 bp; −299 bp; FIG. 20A) and then luciferase activity in untreated and TGF-β1 treated cells was measured. NIH3T3 cells were used in these studies due to their high transfection efficiency. Cells transfected with pGL3-1630; pGL3-907; and pGL3-577 constructs displayed no increase in luciferase activity in response to TGF-β1, whereas strong induction of FXII promoter activity was observed in pGL3-299 transfected cells (FIG. 20B). These results indicate the presence of TGF-β1 responsive element within −299/+1 bp in the human FXII promoter. In addition, the data suggests that repressor element(s) located in the region upstream of -299 bp may dampen the stimulatory effects of TGF-β1.

Figure 21:
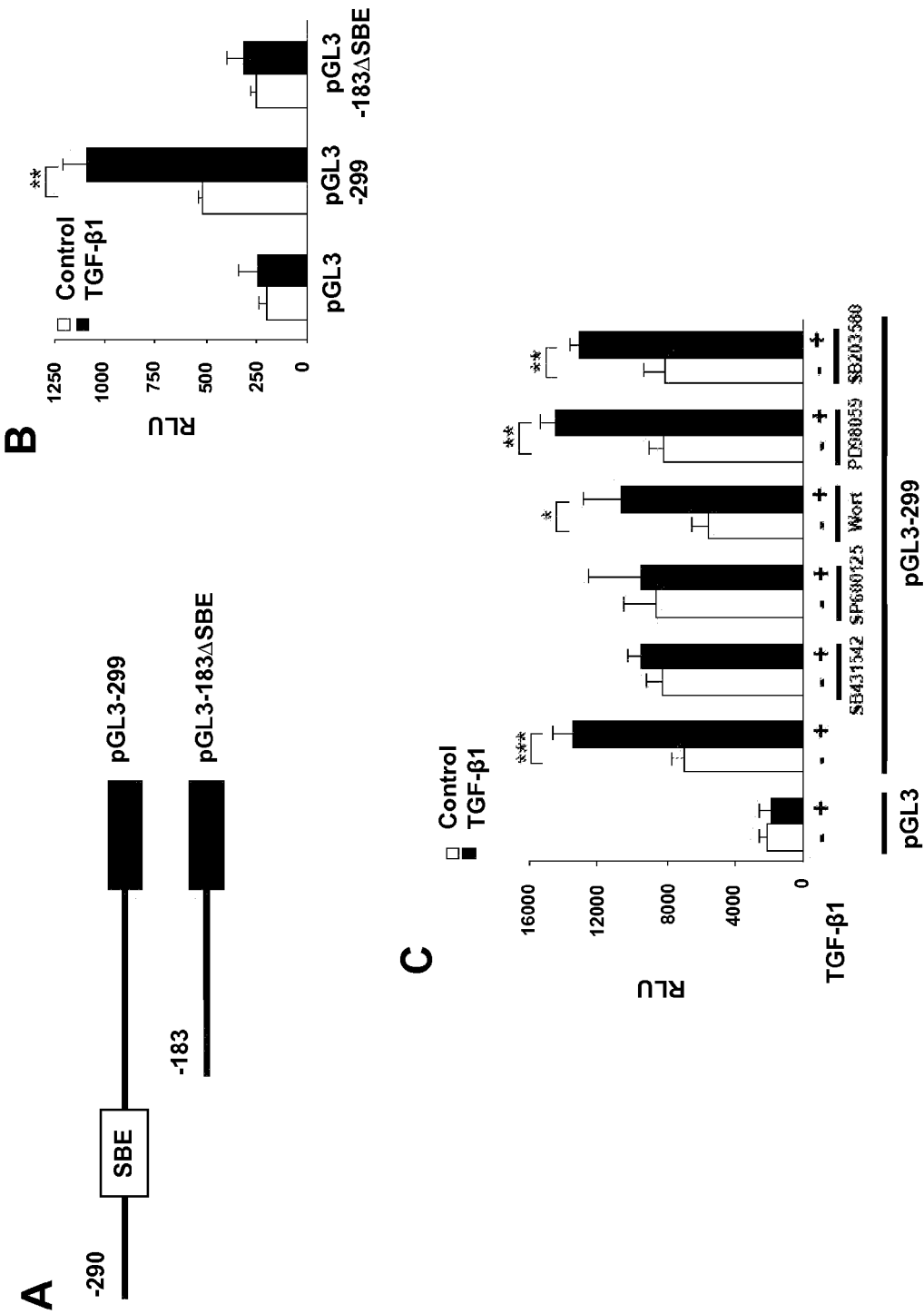
FIG. 21: TGF-β1 induces FXII promoter activity via SBE located at the position -272. (A) Schematic representation of pGL3-299 construct and a construct lacking SBE-272 (pGL3-183DSBE-272). (B) NIH3T3 cells were transfected with pGL3-299 or pGL3-183DSBE-272 and the luciferase activity was measured in unstimulated (white bars) and TGF-β1 stimulated (black bards) cells. Data represent mean values±SD from three independent experiments, each performed in triplicate; **p<0.01. (C) NIH3T3 cells, transfected with pGL3-399 construct, were pretreated with SB431542, SP600125, Wortmannin (Wort), PD98059, or SB203580 for 1 h prior to incubation with TGF-β1. Luciferase activity was determined in untreated (white bars) and TGF-β1 treated (black bards) cells. Data represent mean values±SD from three independent experiments, each performed in triplicate; *p<0.05; p<0.01; *p<0.001. wort, wortmannin.

To identify TGF-β1-responsive element of FXII promoter lying between -299/+1 bp, this DNA region was examined for consensus smad binding elements (SBEs). This analysis identified the putative SBE at the position -272 by (SBE-272, FIG. 20C). As expected, the point mutation of SBE-272 completely abolished FXII promoter activity in response to TGF-β1 (FIG. 20D). To confirm these results, a construct lacking SBE-272 was generated (FIG. 21A). Deletion of sequence between -299 and -183 abrogated the ability of FXII promoter to confer responsiveness to TGF-β1 (FIG. 21B). Similar results were observed when primary HLF were used (data not shown). Next, the role of JNK/Smad 3 signaling pathways in the regulation of FXII expression was tested by gene luciferase activity assay. The cells were transfected with pGL3-299 construct, pretreated with indicated inhibitors, and then either unstimulated or stimulated with 10 ng/ml TGF-β1. As depicted in FIG. 21C TGF-β1 driven luciferase activity was strongly reduced only in the presence of SB431542 and SP600125 inhibitors.

Smad 3 Interacts with SBE-272 within FXII Promoter.

Figure 22:
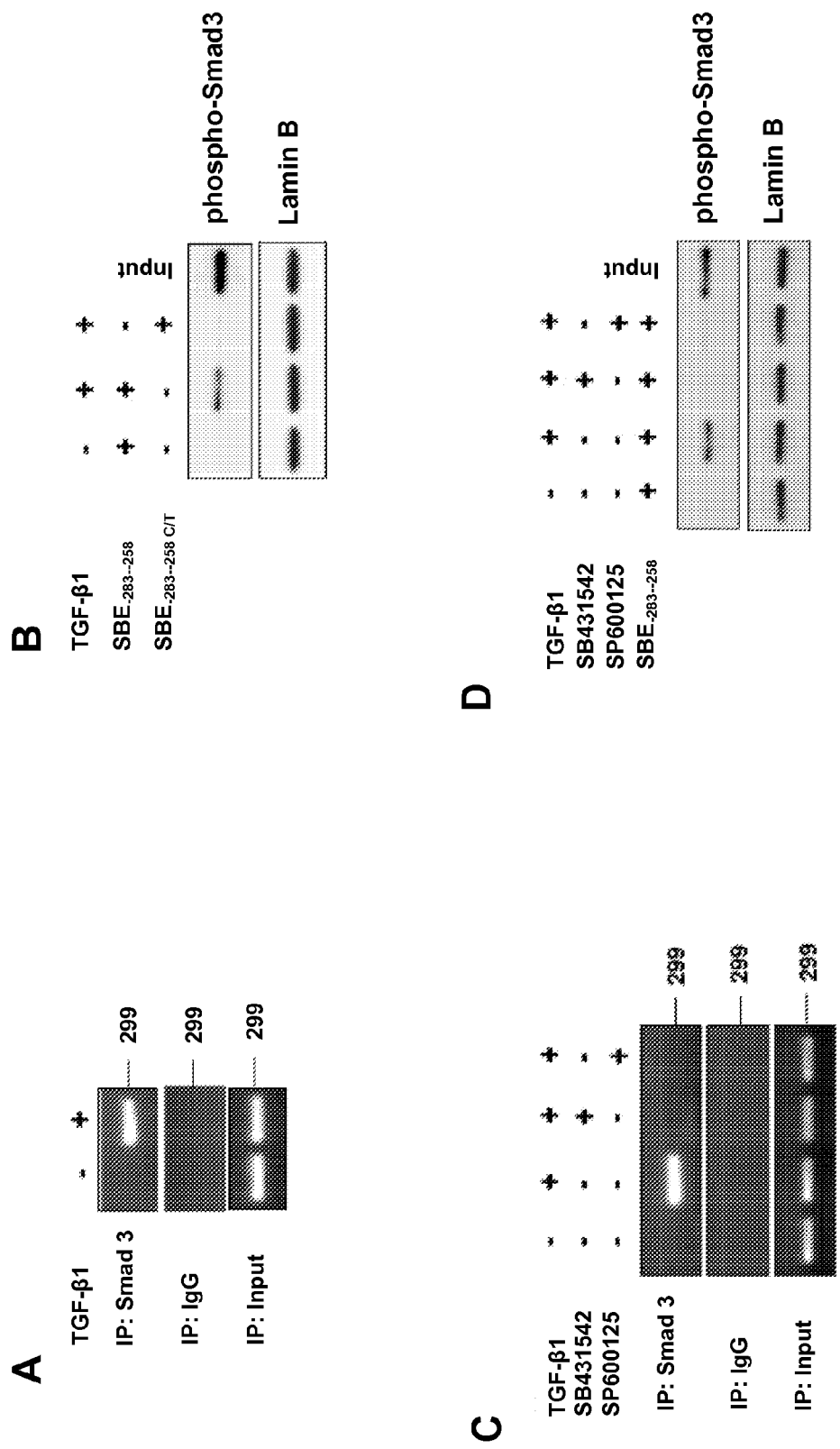
FIG. 22: Smad 3-SBE-272 interaction is suppressed in the presence of JNK inhibitor. (A) HLF were either unstimulated or stimulated with TGF-β1 and ChIP analysis was performed using Smad 3 antibody or isotype IgG control. PCR was performed with immunoprecipitated DNA as described in "Experimental procedures". PCR product were separated by agarose gel electrophoresis and detected by staining with ethidium bromide. Data are representative of three independent experiments. (B) Nuclear extracts from untreated or TGF-β1 treated cells were incubated with biotinylated templates (SBE-283/-258 or SBE-283/-258 C/T) and Smad 3 was detected by Western blotting. Data are representative of three independent experiments. (C) HLF were pretreated with SB431542 or SP600125 for 1 h prior to incubation with TGF-β1. ChIP analysis was performed using Smad 3 antibody or isotype IgG control. PCR was performed with immunoprecipitated chromatin as described in "Experimental procedures". Data are representative of three independent experiments. (D) HLF were preincubated with SB431542 or SP600125 for 1 h prior to addition of TGF-β1. Nuclear extracts were prepared and then incubated with biotinylated template (SBE-283/-258). Smad 3 was detected by Western blotting. Data are representative of three independent experiments.
Figure 23:
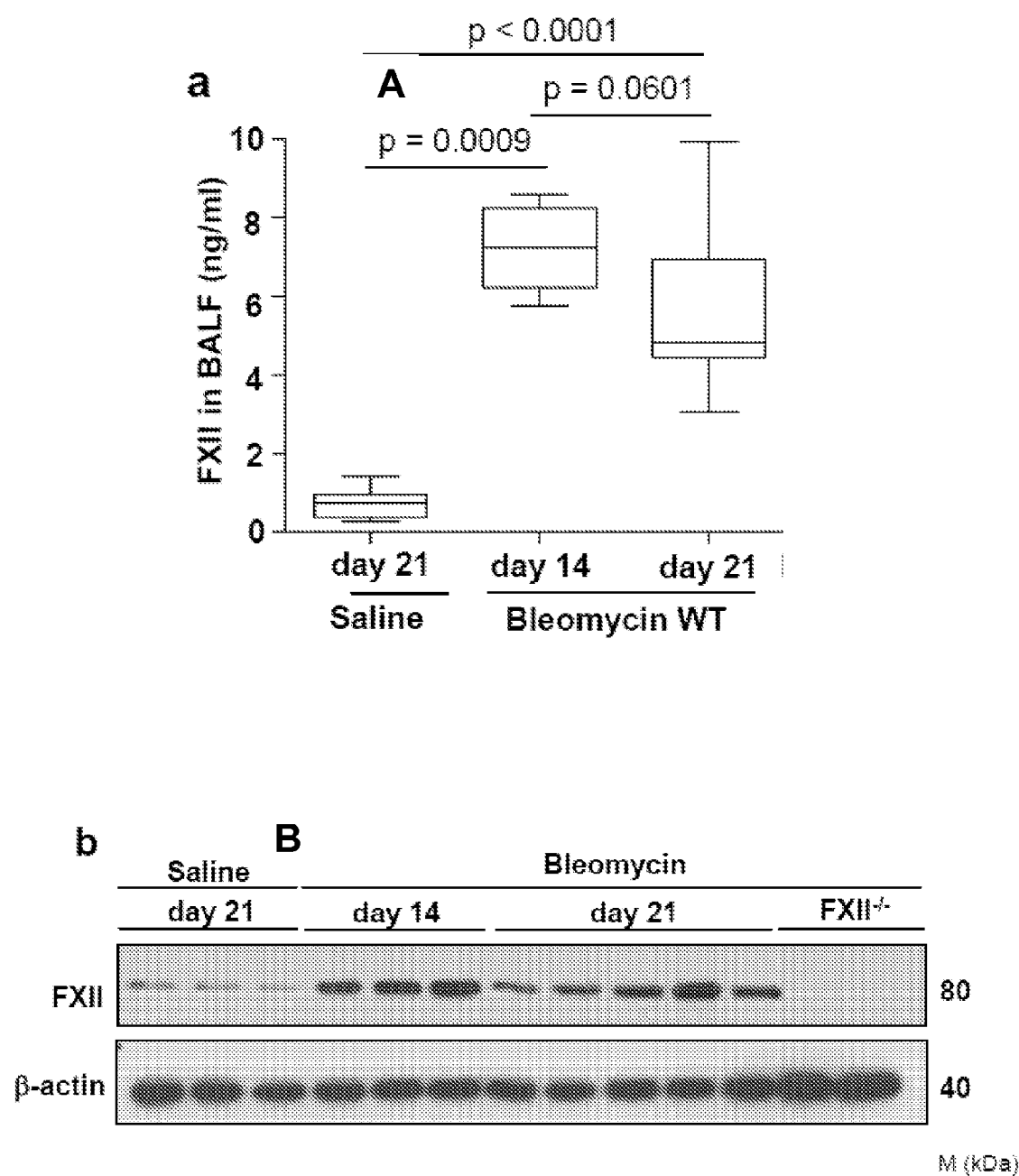
FIG. 23: Expression and distribution of FXII in experimental lung fibrosis in mice. (A) Bleomycin application was used to induce an idiopathic pulmonary fibrosis (IPF) type disease in mice, and the concentration of FXII in the bronchoalveolar lavage fluid of treated animals was quantified. (B) The expression of FXII (Western Blot analysis) in mice lung on day 14 and day 21 mice following treatment with bleomycin is shown. (C) The expression of FXII mRNA in relation to β-actin mRNA in bleomycin-treated mice is shown, also indicating the fold-increase on day 14 and day 21 following bleomycin application. (D,E) The tissue architecture and the distribution of FXII (red colour) in bleomycin-treated mice are demonstrated.
Figure 23:
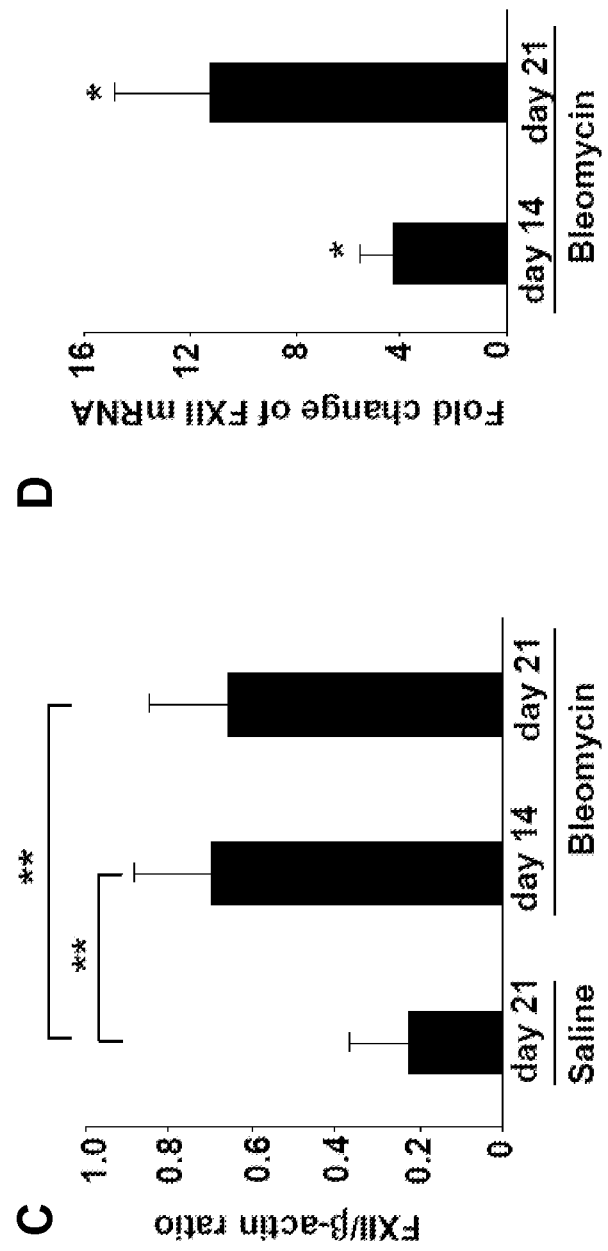
Figure 23:
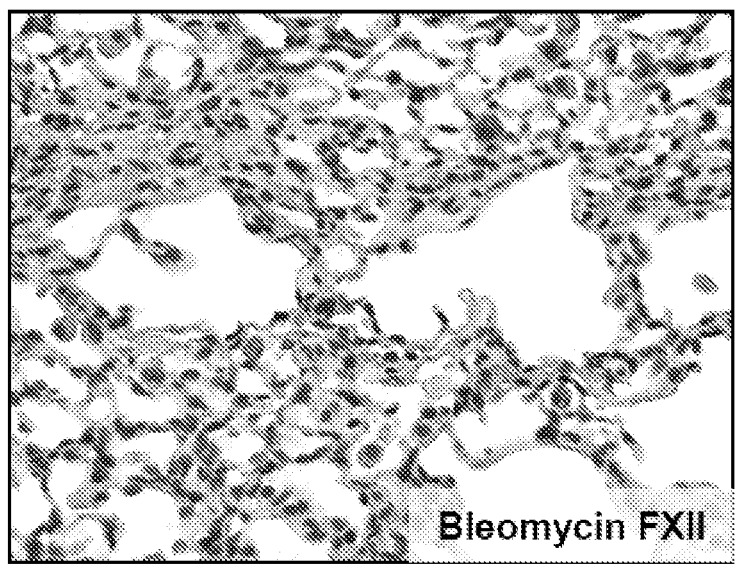
Figure 23:
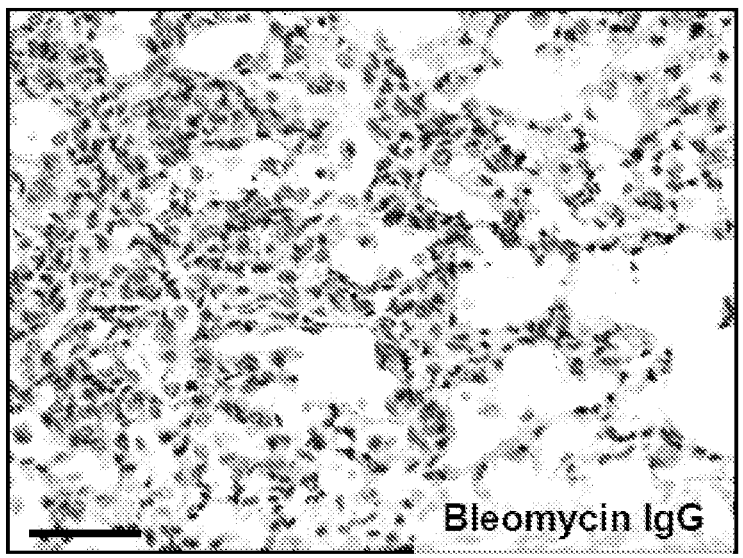
Figure 24:
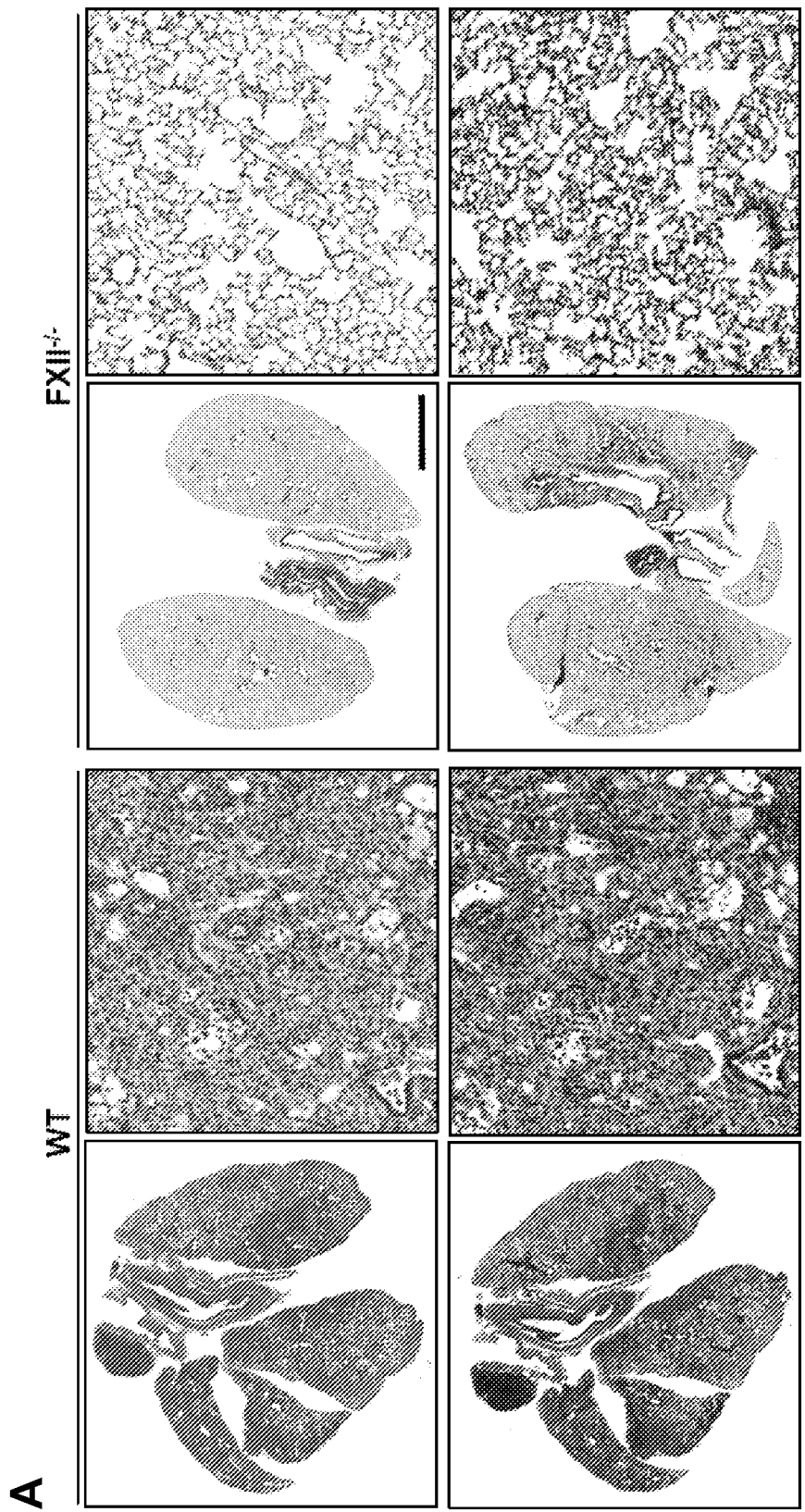
FIG. 24: Influence of FXII deficiency on bleomycin-induced IPF in mice. (A) The distribution of factor XII (red colour) in wild-type (WT) and FXII-deficient animals is shown. Also, the distribution of collagen deposits is documented. Note: In FXII-deficient mice the lung tissue architecture is hardly affected and resembles the physiological situation, no major collagen deposits are visible. (B) The survival curves (Kaplan-Meier plot) of wild-type mice as compared to FXII-deficient mice are documented for the bleomycin-treated groups. (C) The compliance of lung function of bleomycin-treated wild-type or FXII-deficient mice is documented, indicating an almost complete protection of FXII-deficient mice against the IPF situation. (D,E) The septum thickness as well as the collagen content is not enlarged in bleomycin-treated FXII-deficient mice as compared to the wild-type group.
Figure 24:
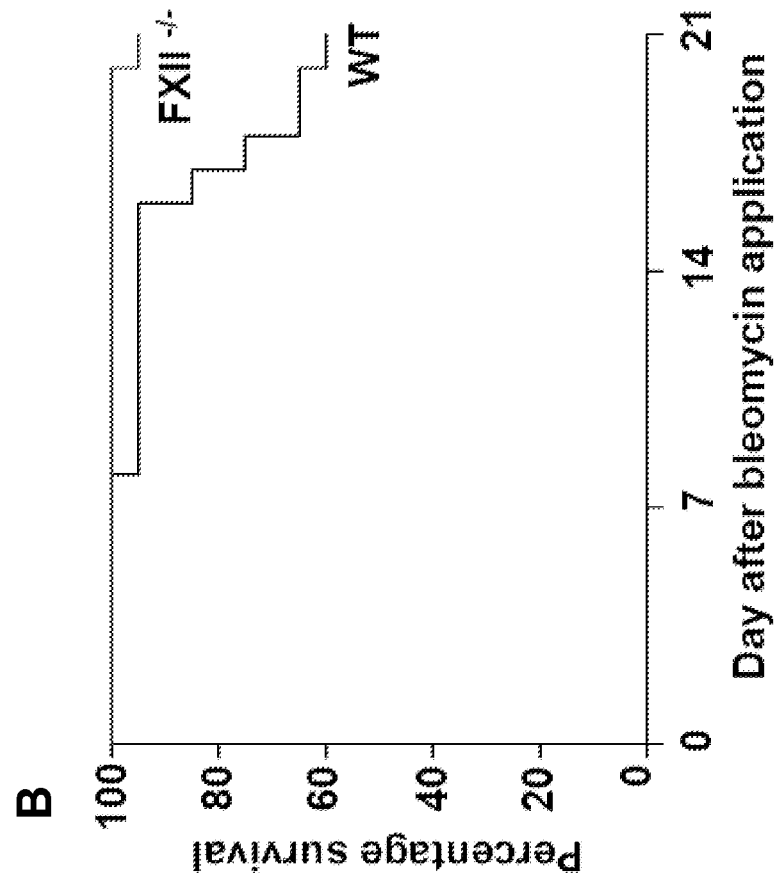
Figure 24:
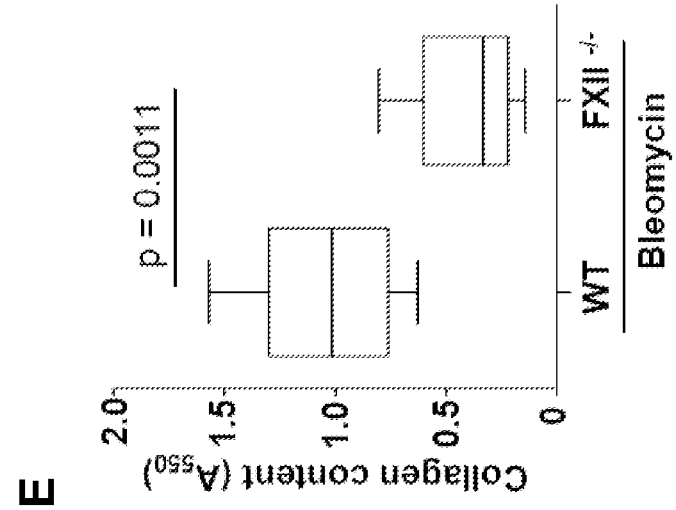
Figure 24:
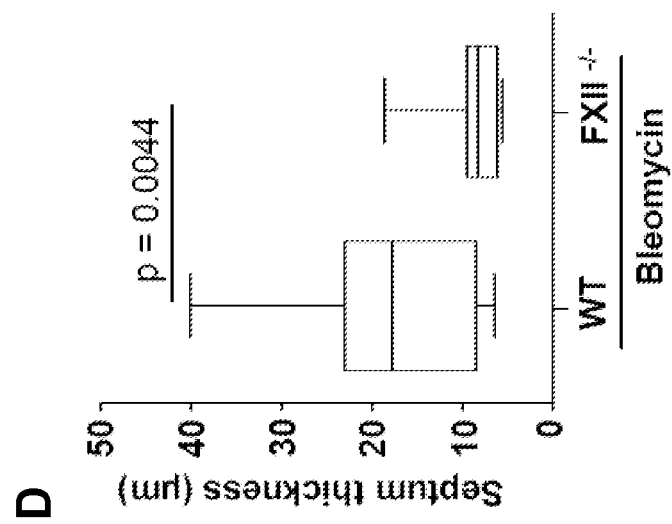
Figure 25:
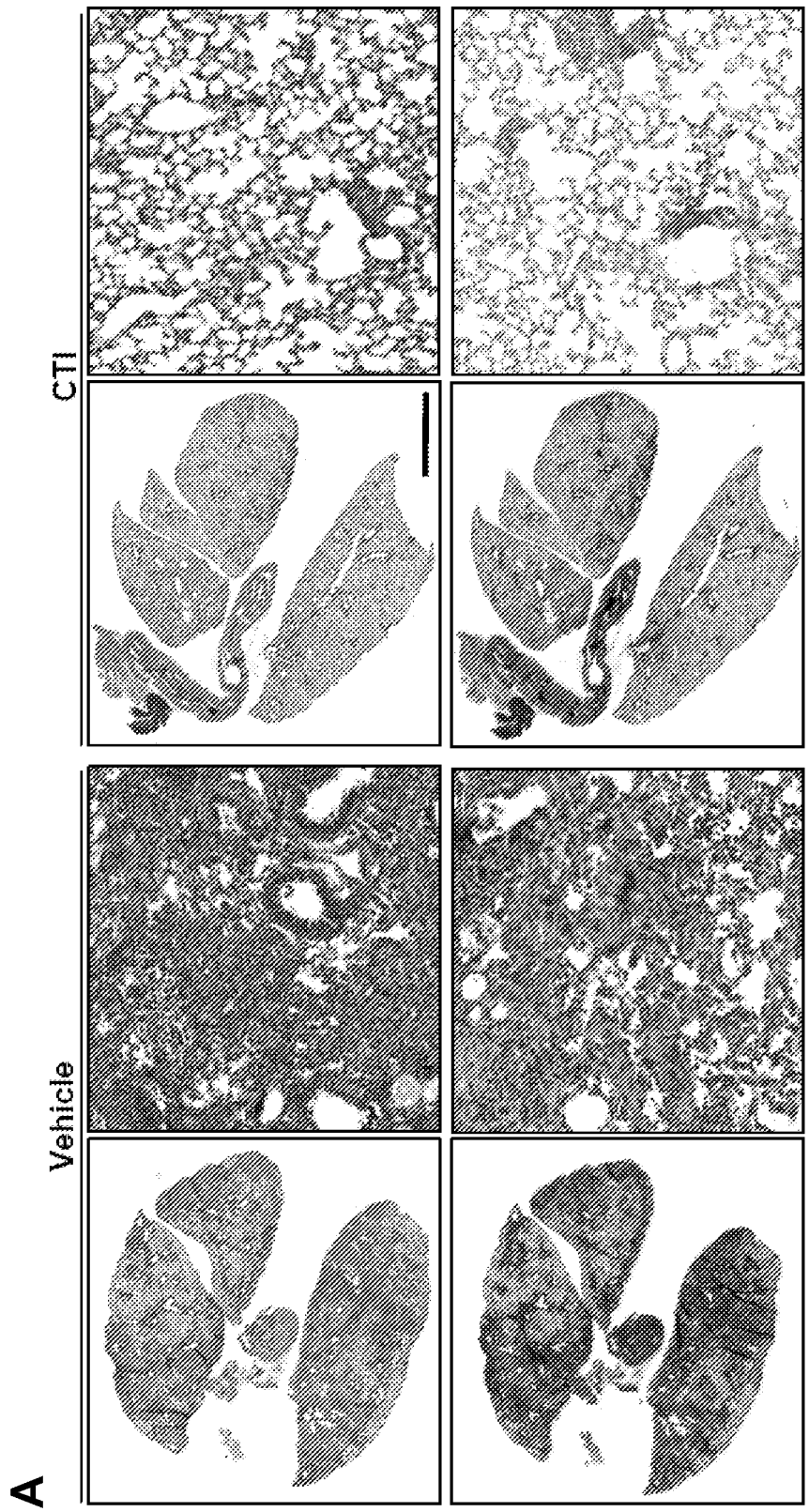
FIG. 25: Administration of FXIIa inhibitor "Corn-trypsin-inhibitor" (CTI) protects against bleomycin-induced IPF situation in mice. (A) Upon bleomycin administration untreated wild-type mice exhibit markedly increased FXII expression as well as collagen deposition, while CTI-treated mice are largely protected against lung remodelling and collagen deposition. (B) The survival curves (Kaplan-Meier plot) indicate that bleomycin-treated mice that received the FXII inhibitor CTI are significantly protected against the IPF-type lung fibrosis. (C) In the CTI receiving treatment group the lung compliance is significantly improved. (D,E) Both, increase in septum thickness and collagen content that are provoked through bleomycin application are significantly prevented in the therapeutic CTI-group of mice.
Figure 25:
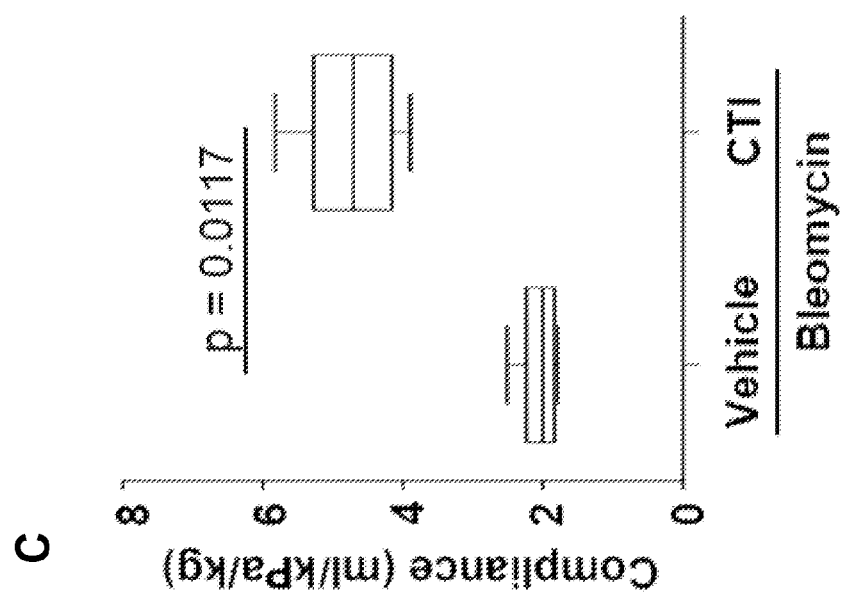
Figure 25:
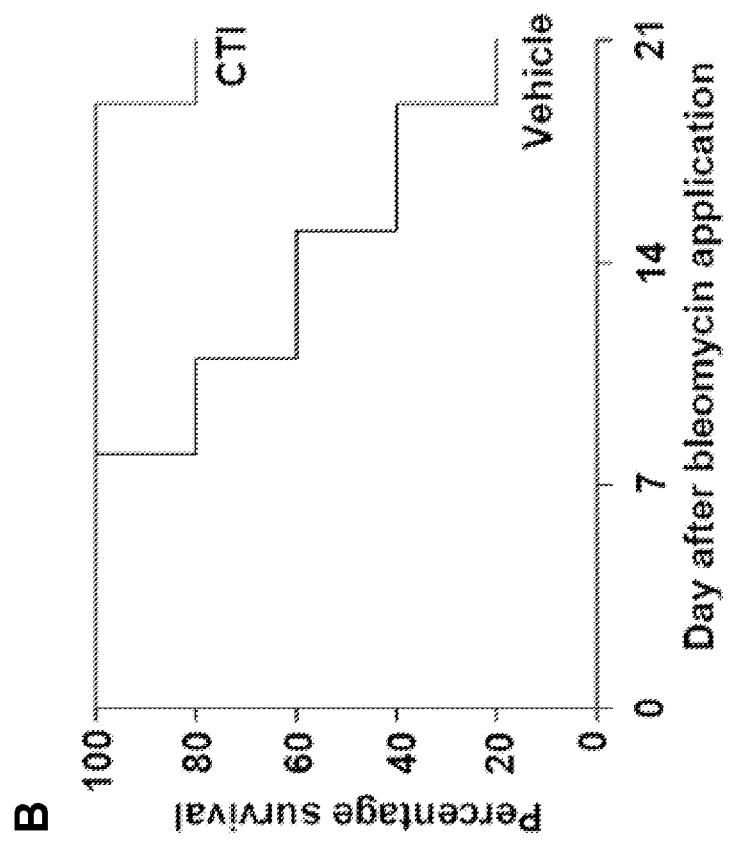
Figure 25:
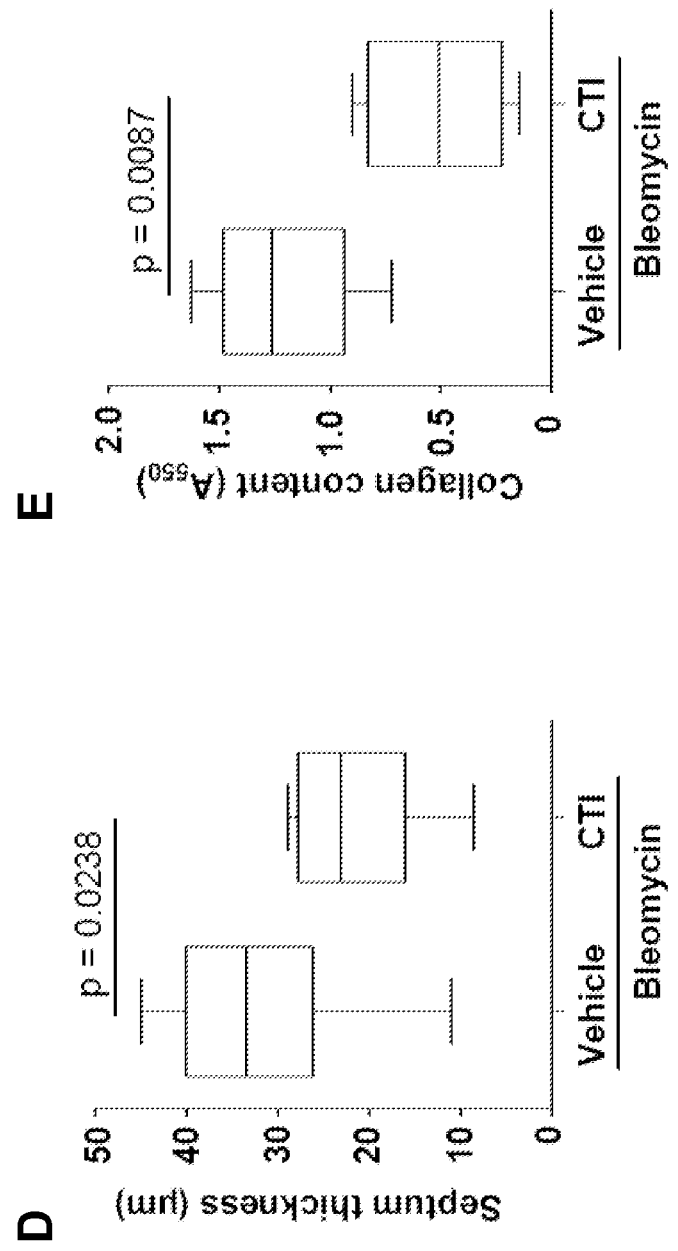

To examine interaction of Smad 3 with SBE-272 ChIP and streptavidin pull-down assays were performed. The ChIP assay clearly demonstrated TGF-β1-induced interaction of Smad 3 with FXII promoter region (-299/+1 bp) flanking SBE-272 (FIG. 22A). To further analyze binding of Smad 3 to SBE-272, streptavidin pull-down using biotinylated template spanning -283 and -258 bp region of FXII promoter was performed. As expected, Smad 3 was eluted from this template, whereas no interaction occurred when SBE-272 was mutated (FIG. 22B). These findings indicate Smad 3-SBE-272 form a complex after stimulation of HLF with TGF-β1.

JNK Kinase Affects Binding of Smad 3 to SBE-272.

Since inhibition of JNK kinase did not have any impact on phosphorylation and translocation of Smad 3 to the nucleus, the involvement of this kinase in the formation of Smad 3-SBE-272 complex was investigated by ChIP and streptavidin pull-down assays. HLF, pretreated with TβRI or JNK1 inhibitors (SB431542 or SP600125, respectively), were either unstimulated or stimulated with TGF-β1, lysed, and ChIP assay was performed using anti-Smad3 antibody and IgG isotyp control. TGF-β1 induced Smad 3-DNA complex formation. This interaction was completely abolished when SB431542 was used, and dramatically reduced in the presence SP600125 (FIG. 22C). SB431542 and SP600125 alone did not affect interaction of Smad3 with DNA (data not shown). Similar results were obtained when streptavidin pull-down assay was performed (FIG. 22D).

The invention claimed is:

1. A method of treating fibroproliferative interstitial lung disease, comprising administering to an individual a pharmaceutically effective amount of a non-endogenous inhibitor of the cellular activity of FXII/FXIIa,
wherein the non-endogenous inhibitor of the cellular activity of FXII/FXIIa is selected from the group consisting of:
(i) wild type Infestin-4 polypeptide sequence (SEQ ID NO: 33), or a variant thereof, wherein the variant comprises
  (a) N-terminal amino acids 2-13 of the wild type Infestin-4 sequence and at least one and up to five amino acid mutations outside said N-terminal amino acids that result in differences from the wild type Infestin-4 sequence;
(ii) SPINK-1 (SEQ ID NO:29), which is mutated to include the N-terminal amino acids 2-13 of the wild type Infestin-4 sequence, or a variant of said mutated SPINK-1, wherein the variant comprises
  (a) the N-terminal amino acids 2-13 of the wild type Infestin-4 sequence; and at least one and up to five amino acid mutations outside said N-terminal amino acids that result in differences from the wild type SPINK-1 sequence and which increase the homology of the variant to the wild type Infestin-4 sequence; and
(iii) an antibody capable of binding to said FXII/FXIIa.

2. A method of prolonging the survival time of a patient suffering from an fibroproliferative interstitial lung disease, comprising administering to said patient a pharmaceutically effective amount of a non-endogenous inhibitor of the cellular activity of FXII/FXIIa,
wherein the non-endogenous inhibitor of the cellular activity of FXII/FXIIa is selected from the group consisting of:
(i) wild type Infestin-4 polypeptide sequence (SEQ ID NO: 33), or a variant thereof, wherein the variant comprises
  (a) N-terminal amino acids 2-13 of the wild type Infestin-4 sequence and at least one and up to five amino acid mutations outside said N-terminal amino acids that result in differences from the wild type Infestin-4 sequence;
(ii) SPINK-1 (SEQ ID NO:29), which is mutated to include the N-terminal amino acids 2-13 of the wild type Infestin-4 sequence, or a variant of said mutated SPINK-1, wherein the variant comprises
  (a) the N-terminal amino acids 2-13 of the wild type Infestin-4 sequence; and at least one and up to five amino acid mutations outside said N-terminal amino acids that result in differences from the wild type SPINK-1 sequence and which increase the homology of the variant to the wild type Infestin-4 sequence; and
(iii) an antibody capable of binding to said FXII/FXIIa.

3. The method according to claim 1, wherein said fibroproliferative interstitial lung disease is idiopathic pulmonary fibrosis.

4. The method according to claim 1, wherein the non-endogenous inhibitor of the cellular activity of FXII/FXIIa is a compound capable of inhibiting the catalytic activity of factor XIIa.

5. The method according to claim 1, wherein the non-endogenous inhibitor of the cellular activity of FXII/FXIIa is a compound capable of inhibiting the conversion of factor XII into factor XIIa.

6. The method according to claim 1, wherein the non-endogenous inhibitor of the cellular activity of FXII/FXIIa is a serine protease inhibitor.

7. The method according to claim 1, wherein the non-endogenous inhibitor of the cellular activity of FXII/FXIIa is linked to a half-life enhancing polypeptide, wherein the half-life enhancing peptide is selected from the group consisting of albumin, afamin, alpha-fetoprotein or vitamin D binding protein, human albumin, or a variant thereof, an immunoglobulin or variant thereof, and an Fc of an IgG.

8. The method according to claim 7, wherein the half-life enhancing polypeptide is linked to the FXII inhibitor via a linker.

9. The method according to claim 8, wherein the linker is cleavable.

10. The method according to claim 1, wherein said fibroproliferative interstitial lung disease is pulmonary fibrosis.

11. The method according to claim 1, wherein said treatment further comprises administering at least one selected from the group consisting of corticosteroid drugs, pirfenidone, azathioprine, cyclophosphamide, acetylcysteine, antifibrotics and oxygen therapy.

12. The method according to claim 2, wherein the non-endogenous inhibitor of the cellular activity of FXII/FXIIa is a compound capable of inhibiting the catalytic activity of factor XIIa.

13. The method according to claim 2, wherein the non-endogenous inhibitor of the cellular activity of FXII/FXIIa is a compound capable of inhibiting the conversion of factor XII into factor XIIa.

14. The method according to claim 2, wherein the non-endogenous inhibitor of the cellular activity of FXII/FXIIa is a serine protease inhibitor.

15. The method according to claim 2, wherein the non-endogenous inhibitor of the cellular activity of FXII/FXIIa is linked to a half-life enhancing polypeptide, wherein the half-life enhancing peptide is selected from the group consisting of albumin, afamin, alpha-fetoprotein or vitamin D binding protein, human albumin, or a variant thereof, an immunoglobulin or variant thereof, and an Fc of an IgG.

16. The method according to claim 15, wherein the half-life enhancing polypeptide is linked to the FXII inhibitor via a linker.

17. The method according to claim 16, wherein the linker is cleavable.

18. The method according to claim 2, wherein said fibroproliferative interstitial lung disease is pulmonary fibrosis.

19. The method according to claim 18, wherein said pulmonary fibrosis is idiopathic pulmonary fibrosis.

20. The method according to claim 2, wherein said treatment further comprises administering at least one selected from the group consisting of corticosteroid drugs, pirfenidone, azathioprine, cyclophosphamide, acetylcysteine, antifibrotics and oxygen therapy.

21. The method according to claim 9, wherein the linker is cleavable by a coagulation protease of the intrinsic, extrinsic or common coagulation pathway.

22. The method according to claim 21, wherein the coagulation protease is Factor XIIa.

23. The method according to claim 17, wherein the linker is cleavable by a coagulation protease of the intrinsic, extrinsic of common coagulation pathway.

24. The method according to claim 23, wherein the coagulation protease is Factor XIIa.

* * * * *

SEQUENCE LISTING

<160> NUMBER OF SEQ ID NOS: 53

<210> SEQ ID NO 1
<211> LENGTH: 21
<212> TYPE: DNA
<213> ORGANISM: Artificial Sequence
<220> FEATURE:
<223> OTHER INFORMATION: human beta-actin forward primer

<400> SEQUENCE: 1
attgccgaca ggatgcagga a                                          21

<210> SEQ ID NO 2
<211> LENGTH: 21
<212> TYPE: DNA
<213> ORGANISM: Artificial Sequence
<220> FEATURE:
<223> OTHER INFORMATION: human beta-actin reverse primer

<400> SEQUENCE: 2
gctgatccac atctgctgga a                                          21

<210> SEQ ID NO 3
<211> LENGTH: 18
<212> TYPE: DNA
<213> ORGANISM: Artificial Sequence
<220> FEATURE:
<223> OTHER INFORMATION: Human FXII forward primer

<400> SEQUENCE: 3
acgacctggc tctgttgc                                              18

<210> SEQ ID NO 4
<211> LENGTH: 17
<212> TYPE: DNA
<213> ORGANISM: Artificial Sequence
<220> FEATURE:
<223> OTHER INFORMATION: human FXII reverse primer

<400> SEQUENCE: 4
cttggcaggc acaccgg                                               17

<210> SEQ ID NO 5
<211> LENGTH: 19
<212> TYPE: DNA
<213> ORGANISM: Artificial Sequence
<220> FEATURE:
<223> OTHER INFORMATION: human FXI forward primer

<400> SEQUENCE: 5
tctggcttgt attagggac                                             19

<210> SEQ ID NO 6
<211> LENGTH: 18
<212> TYPE: DNA
<213> ORGANISM: Artificial Sequence
<220> FEATURE:
<223> OTHER INFORMATION: human FXI reverse primer

<400> SEQUENCE: 6
tctttgggcc attcctgg                                              18

<210> SEQ ID NO 7
<211> LENGTH: 18
<212> TYPE: DNA
<213> ORGANISM: Artificial Sequence

```
<220> FEATURE:
<223> OTHER INFORMATION: human HMWK forward primer

<400> SEQUENCE: 7
aagagtacag gtggtcgc                                                 18

<210> SEQ ID NO 8
<211> LENGTH: 20
<212> TYPE: DNA
<213> ORGANISM: Artificial Sequence
<220> FEATURE:
<223> OTHER INFORMATION: human HMWK reverse primer

<400> SEQUENCE: 8
caatctaggc tttggccaag                                               20

<210> SEQ ID NO 9
<211> LENGTH: 19
<212> TYPE: DNA
<213> ORGANISM: Artificial Sequence
<220> FEATURE:
<223> OTHER INFORMATION: murine FXII forward primer

<400> SEQUENCE: 9
acagtgctct gcgaggtgg                                                19

<210> SEQ ID NO 10
<211> LENGTH: 21
<212> TYPE: DNA
<213> ORGANISM: Artificial Sequence
<220> FEATURE:
<223> OTHER INFORMATION: murine FXII reverse primer

<400> SEQUENCE: 10
cgttagagtt ggagcagcga t                                             21

<210> SEQ ID NO 11
<211> LENGTH: 21
<212> TYPE: DNA
<213> ORGANISM: Artificial Sequence
<220> FEATURE:
<223> OTHER INFORMATION: murine FXI forward primer

<400> SEQUENCE: 11
ttacacagat tttcagcggc c                                             21

<210> SEQ ID NO 12
<211> LENGTH: 21
<212> TYPE: DNA
<213> ORGANISM: Artificial Sequence
<220> FEATURE:
<223> OTHER INFORMATION: murine FXI reverse primer

<400> SEQUENCE: 12
tgtgtacccc catccagtca c                                             21

<210> SEQ ID NO 13
<211> LENGTH: 20
<212> TYPE: DNA
<213> ORGANISM: Artificial Sequence
<220> FEATURE:
<223> OTHER INFORMATION: murine HMWK forward primer

<400> SEQUENCE: 13
ggagaacaaa gtcgtcccga                                               20
```

<210> SEQ ID NO 14
<211> LENGTH: 21
<212> TYPE: DNA
<213> ORGANISM: Artificial Sequence
<220> FEATURE:
<223> OTHER INFORMATION: murine HMWK reverse primer

<400> SEQUENCE: 14
tgtgacactc cggaaaggag a                                              21

<210> SEQ ID NO 15
<211> LENGTH: 20
<212> TYPE: DNA
<213> ORGANISM: Artificial Sequence
<220> FEATURE:
<223> OTHER INFORMATION: murine beta-actin forward primer

<400> SEQUENCE: 15
agagggaaat cgtgcgtgac                                                20

<210> SEQ ID NO 16
<211> LENGTH: 21
<212> TYPE: DNA
<213> ORGANISM: Artificial Sequence
<220> FEATURE:
<223> OTHER INFORMATION: murine beta-actin reverse primer

<400> SEQUENCE: 16
caatagtgat gacctggccg t                                              21

<210> SEQ ID NO 17
<211> LENGTH: 28
<212> TYPE: DNA
<213> ORGANISM: Artificial Sequence
<220> FEATURE:
<223> OTHER INFORMATION: human FXII-1630 forward primer

<400> SEQUENCE: 17
ccgctcgagt gctctgtgct tagtaacc                                       28

<210> SEQ ID NO 18
<211> LENGTH: 26
<212> TYPE: DNA
<213> ORGANISM: Artificial Sequence
<220> FEATURE:
<223> OTHER INFORMATION: human FXII-907 forward primer

<400> SEQUENCE: 18
ccgctcgagc agctacccag gaggct                                         26

<210> SEQ ID NO 19
<211> LENGTH: 27
<212> TYPE: DNA
<213> ORGANISM: Artificial Sequence
<220> FEATURE:
<223> OTHER INFORMATION: human FXII-577 forward primer

<400> SEQUENCE: 19
ccgctcgagg cgtggtggtg ggctcct                                        27

<210> SEQ ID NO 20
<211> LENGTH: 27
<212> TYPE: DNA
<213> ORGANISM: Artificial Sequence
<220> FEATURE:
<223> OTHER INFORMATION: human FXII-299 forward primer

```
<400> SEQUENCE: 20
ccgctcgagc ttaacctcct gatctcc                                           27

<210> SEQ ID NO 21
<211> LENGTH: 26
<212> TYPE: DNA
<213> ORGANISM: Artificial Sequence
<220> FEATURE:
<223> OTHER INFORMATION: human FXII-183DSBE-272 forward primer

<400> SEQUENCE: 21
ccgctcgaga aactcccaaa ctttcc                                            26

<210> SEQ ID NO 22
<211> LENGTH: 29
<212> TYPE: DNA
<213> ORGANISM: Artificial Sequence
<220> FEATURE:
<223> OTHER INFORMATION: human FXII reverse primer

<400> SEQUENCE: 22
cccaagcttc gttggtccag ctgcctatc                                         29

<210> SEQ ID NO 23
<211> LENGTH: 25
<212> TYPE: DNA
<213> ORGANISM: Artificial Sequence
<220> FEATURE:
<223> OTHER INFORMATION: human FXII-299C/T forward primer

<400> SEQUENCE: 23
ccacaggacc tagagcataa gaatg                                             25

<210> SEQ ID NO 24
<211> LENGTH: 25
<212> TYPE: DNA
<213> ORGANISM: Artificial Sequence
<220> FEATURE:
<223> OTHER INFORMATION: human FXII-299C/T reverse primer

<400> SEQUENCE: 24
cattcttatg ctctaggtcc tgtgg                                             25

<210> SEQ ID NO 25
<211> LENGTH: 18
<212> TYPE: DNA
<213> ORGANISM: Artificial Sequence
<220> FEATURE:
<223> OTHER INFORMATION: human FXII-299 bp forward primer

<400> SEQUENCE: 25
cttaacctcc tgatctcc                                                     18

<210> SEQ ID NO 26
<211> LENGTH: 20
<212> TYPE: DNA
<213> ORGANISM: Artificial Sequence
<220> FEATURE:
<223> OTHER INFORMATION: human FXII-299 bp reverse primer

<400> SEQUENCE: 26
cgttggtcca gctgcctatc                                                   20

<210> SEQ ID NO 27
```

-continued

```
<211> LENGTH: 45
<212> TYPE: DNA
<213> ORGANISM: Artificial Sequence
<220> FEATURE:
<223> OTHER INFORMATION: Synthetic oligonucleotide: SBE-283/-258
<220> FEATURE:
<221> NAME/KEY: misc_feature
<222> LOCATION: (1)..(1)
<223> OTHER INFORMATION: 5'-biotin

<400> SEQUENCE: 27
cttaacctcc tgatctccac aggacccaga gcataagaat gtccc            45

<210> SEQ ID NO 28
<211> LENGTH: 45
<212> TYPE: DNA
<213> ORGANISM: Artificial Sequence
<220> FEATURE:
<223> OTHER INFORMATION: Synthetic oligonucleotide: SBE-283/-258 C/T
<220> FEATURE:
<221> NAME/KEY: misc_feature
<222> LOCATION: (1)..(1)
<223> OTHER INFORMATION: 5'-biotin

<400> SEQUENCE: 28
cttaacctcc tgatctccac aggacctaga gcataagaat gtccc            45

<210> SEQ ID NO 29
<211> LENGTH: 56
<212> TYPE: PRT
<213> ORGANISM: Homo sapiens

<400> SEQUENCE: 29

Asp Ser Leu Gly Arg Glu Ala Lys Cys Tyr Asn Glu Leu Asn Gly Cys
1               5                   10                  15

Thr Lys Ile Tyr Asp Pro Val Cys Gly Thr Asp Gly Asn Thr Tyr Pro
            20                  25                  30

Asn Glu Cys Val Leu Cys Phe Glu Asn Arg Lys Arg Gln Thr Ser Ile
        35                  40                  45

Leu Ile Gln Lys Ser Gly Pro Cys
    50                  55

<210> SEQ ID NO 30
<211> LENGTH: 53
<212> TYPE: PRT
<213> ORGANISM: Artificial Sequence
<220> FEATURE:
<223> OTHER INFORMATION: Synthetic SPINK-K1 mutant protein

<400> SEQUENCE: 30

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Pro Asn Glu Cys
            20                  25                  30

Val Leu Cys Phe Glu Asn Arg Lys Arg Gln Thr Ser Ile Leu Ile Gln
        35                  40                  45

Lys Ser Gly Pro Cys
    50

<210> SEQ ID NO 31
<211> LENGTH: 53
<212> TYPE: PRT
<213> ORGANISM: Artificial Sequence
<220> FEATURE:
<223> OTHER INFORMATION: Synthetic SPINK-2 mutant protein
```

<400> SEQUENCE: 31

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys
                20                  25                  30

Met Leu Cys Ala Glu Asn Arg Lys Arg Gln Thr Ser Ile Leu Ile Gln
            35                  40                  45

Lys Glu Gly Pro Cys
        50

<210> SEQ ID NO 32
<211> LENGTH: 54
<212> TYPE: PRT
<213> ORGANISM: Artificial Sequence
<220> FEATURE:
<223> OTHER INFORMATION: Synthetic SPINK-K3 mutant protein

<400> SEQUENCE: 32

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys
                20                  25                  30

Met Leu Asn Cys Ala Glu Asn Arg Lys Arg Gln Thr Ser Ile Leu Ile
            35                  40                  45

Gln Lys Glu Gly Pro Cys
        50

<210> SEQ ID NO 33
<211> LENGTH: 48
<212> TYPE: PRT
<213> ORGANISM: Triatoma infestans

<400> SEQUENCE: 33

Glu Val Arg Asn Pro Cys Ala Cys Phe Arg Asn Tyr Val Pro Val Cys
1               5                   10                  15

Gly Ser Asp Gly Lys Thr Tyr Gly Asn Pro Cys Met Leu Asn Cys Ala
                20                  25                  30

Ala Gln Thr Lys Val Pro Gly Leu Lys Leu Val His Glu Gly Arg Cys
            35                  40                  45

<210> SEQ ID NO 34
<211> LENGTH: 585
<212> TYPE: PRT
<213> ORGANISM: Homo sapiens

<400> SEQUENCE: 34

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

-continued

```
Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
            290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
            370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510
```

```
Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 35
<211> LENGTH: 81
<212> TYPE: DNA
<213> ORGANISM: Artificial Sequence
<220> FEATURE:
<223> OTHER INFORMATION: Synthetic SPINK fragment S1

<400> SEQUENCE: 35
gaattcgcca ccatgaaggt gaccggcatc ttcctgctgt ccgccctggc cctgctgtcc    60
ctgtccggca acaccggcgc c                                              81

<210> SEQ ID NO 36
<211> LENGTH: 84
<212> TYPE: DNA
<213> ORGANISM: Artificial Sequence
<220> FEATURE:
<223> OTHER INFORMATION: Synthetic SPINK fragment S2wt

<400> SEQUENCE: 36
ggcgccgact ccctgggccg cgaggccaag tgctacaacg agctgaacgg ctgcaccaag    60
atctacgacc ccgtgtgcgg tacc                                           84

<210> SEQ ID NO 37
<211> LENGTH: 75
<212> TYPE: DNA
<213> ORGANISM: Artificial Sequence
<220> FEATURE:
<223> OTHER INFORMATION: Synthetic SPINK fragment S2K1

<400> SEQUENCE: 37
ggcgccgact ccctgggccg cgaggtgcgc aaccctgcg cctgcttccg caactacgtg    60
cccgtgtgcg gtacc                                                     75

<210> SEQ ID NO 38
<211> LENGTH: 105
<212> TYPE: DNA
<213> ORGANISM: Artificial Sequence
<220> FEATURE:
<223> OTHER INFORMATION: Synthetic SPINK fragment S3wt

<400> SEQUENCE: 38
ggtaccgacg gcaacaccta ccccaacgag tgcgtgctgt gcttcgagaa ccgcaagcgc    60
cagacctcca tcctgatcca gaagtccggc ccctgctgag gatcc                   105

<210> SEQ ID NO 39
<211> LENGTH: 108
<212> TYPE: DNA
<213> ORGANISM: Artificial Sequence
<220> FEATURE:
<223> OTHER INFORMATION: Synthetic SPINK fragment S3K3
```

```
<400> SEQUENCE: 39
ggtaccgacg gcaacaccta cggcaacgag tgcatgctga actgcgccga gaaccgcaag      60
cgccagacct ccatcctgat ccagaaggag ggcccctgct gaggatcc                  108

<210> SEQ ID NO 40
<211> LENGTH: 25
<212> TYPE: DNA
<213> ORGANISM: Artificial Sequence
<220> FEATURE:
<223> OTHER INFORMATION: Mutagenesis oligonucleotide We2450

<400> SEQUENCE: 40
cgagtgcatg ctgtgcgccg agaac                                            25

<210> SEQ ID NO 41
<211> LENGTH: 25
<212> TYPE: DNA
<213> ORGANISM: Artificial Sequence
<220> FEATURE:
<223> OTHER INFORMATION: Mutagenesis oligonucleotide We2451

<400> SEQUENCE: 41
gttctcggcg cacagcatgc actcg                                            25

<210> SEQ ID NO 42
<211> LENGTH: 107
<212> TYPE: DNA
<213> ORGANISM: Artificial Sequence
<220> FEATURE:
<223> OTHER INFORMATION: Synthetic Infestin-4 fragment I4C

<400> SEQUENCE: 42
agatctgacg gaaagaccta cggcaacccc tgcatgctga actgtgccgc ccagaccaag      60 gtgcccggc tcaagctggt gcacgagggc cgctgctagg cggccgc                    107

<210> SEQ ID NO 43
<211> LENGTH: 37
<212> TYPE: DNA
<213> ORGANISM: Artificial Sequence
<220> FEATURE:
<223> OTHER INFORMATION: Mutagenesis oligonucleotide We2467

<400> SEQUENCE: 43
gctgccttag gcttaggagg atccagcgct gtgaagg                               37

<210> SEQ ID NO 44
<211> LENGTH: 37
<212> TYPE: DNA
<213> ORGANISM: Artificial Sequence
<220> FEATURE:
<223> OTHER INFORMATION: Mutagenesis oligonucleotide We2468

<400> SEQUENCE: 44
ccttcacagc gctggatcct cctaagccta aggcagc                               37

<210> SEQ ID NO 45
<211> LENGTH: 29
<212> TYPE: DNA
<213> ORGANISM: Artificial Sequence
<220> FEATURE:
<223> OTHER INFORMATION: PCR primer We2470

<400> SEQUENCE: 45
cgcgcggccg cgatcctcag caggggccg                                        29
```

-continued

<210> SEQ ID NO 46
<211> LENGTH: 42
<212> TYPE: DNA
<213> ORGANISM: Artificial Sequence
<220> FEATURE:
<223> OTHER INFORMATION: PCR primer We2473

<400> SEQUENCE: 46
gcgggatccg gggggagcgg cggctccgac tccctgggcc gc        42

<210> SEQ ID NO 47
<211> LENGTH: 18
<212> TYPE: DNA
<213> ORGANISM: Artificial Sequence
<220> FEATURE:
<223> OTHER INFORMATION: PCR primer We2623

<400> SEQUENCE: 47
ctgctggcgg ccgcctag        18

<210> SEQ ID NO 48
<211> LENGTH: 650
<212> TYPE: PRT
<213> ORGANISM: Homo sapiens

<400> SEQUENCE: 48

Asp Ala His Lys Ser Glu Val Ala His Arg Phe Lys Asp Leu Gly Glu
1               5                  10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp

```
                    245                 250                 255
Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Ser Gly Ser Gly
            580                 585                 590

Gly Ser Asp Ser Leu Gly Arg Glu Ala Lys Cys Tyr Asn Glu Leu Asn
        595                 600                 605

Gly Cys Thr Lys Ile Tyr Asp Pro Val Cys Gly Thr Asp Gly Asn Thr
610                 615                 620

Tyr Pro Asn Glu Cys Val Leu Cys Phe Glu Asn Arg Lys Arg Gln Thr
625                 630                 635                 640

Ser Ile Leu Ile Gln Lys Ser Gly Pro Cys
                645                 650

<210> SEQ ID NO 49
```

```
<211> LENGTH: 647
<212> TYPE: PRT
<213> ORGANISM: Homo sapiens

<400> SEQUENCE: 49
```

| | | | | | | | | | | | | | | |
|---|---|---|---|---|---|---|---|---|---|---|---|---|---|---|
| Asp | Ala | His | Lys | Ser | Glu | Val | Ala | His | Arg | Phe | Lys | Asp | Leu | Gly | Glu |
| 1 | | | | 5 | | | | | 10 | | | | | 15 | |

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                    85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                    165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                    245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                    325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu

```
            385                 390                 395                 400
Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Ser Gly Ser Gly Gly
            580                 585                 590

Gly Ser Asp Ser Leu Gly Arg Glu Val Arg Asn Pro Cys Ala Cys Phe
        595                 600                 605

Arg Asn Tyr Val Pro Val Cys Gly Thr Asp Gly Asn Thr Tyr Pro Asn
    610                 615                 620

Glu Cys Val Leu Cys Phe Glu Asn Arg Lys Arg Gln Thr Ser Ile Leu
625                 630                 635                 640

Ile Gln Lys Ser Gly Pro Cys
                645

<210> SEQ ID NO 50
<211> LENGTH: 647
<212> TYPE: PRT
<213> ORGANISM: Homo sapiens

<400> SEQUENCE: 50

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110
```

-continued

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu

```
                530             535                 540
Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Ser Gly
                580                 585                 590

Gly Ser Asp Ser Leu Gly Arg Glu Val Arg Asn Pro Cys Ala Cys Phe
        595                 600                 605

Arg Asn Tyr Val Pro Val Cys Gly Thr Asp Gly Asn Thr Tyr Gly Asn
        610                 615                 620

Glu Cys Met Leu Cys Ala Glu Asn Arg Lys Arg Gln Thr Ser Ile Leu
625                 630                 635                 640

Ile Gln Lys Glu Gly Pro Cys
                645

<210> SEQ ID NO 51
<211> LENGTH: 648
<212> TYPE: PRT
<213> ORGANISM: Homo sapiens

<400> SEQUENCE: 51

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255
```

Arg Ala Asp Leu Ala Lys Tyr Ile Cys Glu Asn Gln Asp Ser Ile Ser
             260                 265                 270

Ser Lys Leu Lys Glu Cys Cys Glu Lys Pro Leu Leu Glu Lys Ser His
         275                 280                 285

Cys Ile Ala Glu Val Glu Asn Asp Glu Met Pro Ala Asp Leu Pro Ser
     290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                 325                 330                 335

Arg His Pro Asp Tyr Ser Val Val Leu Leu Leu Arg Leu Ala Lys Thr
             340                 345                 350

Tyr Glu Thr Thr Leu Glu Lys Cys Cys Ala Ala Ala Asp Pro His Glu
         355                 360                 365

Cys Tyr Ala Lys Val Phe Asp Glu Phe Lys Pro Leu Val Glu Glu Pro
     370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                 405                 410                 415

Gln Val Ser Thr Pro Thr Leu Val Glu Val Ser Arg Asn Leu Gly Lys
             420                 425                 430

Val Gly Ser Lys Cys Cys Lys His Pro Glu Ala Lys Arg Met Pro Cys
         435                 440                 445

Ala Glu Asp Tyr Leu Ser Val Val Leu Asn Gln Leu Cys Val Leu His
     450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                 485                 490                 495

Tyr Val Pro Lys Glu Phe Asn Ala Glu Thr Phe Thr Phe His Ala Asp
             500                 505                 510

Ile Cys Thr Leu Ser Glu Lys Glu Arg Gln Ile Lys Lys Gln Thr Ala
         515                 520                 525

Leu Val Glu Leu Val Lys His Lys Pro Lys Ala Thr Lys Glu Gln Leu
     530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                 565                 570                 575

Ala Ala Ser Gln Ala Ala Leu Gly Leu Gly Gly Ser Gly Ser Gly
             580                 585                 590

Gly Ser Asp Ser Leu Gly Arg Glu Val Arg Asn Pro Cys Ala Cys Phe
         595                 600                 605

Arg Asn Tyr Val Pro Val Cys Gly Thr Asp Gly Asn Thr Tyr Gly Asn
     610                 615                 620

Glu Cys Met Leu Asn Cys Ala Glu Asn Arg Lys Arg Gln Thr Ser Ile
625                 630                 635                 640

Leu Ile Gln Lys Glu Gly Pro Cys
                 645

<210> SEQ ID NO 52
<211> LENGTH: 647
<212> TYPE: PRT

<213> ORGANISM: Homo sapiens

<400> SEQUENCE: 52

```
Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
            20                  25                  30
Gln Cys Pro Phe Glu Asp His Val Lys Leu Val Asn Glu Val Thr Glu
        35                  40                  45
Phe Ala Lys Thr Cys Val Ala Asp Glu Ser Ala Glu Asn Cys Asp Lys
    50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
370                 375                 380
Gln Asn Leu Ile Lys Gln Asn Cys Glu Leu Phe Glu Gln Leu Gly Glu
385                 390                 395                 400
```

```
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
    530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu Gly Gly Ser Gly Gly Ser Gly
            580                 585                 590
Gly Ser Asp Ser Leu Gly Arg Glu Val Arg Asn Pro Cys Ala Cys Phe
        595                 600                 605
Arg Asn Tyr Val Pro Val Cys Gly Ser Asp Gly Lys Thr Tyr Gly Asn
    610                 615                 620
Pro Cys Met Leu Asn Cys Ala Ala Gln Thr Lys Val Pro Gly Leu Lys
625                 630                 635                 640
Leu Val His Glu Gly Arg Cys
                645

<210> SEQ ID NO 53
<211> LENGTH: 294
<212> TYPE: PRT
<213> ORGANISM: Homo sapiens

<400> SEQUENCE: 53

Asp Ser Leu Gly Arg Glu Val Arg Asn Pro Cys Ala Cys Phe Arg Asn
1               5                   10                  15
Tyr Val Pro Val Cys Gly Thr Asp Gly Asn Thr Tyr Gly Asn Glu Cys
            20                  25                  30
Met Leu Cys Ala Glu Asn Arg Lys Arg Gln Thr Ser Ile Leu Ile Gln
        35                  40                  45
Lys Glu Gly Pro Cys Gly Ser Gly Gly Ser Gly Gly Ser Glu Pro
    50                  55                  60
Lys Ser Cys Asp Lys Thr His Thr Cys Pro Pro Cys Pro Ala Pro Glu
65                  70                  75                  80
Leu Leu Gly Gly Pro Ser Val Phe Leu Phe Pro Pro Lys Pro Lys Asp
                85                  90                  95
Thr Leu Met Ile Ser Arg Thr Pro Glu Val Thr Cys Val Val Val Asp
            100                 105                 110
Val Ser His Glu Asp Pro Glu Val Lys Phe Asn Trp Tyr Val Asp Gly
        115                 120                 125
```

-continued

```
Val Glu Val His Asn Ala Lys Thr Lys Pro Arg Glu Glu Gln Tyr Asn
    130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
                180                 185                 190

Pro Gln Val Tyr Thr Leu Pro Pro Ser Arg Glu Glu Met Thr Lys Asn
            195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
                260                 265                 270

Ser Val Met His Glu Ala Leu His Asn His Tyr Thr Gln Lys Ser Leu
            275                 280                 285

Ser Leu Ser Pro Gly Lys
    290
```